US009511099B2

(12) United States Patent
Jones et al.

(10) Patent No.: US 9,511,099 B2
(45) Date of Patent: *Dec. 6, 2016

(54) MICROBIOTA RESTORATION THERAPY (MRT), COMPOSITIONS AND METHODS OF MANUFACTURE

(71) Applicant: Rebiotix, Inc., Roseville, MN (US)

(72) Inventors: Lee A. Jones, Fridley, MN (US); Courtney R. Jones, Fridley, MN (US); Edwin J. Hlavka, Minneapolis, MN (US); Ryan D. Gordon, Edina, MN (US)

(73) Assignee: REBIOTIX, INC., Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,927

(22) Filed: Oct. 2, 2014

(65) Prior Publication Data

US 2015/0044173 A1    Feb. 12, 2015

Related U.S. Application Data

(63) Continuation-in-part of application No. 14/295,686, filed on Jun. 4, 2014.

(60) Provisional application No. 61/831,409, filed on Jun. 5, 2013.

(51) Int. Cl.
*A01N 63/00* (2006.01)
*A61K 35/74* (2015.01)
*A61K 47/10* (2006.01)
*A61K 31/7048* (2006.01)
*A61K 31/437* (2006.01)
*A61K 31/5377* (2006.01)
*A61K 31/65* (2006.01)
*A61K 31/546* (2006.01)
*A61K 31/4164* (2006.01)
*A61K 35/38* (2015.01)

(52) U.S. Cl.
CPC ........... *A61K 35/74* (2013.01); *A61K 31/4164* (2013.01); *A61K 31/437* (2013.01); *A61K 31/5377* (2013.01); *A61K 31/546* (2013.01); *A61K 31/65* (2013.01); *A61K 31/7048* (2013.01); *A61K 35/38* (2013.01); *A61K 47/10* (2013.01)

(58) Field of Classification Search
None
See application file for complete search history.

(56) References Cited

U.S. PATENT DOCUMENTS

| | | |
|---|---|---|
| 3,317,675 A | 5/1967 | Harris et al. |
| 5,196,205 A | 3/1993 | Borody |
| 5,229,374 A | 7/1993 | Burton et al. |
| 5,274,001 A | 12/1993 | Borody |
| 5,443,826 A | 8/1995 | Borody |
| 5,476,669 A | 12/1995 | Borody |
| 5,519,014 A | 5/1996 | Borody |
| 5,599,795 A | 2/1997 | McCann et al. |
| 5,711,446 A | 1/1998 | Jeffs et al. |
| 5,858,403 A | 1/1999 | Borody et al. |
| 5,925,354 A | 7/1999 | Fuller et al. |
| 6,096,310 A | 8/2000 | Bier |
| 6,103,268 A | 8/2000 | Borody et al. |
| 6,132,767 A | 10/2000 | Borody et al. |
| 6,214,341 B1 | 4/2001 | Thomas, Jr. et al. |
| 6,426,338 B1 | 7/2002 | Borody |
| 6,428,783 B1 | 8/2002 | Khachatrian et al. |
| 6,635,260 B1 | 10/2003 | Gerdin |
| 6,645,530 B1 | 11/2003 | Borody |
| 6,680,168 B2 | 1/2004 | Thomas, Jr. et al. |
| 6,805,852 B2 | 10/2004 | Lin et al. |
| 6,861,053 B1 | 3/2005 | Lin et al. |
| 6,969,520 B2 | 11/2005 | Thomas, Jr. et al. |
| 7,048,906 B2 | 5/2006 | Lin et al. |
| 7,125,708 B2 | 10/2006 | Wynne et al. |
| 7,307,062 B2 | 12/2007 | Bolte |
| 7,607,776 B1 | 10/2009 | Lewis et al. |
| 7,993,682 B2 | 8/2011 | Borody et al. |
| 8,058,418 B2 | 11/2011 | Boyle et al. |
| 8,110,177 B2 | 2/2012 | Lin et al. |
| 8,460,648 B2 | 6/2013 | Borody |
| 8,772,242 B2 | 7/2014 | Borody |
| 2002/0022019 A1 | 2/2002 | Lauland |
| 2003/0031659 A1 | 2/2003 | Farmer |

(Continued)

FOREIGN PATENT DOCUMENTS

| | | |
|---|---|---|
| CA | 1330759 C | 7/1994 |
| CA | 1333564 C | 12/1994 |

(Continued)

OTHER PUBLICATIONS

Jorup-Ronstrom et al., Scand. J. Gasto., 47:548-552 (2012).*
Aas et al., Clin. Infect. Dis., 36:580-585 (2003).*
Kumar, P., et al., "Comparative Analysis of Fecal Microflora of Healthy Full-Term Indian Infants born with Different Methods of Delivery (vaginal vs Cesarean): *Acinetobacter* sp. Prevalence in Vaginally Born Infants", Journal of Bioscience, vol. 37, No. 6, Dec. 2012, pp. 989-998, Indian Academy of Sciences.
Kump, P., et al., "Alteration of Intestinal Dysbiosis by Fecal Microbiota Transplantation Does not Induce Remission in Patients with Chronic Active Ulcerative Colitis", Inflamm Bowel Dis, 2013, pp. 1-11, Crohn's & Colitis Foundation of America, Inc.

(Continued)

*Primary Examiner* — Thomas J Visone
(74) *Attorney, Agent, or Firm* — Seager, Tufte & Wickhem, LLP

(57) ABSTRACT

Microbiota restoration therapy compositions and methods for manufacturing, processing, and/or delivering microbiota restoration therapy compositions are disclosed. An example method for manufacturing a microbiota restoration therapy composition may include collecting a human fecal sample and adding a diluent to the human fecal sample to form a diluted sample. The diluent may include a cryoprotectant. The method may also include mixing the diluted sample with a mixing apparatus and filtering the diluted sample. Filtering may form a filtrate. The method may also include transferring the filtrate to a sample bag and sealing the sample bag.

20 Claims, 9 Drawing Sheets

(56) References Cited

U.S. PATENT DOCUMENTS

| | | |
|---|---|---|
| 2003/0154105 A1 | 8/2003 | Ferguson |
| 2003/0161871 A1 | 8/2003 | Hird et al. |
| 2003/0180260 A1 | 9/2003 | Clancy et al. |
| 2004/0028689 A1 | 2/2004 | Borody |
| 2004/0062757 A1 | 4/2004 | Finegold |
| 2004/0167062 A1 | 8/2004 | Bolte |
| 2004/0170617 A1 | 9/2004 | Finegold |
| 2004/0265291 A1 | 12/2004 | Drake et al. |
| 2005/0074441 A1 | 4/2005 | Collins et al. |
| 2005/0209883 A1 | 9/2005 | Fletcher-Haynes et al. |
| 2005/0239706 A1 | 10/2005 | Backhed et al. |
| 2005/0271749 A1 | 12/2005 | Borody et al. |
| 2006/0008511 A1 | 1/2006 | Lin et al. |
| 2006/0029608 A1 | 2/2006 | Thomas, Jr. et al. |
| 2006/0160121 A1 | 7/2006 | Mounts et al. |
| 2006/0210448 A1 | 9/2006 | Wang et al. |
| 2007/0178078 A1 | 8/2007 | Khoo |
| 2007/0231336 A1 | 10/2007 | Thomas, Jr. et al. |
| 2008/0027353 A1 | 1/2008 | Kliman |
| 2008/0254009 A1 | 10/2008 | Finegold |
| 2008/0269258 A1 | 10/2008 | Breaker et al. |
| 2009/0148540 A1 | 6/2009 | Martin et al. |
| 2009/0305253 A1 | 12/2009 | Breaker et al. |
| 2010/0008850 A1 | 1/2010 | Martin |
| 2010/0172874 A1 | 7/2010 | Turnbaugh et al. |
| 2010/0316617 A1 | 12/2010 | Renaud et al. |
| 2011/0123501 A1 | 5/2011 | Chou et al. |
| 2011/0129529 A1 | 6/2011 | Lin |
| 2011/0177976 A1 | 7/2011 | Gordon et al. |
| 2011/0200570 A1 | 8/2011 | Mosbaugh et al. |
| 2011/0223252 A1 | 9/2011 | Borody et al. |
| 2012/0252775 A1 | 10/2012 | Finegold |
| 2012/0276059 A1 | 11/2012 | Boone et al. |
| 2012/0276060 A1 | 11/2012 | Boone et al. |
| 2013/0022575 A1 | 1/2013 | Cassity |
| 2013/0045274 A1 | 2/2013 | Hlavka |
| 2013/0052172 A1 | 2/2013 | Baker |
| 2013/0064885 A1 | 3/2013 | Lin et al. |
| 2013/0108598 A1 | 5/2013 | Oresic et al. |
| 2013/0149339 A1 | 6/2013 | Honda et al. |
| 2013/0195804 A1 | 8/2013 | Borody |
| 2013/0195820 A1 | 8/2013 | Wacklin et al. |
| 2013/0266539 A1 | 10/2013 | Borody |
| 2014/0147417 A1 | 5/2014 | Sadowsky et al. |
| 2014/0147425 A1 | 5/2014 | Henn et al. |
| 2014/0199281 A1 | 7/2014 | Henn et al. |
| 2014/0234260 A1 | 8/2014 | Borody |
| 2014/0238154 A1 | 8/2014 | Stevens |

FOREIGN PATENT DOCUMENTS

| | | |
|---|---|---|
| CA | 1337265 C | 10/1995 |
| CA | 2189418 A1 | 5/1997 |
| CA | 2289717 A1 | 11/1997 |
| CA | 2232001 C | 12/2002 |
| CA | 2090125 C | 7/2003 |
| CA | 2478135 A1 | 9/2003 |
| CA | 2582137 A1 | 2/2007 |
| CA | 2289717 C | 2/2009 |
| CA | 2189418 C | 7/2011 |
| CN | 1444484 A | 9/2003 |
| CN | 102159084 A | 8/2011 |
| DE | 3889547 T2 | 11/1994 |
| DE | 68928665 T2 | 11/1998 |
| EP | 0433299 A1 | 6/1991 |
| EP | 0397689 B1 | 5/1994 |
| EP | 0771562 A2 | 5/1997 |
| EP | 1300472 A1 | 4/2003 |
| EP | 0554291 B1 | 12/2003 |
| EP | 0952773 B1 | 11/2005 |
| EP | 0980246 B1 | 12/2006 |
| EP | 2030623 A1 | 3/2009 |
| EP | 1340078 B1 | 5/2009 |
| EP | 1432786 B1 | 7/2009 |
| EP | 0554291 B2 | 10/2010 |
| EP | 2636684 A1 | 9/2013 |
| JP | 2009022280 A | 2/2009 |
| WO | 8903219 A1 | 4/1989 |
| WO | 8905659 A1 | 6/1989 |
| WO | 9001335 A1 | 2/1990 |
| WO | 9206690 A1 | 4/1992 |
| WO | 9611014 A1 | 4/1996 |
| WO | 9641615 A2 | 12/1996 |
| WO | 9709886 A1 | 3/1997 |
| WO | 9850043 A1 | 11/1998 |
| WO | 0193904 A1 | 12/2001 |
| WO | 0197821 A1 | 12/2001 |
| WO | 0207741 A1 | 1/2002 |
| WO | 03002713 A2 | 1/2003 |
| WO | 03074061 A1 | 9/2003 |
| WO | 2007018563 A2 | 2/2007 |
| WO | 2008076696 A2 | 6/2008 |
| WO | 2009120347 A2 | 10/2009 |
| WO | 2010002890 A2 | 1/2010 |
| WO | 2010019208 A1 | 2/2010 |
| WO | 2011033310 A1 | 3/2011 |
| WO | 2011036539 A1 | 3/2011 |
| WO | 2011047439 A1 | 4/2011 |
| WO | 2011050397 A1 | 5/2011 |
| WO | 2011094027 A1 | 8/2011 |
| WO | WO 2011/094027 * | 8/2011 ............... C12N 1/12 |
| WO | 2012013861 A2 | 2/2012 |
| WO | 2012016287 A2 | 2/2012 |
| WO | 2012024638 A2 | 2/2012 |
| WO | WO 2012/016287 * | 2/2012 ............ A61K 35/12 |
| WO | 2012033814 A2 | 3/2012 |
| WO | 2012122478 A1 | 9/2012 |
| WO | 2012122522 A1 | 9/2012 |
| WO | 2012142605 A1 | 10/2012 |
| WO | 2012149351 A1 | 11/2012 |
| WO | 2013053836 A1 | 4/2013 |
| WO | 2013090825 A1 | 6/2013 |
| WO | 2013163582 A1 | 10/2013 |
| WO | 2013171515 A1 | 11/2013 |
| WO | 2014078911 A1 | 5/2014 |
| WO | 2014082050 A1 | 5/2014 |
| WO | 2014121298 A3 | 8/2014 |
| WO | 2014121301 A1 | 8/2014 |
| WO | 2014121302 A3 | 8/2014 |
| WO | 2014121304 A1 | 8/2014 |

OTHER PUBLICATIONS

Kunde, S., et al., "Safety, Tolerability and Clinical Response after Fecal Transplantation in Children and Young Adults with Ulcerative Colitis", JPGN, vol. 56, No. 6, Jun. 2013, pp. 596-601.

Kyne, L., et al., "Asymptomatic Carriage of Clostridium Difficile and Serum Levels of IgG Antibody Against Toxin A", The New England Journal of Medicine, vol. 342, No. 6, Feb. 10, 2000, pp. 390-397.

Lagier, J., et al., "Microbial Culturomics: Paradigm Shift in the Human Gut Microbiome Study", Clinical Microbiology and Infection, vol. 18, 2012, pp. 1185-1193, European Society of Clinical Microbiology and Infectious Diseases.

Laksminarayana, B., et al., "Prevalence and Characterization of Clostridium Perfringens from the Faecal Microbiota of Elderly Irish Subjects", Journal of Medical Microbiology, vol. 62, 2013, pp. 457-466, SGM, Great Britain.

Landy, J., et al., "Review Article: Faecal Transplantation Therapy for Gastrointestinal Disease", Alimentary Pharmacology and Therapeutics, vol. 34, 2011, pp. 409-415, Blackwell Publishing Ltd.

Larson, H.E, et al., "Epidemiology of Clostridium difficile in infants", J Infect Dis., Dec. 1982; 146(6):727-33.

Lawley, T.D., et al., "Intestinal colonization resistance", Immunology, Jan. 2013; 138(1):1-11.

Lee, C., et al., "The outcome and long-term follow-up of 94 patients with recurrent and refractory Clostridium difficile infection using single to multiple fecal microbiota transplantation via retention enema", Eur J. Clin Microbiol Infect Dis., Mar. 14, 2014 (4 pgs.).

Lee, S.M., et al., "Bacterial Colonization Factors Control Specificity and Stability of the Gut Microbiota", Nature, vol. 000, 2013, pp. 1-6, Macmillan Publishers Limited.

(56) References Cited

OTHER PUBLICATIONS

Lemon, K., et al., "Microbiota-Targeted Therapies: An Ecological Perspective", Science Translation Medicine, vol. 4, Issue 137, Jun. 6, 2012, pp. 1-9, American Association for the Advancement of Science, Washington, DC.
Ley, R., "The sweet tooth of Clostridium difficile", Nature Medicine, vol. 20, No. 3, Mar. 2014, pp. 248-249.
Liao, C.H., et al., "Survivability and Long-Term Preservation of Bacteria in Water and in Phosphate-Buffered Saline", Letters in Applied Microbiology, vol. 37, Dec. 10, 2002, pp. 45-50.
Lichtman, J., et al., "Host-Centric Proteomics of Stool: A Novel Strategy Focused on Intestinal Responses to the Gut Microbiota", Aug. 27, 2013, pp. 1-27, The American Society of Biochemistry and Molecular Biology, Inc.
Lin, H.J., et al., "Risk factors for Clostridium difficile Associated Diarrhea Among Hospitalized Adults with Fecal Toxigenic C. difficile Colonization", Journal of Microbiology, Immunology and Infection, 2013, pp. 1-7, Elsevier Taiwan LLC.
Liu, Z. et al., "Microbiota Regulation of Inflammatory Bowel Disease and Colorectal Cancer", Seminars in Cancer Biology, 2013, pp. 1-10, Elsevier Ltd.
Lofland, D., et al., "Fecal Transplant for Recurrent Clostridium difficile Infection", Clin Lab Sci., 2013, 26(3):131-5.
Lopetuso, L.R., et al., "Commensal Clostridia: leading players in the maintenance of gut hemostasis", Gut Pathogens, 2013, 5:23 (8 pgs.).
Louie, T., et al., "Fidaxomicin Preserves the Intestinal Microbiome During and After Treatment of Clostridium difficile Infection (CDI) and Reduces Both Toxin Reexpression and Recurrence of CDI", Clinical Infectious Diseases, vol. 55, Suppl. 2, 2012, pp. S132-S142, Oxford University Press on behalf of the Infectious Diseases Society of America.
Lo Vecchio, A., et al., "Fecal Microbiota Transplantation for Clostridium difficile Infection: Benefits and Barriers", Current Opinion Gastroenterology, vol. 30, 2013, pp. 1-7, Wolters Kluwer Health and Lippincott Williams & Wilkins.
Lowy, I., et al., "Treatment with Monoclonal Antibodies Against Clostridium difficile Toxins", The New England Journal of Medicine, vol. 362, No. 3, Jan. 21, 2010, pp. 197-205, Massachusetts Medical Society.
Lozupone, C., et al., Diversity, Stability and Resilience of the Human Gut Microbiota, Nature, vol. 489, Sep. 13, 2012, pp. 220-230, Macmillan Publishers Limited.
Lucado, J., et al., "Clostridium difficile Infections (CDI) in Hospital Stays, 2009", HCUP Statistical Brief #124, Jan. 2012. Agency for Healthcare Research and Quality, Rockville, MD http:www.hcup-us.ahrg.gove/reports/statbriefs/sb124.pdf, pp. 1-12.
Macfarland, L., et al., "Recurrent Clostridium Difficile Disease: Epidemiology and Clinical Characteristics", Infection Control and Hospital Epidemiology, vol. 20, No. 1, Jan. 1999, pp. 43-50, The University of Chicago Press.
MacNeal, W., et al., "The Fecal Bacteria of Healthy Men: Part II. Quantitative Culture Experiments", The Journal of Infectious Diseases, vol. 6, No. 5, Nov. 26, 1909, pp. 571-609, Oxford University Press.
Manges, A., et al, "Comparative Metagenomic Study of Alterations to the Intestinal Microbiota and Risk of Nosocomial Clostridum difficile-Associated Disease", Journal of Infectious Diseases, vol. 202, 2010, pp. 1877-1884, Infectious Diseases Society of America.
Marcille, J., "Fecal Microbiota Transplantation for Treating Recurrent Clostridium difficile Infection", Managed Care, Jun. 2013, pp. 18-19.
Martin, J., et al., "Clostridium difficile: biological therapies", Curr Opin Infect Dis., Oct. 2013; 26(5):454-60.
Martin-Dejardin, F., et al., "A way to follow the viability of encapsulated Bifidobacterium bifidum subjected to a freeze-drying process in order to target the colon: Interest off low cytometry", European Journal of Pharmaceutical Sciences, vol. 49, 2013, pp. 166-174, Elsevier B.V.

Martinez, I., et al., "Long-Term Temporal Analysis of the Human Fecal Microbiota Revealed a Stable Core of Dominant Bacterial Species", PLOS One, vol. 8, Issue 7, Jul. 2013, pp. 1-12.
Martinez, J.A., et al., "Role of dietary polyphenols and inflammatory processes on disease progression mediated by the gut microbiota", Rejuvenation Res., Oct. 2013; 16(5):435-7.
Mattila, E., et al., "Fecal Transplantation, Though Colonoscopy, is Effective Therapy for Recurrent Clostridium Difficile Infection", Gastroenterology, vol. 142, 2012, pp. 490-496, AGA Institute.
Maturin, L., et al., "Bacterial Analytical Manual Chapter 3: Aerobic Plate Count", U.S. Department of Health and Human Services, Jan. 2001, pp. 1-6.
Maukonen, J., et al., "The Currently Used Commercial DNA-Extraction Methods give Different Results of Clostridium and Antinobacterial Populations Derived from Human Fecal Samples", FEMS Microbiology Ecology, vol. 79, 2012, pp. 697-708, Blackwell Publishing Ltd.
McCune, V.L., et al., "Faecal transplantation for the treatment of Clostridium difficile infecton: a review", Int J Antimicrob Agents, Mar. 2014; 43(3):201-6.
McDonald, C., et al., "Clostridium difficile Infection in Patients Discharged from U.S. Short-Stay Hospitals, 1996-2003", Emerging Infectious Diseases, vol. 12, No. 3, Mar. 2006, pp. 409-415.
Mellow, M.H., et al., "Colonscopic Fecal Bacteriotherapy in the Treatment of Recurrent Clostridium Difficile Infection—Results and Follow-up", OSMA Journal, Mar. 2011, pp. 89-91.
Merlino, J., et al., "Evaluation of CHROMagar Orientation for Differentiation and Presumptive Identification of Gram Negative Bacilli and *Enterococcus* Species", Journal of Clinical Microbiology, vol. 34, No. 7, Jul. 1996, pp. 1788-1793, American Society of Microbiology.
Minot, S., et al., "Rapid Evolution of the Gut Virome", PNSA, vol. 110, No. 30, 2013, pp. 12450-12455.
Mitchell, B.G., et al., "The Prolongation of Length of Stay Because of Clostridium difficile Infection", American Journal of Infection Control, vol. 42, 2014, pp. 164-167, Elsevier.
Mitchell, M., "Determining Criticality—Process Parameters and Quality Attributes Part I: Criticality as a Continum", BioPharam, Dec. 1, 2013, (7 pgs.).
Mitchell, M., "Determining Criticality—Process Parameters and Quality Attributes Part II; Design of Experiments and Data-Driver Criticality", BioPharam, Jan. 1, 2014, (9 pgs.).
Moayyedi, P., et al., "Canadian Association of Gastroenterology position statement: Fecal microbiota transplant therapy", Can J Gastroeneterol Hepatol, vol. 28, No. 2, Feb. 2014 (3 pgs.).
Mole, B., "FDA gets to Grips with Faeces", Nature, vol. 498, Jun. 13, 2013, pp. 147-148, Macmillan Publishers Limited.
Momozawa, Y., et al., "Characterization of Bacteria in Biopsies of Colon and Stools by High Roughput Sequencing of the V2 Region of Bacterial 16S rRNA Gene in Human", PLOS One, vol. 6, Issue 2, Feb. 2011, pp. 1-10.
Moore, W.E.C., et al., "Human Fecal Flora: The Normal Flora for 20 Japanese-Hawaiians", Applied and Environmental Microbiology, vol. 27, No. 5, May 1974, pp. 961-979, American Society of Microbiology.
Moschen, A., et al., "Dietary Factors: Major Regulators of the Gut's Microbiota", Gut and Liver, vol. 6, No. 4, Oct. 2012, pp. 411-416.
Mukhopadhyay, S., et al., "Manganese Blocks Intracellular Trafficking of Shiga Toxin and Protects Against Shiga Toxicosis", Science, vol. 335, Jan. 20, 2012, pp. 332-335.
Multiple Pharmacy Companies, "Rare Diseases: A Report on Orphan Drugs in the Pipeline", Medicines in Development, 2013, pp. 1-56.
Teather, R., "Maintenance of Laboratory Strains of Obligaetly Anaerobic Rumen Bacteria", Applied and Environmental Microbiology, vol. 44, No. 2, Aug. 1982, pp. 499-501.
Tedeschi, R., et al., "Collection and Preservation of Microorganisms", Methods in Molecular Biology, vol. 675, 2011, pp. 313-326, Springer Science + Business Media, LLC.
Tickler, I.A., et al., "Strain Types and Antimicrobial Resistance Patterns of Clostridium difficile Isolates from the United States: 2011-2013", Antimicrob Agents Chemother, Apr. 21, 2014 (17 pgs.).

(56) References Cited

OTHER PUBLICATIONS

Tjellstrom, B., et al., "Effect of Exclusive Enteral Nutrition on Gut Microflora Function in Children with Chron's Disease", Scandinavian Journal of Gastroenterology, vol. 47, 2012, pp. 1454-1459, Informa Healthcare.
Tottey, W., et al., "The Human Gut Chip "HuGChip", an Explorative Phylogenic Microarray for Determining Gut Microbiome Diversity at Family Level", PLOS One, vol. 8, Issue 5, May 2013, pp. 1-12.
Tran, M.C., et al., "Therapy of Clostridium difficile infection: perspectives on a changing paradigm", Expert Opin Pharmacother., Dec. 2013; 14(17):2375-86.
Tsai, S., et al., "Hyaluronan-Cisplatin Conjugate Nanoparticles Embedded in Eudragit S100-Coated Pencin/Alginate Microbeads for Colon Drug Delivery", International Journal of Nanomedicine, vol. 8, 2013, pp. 2399-2407, Dove Medical Press Ltd.
Tshudin-Sutter, S., et al., "Clostridium difficile: novel insights on an incessantly challenging disease", Curr Opin Infect Dis., Aug. 2012; 25(4):405-11.
Tvede, M., et al., "Bacteriotherapy for Chronic Relapsing Clostridium Difficile Diarrhea in Six Patients", The Lancet, May 27, 1989, pp. 1156-1160.
Tyler, A., et al., "Analyzing the Human Microbiome: A 'How to' guide for Physicians", Am J Gastroenterol, Apr. 22, 2014 (11 pgs.).
Udayappan, S.D., et al., "Intestinal microbiota and fecal transplantation as treatment modality for insulin resistance and type 2 diabetes mellitus", Clin Exp Immunol., Feb. 15, 2014 (17 pgs.).
Vaarala, O., "Human intestinal microbiota and type 1 diabetes", Curr Diab Rep., Oct. 2013; 13(5):601-7.
Vaishnavi, C., "Fecal microbiota transplantation for management of Clostridium difficile infection", Indian J Gastroenterol, Apr. 20, 2014 (7 pgs.).
Van den Abbeele, P., et al., "Prebiotics, Faecal Transplants and Microbial Network Units to Stimulate Biodiversity of the Human Gut Microbiome", Microbial Biotechnology, vol. 6, No. 4, 2013, pp. 335-340, John Wiley & Sons Ltd and Society for Applied Microbiology.
Van der Meulen, R., et al., "In Vitro Kinetic Analysis of Oligofructos Consumption by Bacteroides and Bifidobacterium SPP Indicates Different Degradation Mechanisms", Applied and Environmental Microbiology, vol. 72, No. 2, Feb. 2006, pp. 1006-1012, American Society for Microbiology.
Van der Wilden, G., et al., "Fulminant Clostridium difficile colitis: Prospective development of a risk scoring system", J Trauam Actue Care Surg., vol. 76, No. 2, 2014, 424-30.
Van Nood, E., et al., "Duodenal Infusion of Donor Feces for Recurrent Clostridium Difficile", The New England Journal of Medicine, vol. 368, No. 5, Jan. 31, 2013, pp. 407-415, Massachusetts Medical Society.
Van Nood, E., et al., "Fecal Microbiota Transplantation: Facts and Controversies", Current Opinion Gastroenterology, vol. 30, 2014, pp. 1-6, Lippincott Williams & Wilkins.
Van Nood, E., et al., "Struggling with Recurrent Clostridium Difficile Infections: Is Donor Faeces the Solution?", Eurosurveillance, vol. 14, Issue 34, Aug. 27, 2009, pp. 1-6.
Vandenplas, Y., et al., "Fecal Microbial Transplantation in a One-Year-Old Girl with Early Onset Colitis—Caution Advised", J Pediatr Gastroenterol Nutr., Jan. 2, 2014 (11 pgs.).
Varela, E., et al., "Colonisation by Faecalibacterium Prausnitzii and Maintenance of Clinical Remission in Patients with Ulcerative Colitis", Alimentary Pharmacology and Therapeutics, 2013, pp. 1-11, John Wiley & Sons Ltd.
Varkonyi, I., et al., "Findings of a hospital surveillance-based outcome evaluation study for Clostridium difficile-associated colitis", Clin Microbiol. Infect., Apr. 28, 2014 (18 pgs.).
Vartoukian, S., et al., "Strategies for culture of 'unculturable' bacteria", FEMS Microbiol Lett 309 (2010) 1-7.

Varum, F.J.O., et al., "A Novel Coating Concept for Ileo-Colonic Drug Targeting: Proof of Concept in Humans Using Scintigraphy", European Journal of Pharmaceutics and Biopharmaceutics, vol. 84, 2013, pp. 573-577, Elsevier B.V.
Viaud, S., et al., "Supplementary Materials for: The Intestinal Microbiota Modulates the Anticancer Immuni Effects of Cyclophosphamide", Science, vol. 342, Nov. 22, 2013, pp. 1-30.
Viaud, S., et al., "The Intestinal Microbiota Modulates the Anticancer Immuni Effects of Cyclophosphamide", Science, vol. 342, Nov. 22, 2013, pp. 971-976.
Vigsneas, L., et al., "Microbiotas from UC Patients Display Altered Metabolism and Reduced Ability of LAB to Colonize Mucus", Scientific Reports, vol. 3, 2012, pp. 1-10.
Vincent, C., et al., "Reductions in intestinal Clostridiales precede the development of nosocomial Clostridium difficile infection", Microbiome, 2013, 1:18 (11 pgs.).
Viswanathan, V., "The Meddling Microbes Midst Our Medicines", Gut Microbes, vol. 5, No. 4, Sep./Oct. 2013, pp. 1-2, Landes Bioscience.
Vrieze, A., et al., "Fecal Transplant: A Safe and Sustainable Clinical Therapy for Restoring Intestinal Microbial Balance in Human Disease?", Best Practice & Research Clinical Gastroenterology, vol. 27, 2013, pp. 127-137, Elsevier Ltd.
Vrieze, A., et al., "Transfer of Intestinal Microbiota from Lean Donors Increases Insulin Sensitivity in Individuals with Metabolic Syndrome", Gastroenterology, vol. 143, 2012, pp. 913-916, AGA Institute.
Vujkovic-Cvijin, I., et al., "Dysbiosis of the Gut Microbiota is Associated with HIV Disease Progression and Tryptophan Catabolism", Science Translation Medicine, vol. 5, Issue 193, Jul. 10, 2013, pp. 1-13, American Association for the Advancement of Science.
Vyas, D., et al., "Stool therapy May Become a Preferred Treatment of Recurrent Clostridium Difficile?", World Journal of Gastroenterology, vol. 19, Issue 29, Aug. 7, 2013, pp. 4635-4637, Baishideng.
Wang, W., et al., "Low Vitamin D Level is an Independent Predictor of Poor Outcomes in Clostridium difficile-Associated Diarrhea", Ther Adv Gastroenterol., 2014; 7(1):14-19.
Wasfy, M., et al., "Comparison of Preservation Media for Storage of Stool Samples", Journal of Clinical Microbiology, Aug. 1995, vol. 33, No. 8, pp. 2176-2178.
Weingarden, A., et al., "Microbiota Transplantation Restores Normal Fecal Bile Acid Composition in Recurrent Clostridium difficile Infection", Am J Physiol Gastrointest Liver Physiol, Nov. 27, 2013, pp. 1-30, American Physiology Society.
Weir, T., et al., "Stool Microbiome and Metabolome Differences Between Colorectal Cancer Patients and Healthy Adults", PLOS One, vol. 8, No. 8, Aug. 2013, pp. 1-10.
Wendt, J.M., et al., "Clostridium difficile Infection Among Children Across Diverse US Geographic Locations", Pediatrics, vol. 133, No. 4, Apr. 2014 (10 pgs.).
Wenfeng, S., et al., "Appraising Freeze-Drying for Storage of Bacteria and Their Ready Access in a Rapid Toxicity Assessment Assay", Appl Microbiol Biotechnol, 2013, pp. 1-10, Springer.
Wesemann, D., et al., "Microbial Colonization Influences Early B-Lineage Development in the Gut Lamina Propria", Nature, vol. 501, Sep. 5, 2013, pp. 112-116, Macmillan Publishers Limited.
Wiegand, P.N., et al., "Clinical and economic burden of Clostridium difficile infection in Europe: a systematic review of healthcare-facility-acquired infection", Journal of Hospital Infection 81 (2012) 1-14.
Wu, G.D., et al., "Analysis of the Human Gut Microbiome and Association with Disease", Clinical Gastroenterology and Hepatology, vol. 11, 2013, pp. 774-777, AGA Institute.
Wu, G. et al., "Linking Long-Term Dietary Patterns with Gut Microbial Enterotypes", Science, vol. 334, Oct. 7, 2011, pp. 1-9, American Association for the Advancement of Science.
Wu, N., et al., "Dysbiosis Signature of Fecal Microbiota in Colorectal Patients", Microb Ecol, 2013, pp. 1-9, Springer.
Wu, T., et al., "Gut microbiota dysbiosis and bacterial community assembly associated with cholesterol gallstones in large-scale study", BMC Genomics, vol. 14, No. 669, 2013, pp. 1-24.

(56) References Cited

OTHER PUBLICATIONS

Xu, Q., et al., "KGM and PMAA Based pH-Sensitive Interpenetrating Polymer Network Hydrogel for Controlled Drug Release", Carbohydrate Polymers, vol. 97, 2013, pp. 565-570, Elsevier Ltd.

Yoshimoto, S., et al., "Obesity Related, Obesity-Induced Gut Microbial Metabolite Promotes Liver Cancer Through Senescence Secretome", Nature, vol. 499, Jul. 4, 2013, pp. 97-103, Macmillan Publishers Limited.

Young, V., "The Intestinal Microbiota in Health and Disease", Current Opinion Gastroenterology, vol. 28, No. 1, Jan. 2012, pp. 63-69.

Youngster, I., et al., "Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014; 58(11):1515-22.

Youngster, I., et al., "Supplementary Appendix: Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014 (6 pgs.).

Zainah, H., et al., "Fecal Bacteriotherapy: A Case Report in an Immunossuppressed Patient with Ulcerative Colitis and Recurrent Clostridium difficile Infection", Case Reports in Infectious Diseases, 2012, pp. 1-2, Hindawi Publishing Corporation.

Zhang, F., et al., "Fecal Microbiota Transplantation for Severe Enterocolonic Fistulizing Crohn's Disease", World Journal of Gastroenterology, vol. 19, No. 42, Nov. 7, 2013, pp. 7213-7216, Baishideng Publishing Group Co., Limited.

Zhao, G., et al., "Effect of Protective Agents, Freezing Temperature, Rehydration Media on Viability of Malolactic Bacteria Subjected to Freeze-Drying", Journal of Applied Microbiology, vol. 99, 2005, pp. 333-338, The Society for Applied Microbiology.

Zhao, L., et al., "Targeting the Human Genome-Microbiome Axis for Drug Discovery: Inspirations from Global Systems Biology and Traditional Chinese Medicine", Journal of Proteome Research, vol. 11, 2012, pp. 3509-3519, American Chemical Society.

Zilberberg, M.D., et al., "Clostridium difficile Infections among Hospitalized Children, United States, 1997-2006", Emerging Infectious Diseases, vol. 16, No. 4, Apr. 2010, pp. 604-609.

Zilberberg, M.D., et al., "Development and Validation of a Recurrent Clostridium difficile Risk-Prediction Model", Journal of Hospital Medicine, Apr. 4, 2014 (6 pgs.).

Zimmer, C., "Bacterial Ecosystems Divide People Into 3 Groups, Scientists Say", The New York Times, Apr. 20, 2011 (4 pgs.).

Zoetendal, E., et al., "Mucosa-Associated Bacteria in the Human Gastrointestinal Tract are Uniformly Distributed Along the Colon and Differ from the Community Recovered from Feces", Applied and Environmental Microbiology, vol. 68, No. 7, Jul. 2002, pp. 3401-3407, American Society for Microbiology.

Franks, A., et al., "Variations of Bacterial Populations in Human Feces Measured by Fluorecent in Situ Hybridization with Group-Specific 16S rRNA-Targeted Oligonucleotide Probes", Applied and Environmental Microbiology, vol. 64, No. 9, Sep. 1998, pp. 3336-3345, American Society for Microbiology.

Frantzen, M., et al., "Empirical Evaluation of Preservation Methods foe Faecal DNA", Molecular Ecology, vol. 7, 1998, pp. 1423-1428, Blackwell Science Ltd.

Freeman, J., et al., "The Effects of Storage Conditions on Viability of Clostridium difficile Vegetative Cells and Spores and Toxin Activity in Human Faeces", Journal of Clinical Pathology, vol. 56, 2003, pp. 126-128.

Fridkin, S., et al., "Vital Signs: Improving Antibiotic Use Among Hospitalized Patients", MMWR, Mar. 7, 2014, vol. 63, No. 9, pp. 194-200.

Friedman, N.D., et al., "Prevalence of Clostridium difficile Colonization Among Healthcare Workers", BMC Infectious Diseases, vol. 13, No. 459, 2013, pp. 1-5.

Friedman-Moraco, R.J., et al., "Fecal Microbiota Transplantation for Refractory Clostridium difficile Colitis in Solid Organ Transplant Recipients", American Journal of Transplantation, vol. 14, 2014, pp. 477-480, The American Society of Transplantation and the American Society of Transplant Surgeons.

Gareau, M., et al., "Fluid and Electrolyte Secretion in the Inflamed Gut: Novel Targets for Treatment of Inflammation-Induced Diarrhea", Current Opinion in Pharmacology, vol. 13, 2013, pp. 1-5, Elsevier.

Gasol, J., et al., "Using Flow Cytometry for Counting Natural Planktonic Bacteria and Understanding the Structure of Planktonic Bacterial Communities", Scientia Marina, vol. 64, No. 2, Feb. 7, 2000, pp. 197-224.

Gerding, D.N., "Global Epidemiology of Clostridium difficile Infection in 2010", Infection Control and Hospital Epidemiology, 2010, vol. 31, No. S1, pp. S32,S34.

Gewolb, I., et al., "Stool Microflora in Extremely Low Birthweight Infants", Arch Dis Child Fetal Neonatal Ed, vol. 80, 1999, pp. F167-F173.

Giniatullina, A., et al., "Building for Big Pharma", Nature Biotechnology, 2013, pp. 1-4, Nature America, Inc.

Goodman, A., et al., "Extensive Personal Human Gut Microbiota Culture Collections Characterized and Manipulated in Gnotobiotic Mice", PNAS, vol. 108, No. 15, Apr. 12, 2011, pp. 6252-6257.

Gophna, U., "The Guts of Dietary Habits", Science, vol. 334, Oct. 7, 2011, pp. 45-46, AAAS.

Gomez-Simmons, A., et al., "Comparison of 3 Severity Criteria for Clostridium difficile Infection", Infection Control and Hospital Epidemiology, vol. 35, No. 2, Feb. 2014, pp. 196-199, The Society for Healthcare Epidemiology of America.

Gough, E., et al., "Systematic Review of Intestinal Microbiota Transplantation (Fecal Bacteriotherapy)for Recurrent Clostridium difficile Infection", Clinical Infectious Diseases, vol. 53, No. 10, Nov. 15, 2011, pp. 994-1002, Oxford University Press on behalf of the Infectious Diseases Society of America.

Gravitz, L., "The Critters Within", Nature, vol. 485, May 17, 2012, pp. s12-s13, Macmillan Publishers Limited.

Green, H., et al., "Impact of Freezing on the Future Utility of Archived Surveillance Culture Specimens", Infection Control and Hospital Epidemiology, vol. 28, No. 7, Jul. 2007, pp. 886-888.

Grzeskowiak, L., et al., "Distinct Gut Microbiota in Southeastern African and Northern European Infants", JPGN, vol. 54, No. 6, Jun. 2012, pp. 812-816.

Guarner, J., et al., "Correlation of the detection of Clostridium difficile toxins in stools and presence of the clostridia in tissues of children", Human Pathology (2010) 41, pp. 1586-1592.

Gueimonde, M., et al., "New Real-Time Quantitative PCR Procedure for Quantification of Bifidobacteria in Human Fecal Samples", Applied and Environmental Microbiology, vol. 70, No. 7, Jul. 2004, pp. 4165-4169, American Society for Microbiology.

Guerrero, D.M., et al., "Asymptomatic Carriage of Toxigenic Clostridium Difficile by Hospitalized Patients", Journal of Hospital Infection, 2013, pp. 1-4, Elsevier Ltd on behalf of the Healthcare Infection Society.

Guillemin, I., et al., "Patients' Experience and Perception of Hospital-Treated Clostridium difficile Infections: A Qualitative Study", Adis, 2014, pp. 1-9, Springer International Publishing Switzerland.

Guo, B., et al., "Systematic review: faecal transplantation for the treatment of Clostridium difficile-associated disease", Aliment Pharmacol. Ther. 2012; 35:865-875.

Gupta, A., et al., "Community-acquired Clostridium difficile infection: an increasing public health threat", Infection and Drug Resistance 2014:7 63-72.

Gupta, A., et al., "Design and Development of Liposomes for Colon Targeted Drug Delivery", Journal of Drug Targeting, vol. 21, No. 2, 2013, pp. 146-160, Informa UK, Ltd.

Gut Microbiome News, "Articles Highlight Advances, Potential Applications of Gut Microbiome Research", GenomeWeb, Jun. 6, 2012, pp. 1-3.

Gut Microbiome News, "Consortium Members Publish Collection of Studies Stemming from Human Micobiome Project", GenomeWeb, Jun. 13, 2012, pp. 1-4.

Gut Microbiome News, "Structure, Function and Diversity of the Healthy Human Microbiome", The Human Microbiome Consortium, vol. 486, Jun. 14, 2012, pp. 207-214, Macmillan Publishers Limited.

(56) References Cited

OTHER PUBLICATIONS

Gutierrez, R., et al., "Epidemiology of Clostridium difficile Infection among Active Duty United States Military Personnel (1998-2010)", BMC Infectious Diseases, vol. 13, No. 602, 2013, pp. 1-8.
Haines, R.B., "The Effect of Freezing on Bacteria", Proceedings of the Royal Society of London. Series B, Biological Sciences, vol. 124, No. 837, Jan. 14, 1938, pp. 451-463, The Royal Society.
Halabi, W., et al., "Clostridium Difficile Colitis in the United States: A Decade of Trends, Outcomes, Risk Factors for Colectomy, and Mortality After Colectomy", Journal of American College of Surgeons, 2013, pp. 1-11, Elsevier Inc.
Hamilton, M., et al., "High-Throughput DNA Sequence Analysis Reveals a Stable Engraftment of Gut Microbiota Following Transplantation of Previously Frozen Fecal Bacteria", Gut Microbes, vol. 4, No. 2, Mar./Apr. 2013, pp. 125-135, Landes Bioscience.
Hamilton, M., et al., "Preservation of Stock Cultures of Bacteria by Freezing and Drying", The American Journal of Gastroenterology, vol. 107, May 2012, pp. 761-767, American College of Gastroenterology.
Hansen, R., et al., "Microbiota of De-Novo Pediatric IBD: Increased Faecalibacterium Prausnitzii and Reduced Bacterial Diversity in Crohn's But Not in Ulcerative Colitis", American Journal of Gastroenterology, vol. 107, Oct. 9, 2012, pp. 1913-1922, American College of Gastroenterology.
Hao, W., et al., "Microflora of the Gastrointestinal Tract", Methods in Molecular Biology, vol. 268, 2004, pp. 491-502, Humana Press Inc., Totowa, NJ.
Harmsen, H.J. M., et al., "Comparison of Viable Cell Counts and Fluorescent in Situ Hybridization Using Specific rRNA-Based Probes for the Quantification of Human Fecal Bacteria", FEMS Microbiology Letters 183, 1999, pp. 125-129, Elsevier Science B.V., Federation of European Microbiological Societies.
Harpe, S.E., et al., "Characterization of Continued Antibacterial Therapy After Diagnosis of Hospital-Onset Clostridium difficile Infection: Implications for Antimicrobial Stewardship", Pharmacotherapy, vol. 32, No. 8, 2012, pp. 744-754.
Hawes, R.H., et al., "A concensus document on bowel preparation before colonoscopy: Prepared by a Task Force From the American Society of Colon and Rectal Surgeons (ASCRS), the American Society for Gastrointestinal Endoscopy (ASGE), and the Society of American Gastrointestinal and Endoscopic Surgeons (SAGES)", Gastrointestinal Endoscopy, vol. 63, No. 7, 2006, 894-910.
Hecht, G.A., et al., "What's the Value of an FDA IND for Fecal Microbiota Transplantation in Clostridium difficile Infection?", Clinical Gastroenterology and Hepatology, 2013, pp. 1-10.
Hennequin, C., et al., "GroEL (Hsp60) of Clostridium difficile is involved in cell adherence", Microbiology (2001), 147, 87-96.
Henning, T., "Polyethlene Glycols (PEGs) and the Pharmaceutical Industry", Fine, Specialty & Performance Chemicals, Jun. 2002, pp. 57-59.
Hensgen, M.P.M., et al., "Time interval of increased risk for Clostrium difficile infection after exposure to antibiotics", J Antimicrob Chemother 2012; 67:742-748.
Hill, M.J., et al., "The Normal Chronic Bacterial Flora", 1975, pp. 318-323.
HMPC, "Structure, Function and Diversity of the Healthy Human Microbiome", Nature, vol. 486, Jun. 14, 2012, pp. 207-214, Macmillan Publishers Limited.
Hoefman, S., et al., "Survival or Revival: Long-Term Preservation Induces a Reversible Viable but Non-Culturable State in Methane-Oxidizing Bacteria", PLOS One, vol. 7, Issue 4, Apr. 2012, pp. 1-9.
Hoffman, C., "The Human Intestinal Microbiome and Dietary Patterns", 2011, pp. 1-28, University of Pennsylvania.
Hoffmann, C., et al., "Archea and Fungi of the Human Gut Microbiome: Correlations with Diet and Bacterial Residents", PLOS One, vol. 8, Issue 6, Jun. 2013, pp. 1-12.
Holy, O., et al., "Oxygen Tolerance in Anaerobic Pathogenic Bacteria", Folia Microbiol, May 10, 2012, pp. 1-4, Institute of Microbiology, Academy of Sciences of the Czech Republic.

Honda, H., et al., "The Changing Epidemiology of Clostridium difficile Infection", Current Opinion, vol. 30, No. 1, Jan. 2014, pp. 54-62, Lippincott Williams & Wilkins.
Hoover, D., et al., "Transmission of Clostridium Difficile in Foods", Infect Dis Clin N Am. vol. 27, 2013, pp. 675-685, Elsevier Inc.
Cotta, M., et al., "Isolation, Characterization and Comparison of Bacteria from Swine Faeces and Manure Storage Pits", Environmental Microbiology, vol. 5, No. 9, Mar. 2003, pp. 737-745, Society for Applied Microbiology and Blackwell Publishing Ltd.
Counting Bacteria, "Live/Dead Baclight Bacterial Viability Kits", 2008.
Cox, L., et al., "Pathways in Microbe-Induced Obesity", Cell Metabolism, vol. 17, Jun. 4, 2013, pp. 883-894, Elsevier Inc.
Crook, D., et al., "Fidaxomin verses Vancomycin for Clostridium difficile Infection: Meta-Analysis of Pivotal Randomized Controlled Trials", Clinical Infectious Diseases, vol. 55, Suppl. 2, 2012, pp. S93-S103, Oxford University on behalf of the Infectious Diseases Society of America.
Curtin, C., "Researchers Examine the Genetic Diversity of the Human Gut Microbiome", Genome Web, Dec. 5, 2012, pp. 1-2.
D'Agostino, R.B., et al., "Risk Estimation for Recurrent Clostridium Difficile Infection Based on Clinical Factors", Clin. Infect Dis May 2014; 58(10):1386-93.
Dallas, K.B., et al., "Life after colectomy for fulminant Clostridium difficile colitis: a 7-year follow up study", The American Journal of Surgery (2014) 207, pp. 533-539.
Damman, C., et al., "The Microbiome and Inflammatory Bowel Disease: Is There a Therapeutic Role for Fecal Microbiota Transplantation?", The American Journal of Gastroenterology, vol. 107, Oct. 2012, pp. 1452-1459, nature publishing group.
Dan, M., et al., "Comparison of Preservation Media and Freezing Conditions for Storage of Specimens of Faeces", J. Med Microbiol., vol. 28, 1989, pp. 151-154, The Pathological Society of Great Britain and Ireland.
David, L., et al., "Diet Rapidly and Reproducibly Alters the Human Gut Microbiome", Nature, 2013, pp. 1-18, Macmillan Publishers Limited.
Davidovics, Z.H., et al., "Medical Stool: The Future Treatment of Inflammatory Bowel Disease?", JPGN, vol. 56, No. 6, Jun. 2013, p. 583, ESPGHAN and NASPGHAN.
Debast, S., et al., "European Society of Clinical Microbiology and Infectious Diseases (ESCMID): update of the treatment guidance document for Clostridium difficile infection (CDI)", 2013, pp. 1-88.
De Cruz, P., et al., "Characterization of the Gastrointestinal Microbiota in Health and Inflammatory Bowel Disease", Inflamm Bowel Dis, vol. 18, No. 2, Feb. 2012, pp. 372-390.
De Goffau, M., et al., "Fecal Microbiota Composition Differs Between Children with b-Cell Autoimmunity and Those Without", Diabetes, vol. 62, Apr. 2013, pp. 1238-1244, American Diabetes Association.
De Leon, L.M., et al., "Transient Flare of Ulcerative Colitis after Fecal Microbiota Transplantation for Recurrent Clostridium difficile Infection", Clinical Gastroenterology and Hepatology, vol. 11, 2013, pp. 1036-1038, AGA Institute.
Deshpande, A., et al., "Diagnostic Testing for Clostridium difficile Infection in Patients with Inflammatory Bowel Disease", 2013, p. 1.
Dethlefsen, L., et al., "Incomplete Recovery and Individualized Responses of the Human Distal Gut Microbiota to Repeated Antibiotic Perturbation", PNAS, vol. 108, Suppl. 1, Mar. 15, 2011, pp. 4554-4561.
De Vrieze, J., "The Promise of Poop", Science, vol. 341, Aug. 30, 2013, pp. 954-957, AAAS.
Deweerdt, S., "A complicated relationship status", Nature, Apr. 17, 2014; 508(7496):S61-3.
Dey, N., et al., "Association of Gut Microbiota with Post-Operative Clinical Course in Crohn's Disease", BMC Gastroenterology, vol. 13, No. 131, Aug. 2013, pp. 1-24.
Ding, T., et al., "Dynamics and associations of microbial community types across the human body", Nature, May 15, 2014; 509(7500):357-60.
Dixon, E., et al., "Solid-Phase Microextraction and the Human Fecal VOC Metabolome", PLOS One, vol. 6, Issue 4, Apr. 2011, pp. 1-9.

(56) References Cited

OTHER PUBLICATIONS

Dominguez, S.R., et al., "High Colonization Rate and Prolonged Shedding of Clostridium difficile in Pediatric Oncology Patients", Clin Infect Dis, Apr. 29, 2014 (11 pgs.).
Downing, N., et al., "Clinical Trial Evidence Supporting FDA Approval of Novel Therapeutic Agents", JAMA, vol. 311, No. 4, 2014, pp. 368-377, American Medical Association.
Dubberke, E.R., et al., "Burden of Clostridium difficile on the Healthcare System", CID 2012:55 (Suppl 2), S88-S92.
Dubberke, E., "Clostridium Difficile Infection: The Scope of the Problem", Journal of Hospital Medicine, vol. 7, Supp. 3, Mar. 2012, S1-S4.
Dubberke, E.R., et al., "The Ecology and Pathobiology of Clostridium Difficile Infections: An Interdisciplinary Challenge", 2001, pp. 1-31.
Dubela, K., et al., "Clostridium difficile Infection in Children Hospitalized due to Diarrhea", Eur J Clin Microbiol Infect Dis, vol. 33, 2014, pp. 201-209, Springer.
Duboc, H., et al., "Connecting Dysbiosis, Bile-Acid Dysmetabolism and Gut Inflammation in Inflammatory Bowel Diseases", Gut, vol. 62, 2013, pp. 531-539.
Duboc, H., et al., "Increase in Fecal Primary Bile Acids and Dysbiosis in Patients with Diarrhea-Predominant Irritable Bowel Syndrome", Neurogastroenterology & Motility, vol. 24, 2012, pp. 513-e247, Blackwell Publishing Ltd.
Dupont, H.L., "Diagnosis and Management of Clostridium difficile Infection", Clinical Gastroenerology and Hepatology, vol. 11, 2013, pp. 1216-1223, AGA Institute.
Dupont, H.L., "Review article: evidence for the role of gut microbiota in irritable bowel syndrome and its potential influence on therapeutic targets", Aliment Pharmacol Ther, May 2014; 39(10):1033-42.
Durban, A., et al., "Instability of the Faecal Microbiota in Diarrhoea-Predominant Irritable Bowel Syndrome", FEMS (Federation of European Microbiological Societies), 2013, pp. 1-9, John Wiley & Sons Ltd.
Durban, A., et al., "Structural Alterations of Faecal and Mucosa-Associated Bacterial Communities in Irritable Bowel Syndrome", Environmental Microbiology Reports, vol. 4, No. 2, 2012, pp. 242-247, Society for Applied Microbiology and Blackwell Publishing Ltd.
Dutta, S.K., et al., "Efficacy of Combined Jejunal and Colonic Fecal Microbiota Transplantation for Recurrent Clostridium difficile Infection", Clinical Gastroenerology and Hepatology, 2013, pp. 1-19.
Eckburg, P.B., et al., "Diversity of the Human Intestinal Microbial Flora", NIH (National Institutes of Health), Science, vol. 308, Jun. 10, 2005, pp. 1635-1638 (NIH pp. 1-8).
Ehlermann, P., et al., "Donor fecal transfer for recurrent Clostridium difficile-associated diarrhea in heart transplantation", The Journal of Heart and Lung Transplantation, vol. 33, No. 5, May 2014, pp. 551-553.
Eiseman, B., et al., "Fecal Enema as an Adjunct in the Treatment of Pseudomembranous Enterocolitis", Surgery, vol. 44, No. 5, Nov. 1958, pp. 854-859.
El Feghaly, R.E., et al., "Markers of Intestinal Inflammation, Not Bacerial Burden, Correlate With Clinical Outcomes in Clostridium difficile Infection", Clin Infect Dis. Jun. 2013; 56(12):1713-21.
Elixhauser, A., et al., "Readmissions following Hospitalizations with Clostridium difficile Infections, 2009", HCUP Statisical Brief #145, Dec. 2012, Agency for Healthcare Research and Quality, Rockville, MD, pp. 1-11.
Elliott, P., et al., "The UK Biobank Sample Handling and Storage Protocol for the Collection, Processing and Archiving of Human Blood and Urine", International Journal of Epidemiology, vol. 37, 2008, pp. 234-244, Oxford University Press on behalf of the International Epidemiological Association.
El-Matary, W., "Fecal Microbiots Transplantation: Long-Term Safety Issues", The American Journal of Gastroenterology, 2013, pp. 1537-1538, American College of Gastroenterology.
Eyre, D., et al., "Diverse Sources of C. difficile Infection Identified on Whole-Genome Sequencing", The New England Journal of Medicine, vol. 369, No. 13, Sep. 26, 2013, pp. 1195-1205, Massachusetts Medical Society.
Eyre, D., et al., "Predictors of First Recurrence of Clostridium Difficile Infection: Implications for Initial Management", Clinical Infectious Diseases, vol. 55, 2012, pp. 77-87, Oxford University Press on behalf of the Infectious Diseases Society of America.
Falony, G., et al., "Coculture Fermentations of Bifidobacterium Species and Bacteroides thetaiotaomicron Reveal a Mechanistic Insight into the Prebiotic Effect of Inulin-Type Fructans", Applied and Environmental Microbiology, vol. 75, No. 8, Apr. 2009, pp. 2312-2319, American Society for Microbiology.
Fava, F., et al., "Intestinal Microbiota in Inflammatory Bowel Disease: Friend or Foe?", World Journal of Gastroenterology, vol. 17, No. 5, Feb. 7, 2011, pp. 557-566, Baishideng.
Floch, M., "Fecal Bacteriotherapy, Fecal Transplant and the Microbiome", J Clin Gastroenterol, vol. 44, No. 8, Sep. 2010, pp. 529-530, Lippincott Williams & Wilkins.
Flores, R., et al., "Assessment of the Human Faecal Microbiota: II. Reproducibility and Associations of 16s rRNA Pyrosequences", European Journal of Clinical Investigation, vol. 42, 2012, pp. 855-863.
Food and Drug Administration, "Small Business Guide to FDA", 2011 (28 pgs.).
Fox, J., "Fecal Transplants to Follow FDA Rules", Nature Biotechnology, vol. 31, No. 7, Jul. 2013, p. 583, Nature America, Inc.
Hourigan, S.K., et al., "The Prevalence of Clostridium difficile Infection in Pediatric and Adults Patients with Inflammatory Bowel Disease", Dig Dis Sci May 1, 2014 DOI: 10.1007/s10620-0143169-4 (6 pgs.).
Hsiao, E., et al., "Microbiota Modulate Behavioral and Physiological Abnormalities Associated with Neurodevelopmental Disorders", Cell, vol. 155, Dec. 19, 2013, pp. 1-13, Elsevier Inc.
Hu, M.Y., et al., "Prospective Derivation and Validation of a Clinical Prediction Rule for Recurrent Clostridium difficile Infection", Gastroenterology 2009; 136:1206-1214.
Huang, Y., et al., "A Novel Plug-Controlled Colon-Specific Pulsatile Capsule with Tablet of Curcumin-Loaded SMEDDS", Carbohydrate Polymers, vol. 92, 2013, pp. 2218-2223, Elsevier Ltd.
Hubalek, Z., "Protectents Used in the Cryopreservation of Microorganisms", Cryobiology, vol. 46, 2003, pp. 225-229, Elsevier Science (USA).
Humphreys, D.P., et al., "Antibodies for the treatment of Clostridium difficile infection", Clin Vaccine Immunol. Apr. 30, 2014 doi:10.1128/CVI.00116-14 (35 pgs.).
Iida, N., et al., "Supplementary Materials for Commensal Bacteria Control Cancer Response to Therapy by Modulating the Tumor Microenvironment", Science, vol. 342, Nov. 22, 2013, pp. 1-38.
Jakobsson, H., et al., "Decreased Gut Microbiota Diversity, Delayed Bacteroidetes Colonisation ande Reduced Th1 Responses in Infants Delivered by Caesarean Section", Gut Online First, Aug. 7, 2013, pp. 1-10, BMJ Publishing Group Ltd.
Jakobsson, H., et al., "Short-Term Antibiotic Treatment Has Differing Long-Term Impacts on the Human Throat and Gut Microbiome", PLOS One, vol. 5, Issue 3, Mar. 2010, pp. 1-12.
Jansson, J., "Microbiota and Inflammatory Bowel Disease", PP Presentation, 2011, pp. 1-18.
Jeffery, I., et al., "An Irritable Bowel Syndrome Subtype Defined by Species-Specific Alterations in Faecal Microbiota", Gut, vol. 61, 2012, pp. 997-1006.
Jernburg, C., et al., "Long-Term ecological Impacts of Antibiotic Administration on the Human Intestinal Microbiota", The ISME Journal, vol. 1, 2007, pp. 56-66, International Society for Microbial Ecology.
Jiang, Z., et al., "Physician Attitudes Toward the use of Fecal Transplantation for Recurrent Clostridium difficile Infection in a Metropolitan Area", Clinical Infectious Diseases, vol. 56, Apr. 1, 2013, pp. 1059-1060, Oxford University Press on behalf of the Infectious Diseases Society of America.
Johnson, S. et al., "Fidaxomicin "Chaser" Regimen Following Vancomycin for Patients With Multiple Clostridium difficile Recurrences", Clin Infect Dis. Jan. 2013; 56(2):309-10.

(56) References Cited

OTHER PUBLICATIONS

Jones, A.M., et al., "Clostridium difficile: A European perspective", J Infect (2012), http://dx.doi.org/10.1016/j.jinf.2012.10.019, pp. 1-14.

Jump, R., et al., "Tigecycline Exhibits Inhibitory Activity against Clostridium difficile in the Colon of Mice and Does Not Promote Growth or Toxin Production", Antimicrobial Agents and Chemotherapy, vol. 55, No. 2, Feb. 2011, pp. 546-549, American Society for Microbiology.

Kaaskoush, N., et al., "Microbial Dysbiosis in Pediatric Patients with Crohn's Disease", Journal of Clinical Microbiology, vol. 50, No. 10, Oct. 2012, pp. 3258-3266, American Society for Microbiology.

Kahn, S., et al., "Colonoscopic Fecal Microbiota Transplant for Recurrent Clostridium difficile Infection in a Child", The American Journal of Gastroenterology, vol. 107, Dec. 2012, pp. 1930-1931, the American College of Gastroenterology.

Kahn, S. et al., "Fecal Bacteriotherapy for Ulcerative Colitis: Patients Are Ready, Are We?", Inflammatory Bowel Disease, vol. 18, No. 4, Apr. 2012, pp. 676-684.

Kao, D., et al., "Fecal Microbiota Transplantation Inducing Remission in Crohn's Colitis and the Associated Changes in Fecal Microbial Profile", J Clin Gastroenterol, 2014, PMID: 24667590 (4 pgs.).

Karadsheh, Z., et al., "Fecal Transplantationfor the Treatment of Recurrent Clostridium Difficile Infection", Northern American Journal of Medical Sciences, vol. 5, Issue 6, 2013, pp. 339-343.

Karlsson, F., et al., "Gut Metagenome in European Women with Normal, Impaired and Diabetic Glucose Control", Nature, vol. 498, Jun. 6, 2013, pp. 99-105, Macmillan Publishers Limited.

Karmali, S., et al., CAGS Clinical Practice Committee Report: The Science of Clostridium difficile and Surgery, Can J Surg, vol. 56, No. 6, Dec. 2013, pp. 367-371, Canadian Medical Association.

Kassam, Z., et al., "Fecal Microbiotia Transplantation of Clostridium Difficile Infection: Systematic Review and Meta-Analysis", American Journal of Gastroenterol, vol. 108, No. 4, 2013, pp. 500-508.

Kassam, Z., et al., "Fecal Transplant Via Retention Enema for Refractory or Recurrent Clostridium Difficile Infection", Arch Intern Med, vol. 172, No. 2, Jan. 23, 2012, pp. 191-193, American Medical Association.

Kassam, Z., et al., "Navigating Long-Term Safety in Fecal Microbiota Transplantation", The American Journal of Gastroenterology, vol. 108, Sep. 2013, p. 1538.

Keller, J.M., et al., "Clostridium difficile Infection in the Elderly", Clin Geriatr Med, vol. 30, 2014, pp. 79-93, Elsevier Inc.

Kellermeyer, R., "Prospects and Challenges for Intestinal Microbiome Therapy in Pediatric Gastrointestinal Disorders", World Journal of Gastrointestinal Pathophysiology (WJGP), vol. 4, No. 4, Nov. 15, 2013, pp. 91-93, Baishideng Publishing Group Co., Limited.

Kelly, C., "FDA's Role in Regulating FMT is Imperative", AGA Perspectives Online, Dec. 20, 2013, pp. 1-2.

Kelly, C., et al., "A How to Guide: Investigational New Drug Application of Fecal Microbiota Transplantation", Clinical Gastroenterology and Hepatology, 2013, pp. 1-40.

Kelson, J., et al., "The Gut Microbiota, Environment and Diseases of Modern Society", Gut Microbes, vol. 3, No. 4, Jul./Aug. 2012, pp. 374-382, Landes Bioscience.

Khanna, S., et al., "A Clinician's Primer on the Role of the Microbiome in Human Health and Disease", Mayo Clinic Proceedings, vol. 89, No. 1, Jan. 2014, pp. 107-114, Mayo Foundation for Medical Education and Research.

Khanna, S., et al., "Clostridium difficile infection: management strategies for a difficult disease", Ther Adv Gastroenterol 2014, vol. 7(2) 72-86.

Khortus, A., et al., "Changes in the Composition of the Human Fecal Microbiome After Bacteriotherapy for Recurrent Clostridium Difficile Associated Diahrrea", J Clin Gastroenterol, vol. 44, No. 5, May/Jun. 2010, pp. 354-360, Lippincott Williams & Wilkins.

Khortus, A.,et al., "Therapeutic Transplantation of the Distal Gut Microbiome", Nature Publishing Group, vol. 4, No. 1, Dec. 8, 2010, pp. 4-7.

Killgore, G., et al., "Comparison of Seven Techniques for Typing International Epidemic Strains of Clostridium difficile: Restriction Endonuclease Analysis, Pulsed-Field Gel Electrophoresis, PCR-Ribotyping, Multilocus Sequence Typing, Multilocus Variable—Number Tandem—Repeat Analysis, Amplified Fragment Length Polymorphism, and Surface Layer Protein A Gene Sequence Typing", Journal of Clinical Microbiology, vol. 46, No. 2, Feb. 2008, pp. 431-437, American Society of Microbiology.

Kim, B., et al., "Current Status and Future Promise of the Human Microbiome", Pediatric Gastroenerology, Hepatology & Nutrition (PGHN), vol. 16, No. 2, Jun. 2013, pp. 71-79, The Korean Society of Pediatric Gastroenerology, Hepatology & Nutrition.

Kim, J., "Editorial Commentary: 'High Colonization Rate and Prolonged Shedding of Clostridium difficile in Pediatric Oncology Patients'", Clinical Infectious Diseases Advance Access, 2014 (6 pgs.).

Kim, J., et al., "Epidemiological Features of Clostridium difficile-Associated Disease Among Inpatients at Children's Hospitals in the United States, 2001-2006", Pediatrics 2008; 122:1266-1270.

Klein, E.J., et al., "Diarrhea Etiology in a Children's Hospital Emergency Department: A Prospective Cohort Study", Clin Infect Dis., Oct. 1, 2006; 43(7):807-13.

Knetsch, C.W., et al., "Current Application and Future Perspectives of Molecular Typing Methods to Study Clostridium difficile Infections", Euro Surveillance, vol. 18, No. 4, Jan. 2013, pp. 1-11.

Koboziev, I., et al., "Role of the Enteric Microbiota in Intestinal Homeostasis and Inflammation", Free Radical Biology and Medicine, 2013, pp. 1-38.

Koeth, R., et al., "Intestinal Microbiota Metabolism of L-Carnitine, a Nutrient in Red Meat, Promotes Atherosclerosis", Nature Medicine, vol. 19, No. 5, May 2013, pp. 576-587, Nature America, Inc.

Konkel, L., "The Environmental Within: Exploring the Role of the Gut Microbiome in Health and Disease", Environmental Health Perspectives, vol. 121, No. 9, Sep. 2013, pp. A 276-A 281.

Konstantinov, S., et al., "Fecal Microbiota Transfer May Increase Irritable Bowel Syndrome and Inflammatory Bowel Diseases-Associated Bacteria", Gastroenterology, vol. 144, No. 4, Apr. 2013, pp. e19-e20.

Koote, R., et al., "The Therapeutic Potential of Manipulating Gut Microbiota in Obesity and Type 2 Diabetes Mellitus", Diabetes Obesity and Metabolism, vol. 14, 2012, pp. 112-120.

Korpela, K., et al., "Gut microbiota signatures predict host and microbiota responses to dietary interventions in obese individuals", PLOS One, Mar. 2014, vol. 9, Issue 3, e90702 (10 pgs.).

Kozak, G.K., et al., "Antimicrobial Resistance in *Escherichia coli* Isolates from Swine and Wild Small Mammals in the Proximity of Swine Farms and in Natural Environments in Ontario, Canada", Applied and Environmental Microbiology, vol. 75, No. 3, Feb. 2009, pp. 559-566, American Society for Microbiology.

Kristjansson, M., et al., "Comparison of Restriction Endonuclease Analysis, Bibotyping, and Pulsed-Field Gel Electrophoresis for Molecular Differentiation of Clostridium difficile Strains", Journal of Clinical Microbiology, vol. 32, No. 8, Aug. 1994, pp. 1963-1969, American Society for Microbiology.

Kuk, S., et al., "Stool Sample Storage Conditions for the Preservation of Giardia intestinalis DNA", Memorial Institute of Oswaldo Cruz, Rio de Janeiro, vol. 107, No. 8, Dec. 2012, pp. 965-968.

Munukka, E., et al., "Women With and Without Metabolic Disorder Differ in Their Gut Microbiota Composition", Obesity, vol. 20, No. 5, May 2012, pp. 1082-1087, Nature Publishing Group.

Murri, M., et al., "Gut Microbiota in Children with Type 1 Diabetes Differs from that in Healthy Children: A Case-Control Study", BMC Medicine, vol. 11, No. 46, 2013, pp. 1-12.

Nature Publishing Group, "Recent Patent Applications in Bacteriotherapy", Nature Biotechnology, vol. 31, No. 4, Apr. 2013, p. 318, Nature America, Inc.

Nagaro, K.J., et al., "Non-Toxigenic Clostridium difficile Protects Hamsters Against Challenge with Historic and Epidemic Toxigenic BI/NAP1/027 C. difficile", Antimicrob Agens Chemother. Nov. 2013; 57(11):5266-70.

(56) References Cited

OTHER PUBLICATIONS

Navidad, J., et al., "Evaluation of Luminex xTAG Gastrointestinal Pathogen Analyte Specific Reagents for High-Throughput, Simultaneous Detection of Bacteria, Viruses, and Parasites of Clinical and Public Health Importance", J Clin Microbiol, Jul. 2013, pp. 1-26, American Society for Microbiology.
Nieuwdorp, M., "Gut Microbiota Determine Insulin Sensitivity", Presentation, 2013, pp. 1-44.
Nitzan, O., et al., "Clostridium difficile and Inflammatory Bowel Disease: Role in Pathogenesis and Implications in Treatment", World Journal of Gastroenterology, vol. 19, Issue 43, Nov. 21, 2013, pp. 7577-7585, Baishideng Publishing Group, Inc.
Noverr, M., et al., "Does the Microbiota Regulate Immune Responses Outside the Gut", Trends in Microbiology, vol. 12, No. 12, Dec. 2004, pp. 562-568, Elsevier.
Numata, K., et al., "Silk-based delivery systems of bioactive molecules", Adv Drug Deilv Rev. Dec. 30, 2010; 62(15):1497-1508.
Nyangale, E., et al., "Gut Microbial Activity, Implications for Health and Disease: The Potential Role of Metabolite Analysis", Journal of Proteome Research, vol. 11, 2012, pp. 5573-5585, American Chemical Society.
Nylund, C.M., et al., "Clostridium difficile Infection in Hospitalized Children in the United States", Arch Pediatr Adolesc Med 2011;165(5):451-457.
O'Hara, A., et al., "The Gut Flora as a Forgotten Organ", EMBO Reports, vol. 7, No. 7, 2006, pp. 688-693, European Molecular Biology Organization.
Ohkusu, K., et al., "Cost-Effective and Rapid Presumptive Identification of Gram-Negative Bacilli in Routine Urine, Pus, and Stool Cultures: Evaluation of the Use of CHROMagar Orientation Medium in Conjunction with Simple Biochemical Tests", Journal of Clinical Microbiology, Dec. 2000, vol. 38, No. 12, p. 4586-4592.
O'Horo, J.C., "Treatment of Recurrent Clostridium difficile Infection: A Systematic Review", Infection, vol. 42, 2014, pp. 43-59, Springer.
Ohtake, S., et al., "Formation and Stabilization of Francisella tularensis Live Vaccine Strain", J Pharm Sci., vol. 100, No. 8, Aug. 2011, pp. 1-26, Wiley-Liss, Inc. and the American Pharmacists Association.
Oldfield, E.C., et al., "Clinical update for the diagnosis and treatment of Clostridium difficile infection", World J Gastrointest Pharacol Ther, Feb. 6, 2014; 5(1):1-26.
Olle, B., "Medicines for Microbiota", Nature Biotechnology, vol. 31, No. 4, Apr. 2013, pp. 309-315, Nature America, Inc.
Olson, M., et al., "Ten Years of Prospective Clostridium Difficile Associated DiseaseSurveillance and Treatment at the Minneapolis VA Medical Center", Infection Control and Hospital Epidemiology, vol. 15, No. 6, Jun. 1994, pp. 371-381, The University of Chicago Press.
Onneby, K., et al., "Effects of di- and polysaccharide formulations and storage conditions on survival of freeze-dried *Sphingobium* sp.", World J Microbiol Biotechnol, vol. 29, 2013, pp. 1399-1408, Springer Science+Business Media Dordrecht.
Onouchi, S., et al., "PCR-Based Assessment of the Recovery Rate of Exfoliated Colonocytes or Cancer Cells from Fecal Samples Depends on the Storage Conditions after Defecation", J Gastrointestin Liver Dis, vol. 16, No. 4, Dec. 2007, pp. 369-372.
Orenstein, R., et al., "Moving Fecal Microbiota Transplantation Into the Mainstream", Nutrition in Clinical Practice, vol. 28, No. 5, Oct. 2013, pp. 589-598, American Society for Parenteral and Enteral Nutrition.
O'Sullivan, O., et al., "Alterations in Intestinal Microbiota of Elderly Irish Subjects Post-Antibiotic Therapy", Journal of Antimicrobial Chemotherapy, vol. 68, 2013, pp. 214-221, Oxford University Press on behalf of the British Society of Antimicrobial Chemotherapy.
O'Toole, P.W., "Changes in the Intestinal Microbiota from Adulthood through Old Age", Clinical Microbiology & Infection, vol. 18, Suppl. 4, 2012, pp. 44-46, European Society of Clinical Microbiology and Infectious Diseases.
Ott, S., et al., "In Vitro Alterations of Intestinal Bacterial Microbiota in Fecal Samples through Storage", Diagnostic Microbiology & Infectious Disease, vol. 50, 2004, pp. 237-245, Elsevier.
Ott, S., et al., "Quantification of Intestinal Bacterial Populations by Real-Time PCR with a Universal Primer Set and Minor Groove Binder Probes: a Global Approach to the Enteric Flora", Journal of Clinical Microbiology, vol. 42, No. 6, Jun. 2004, pp. 2566-2572, American Society for Microbiology.
Owens, C., et al., "Fecal Microbiota Transplantation and Donor Standardization", Trends in Microbiology, vol. 21, No. 9, Sep. 2013, pp. 443-445.
Pamer, E.G., "Fecal Microbiota Transplantation: Effectiveness, Complexities, and Lingering Concerns", 2014, pp. 1-5, Nature Publishing Group.
Papa, E., et al., "Non-Invasive Mapping of the Gastrointestinal Microbiota Identifies Children with Inflammatory Bowel Disease", PLOS One, vol. 7, Issue 6, Jun. 2012, pp. 1-12.
Parekh, P.J., et al., "The role and influence of gut microbiota in pathogenesis and management of obesity and metabolic syndrome", Front Endocrinol (Lausanne), Apr. 7, 2014; 5:47 (7 pgs.).
Pascarella, F., et al., "Impact of Clostridium difficile infection on pediatric inflammatory bowel disease", J Pediatr. Jun. 2009; 154(6):854-8.
Patel, N., et al., "Fecal Microbiota Transplant for Recurrent Clostridium difficile Infection: Mayo Clinic in Arizona Experience", Mayo Clinic Proceedings, vol. 88, No. 8, Aug. 2013, pp. 799-805, Mayo Foundation for Medical Education and research.
Patel, L. N., et al., "Fecal Transplantation Therapy for Clostridium difficile-Associated Pouchitis", Int J Colorectal Dis, vol. 29, 2014, pp. 263-264, Springer.
Paterson, D., et al., "Putting Back the Bugs: Bacterial Treatment Relieves Chronic Diarrhea", The Medical Journal of Australia, vol. 160, Feb. 21, 1994, pp. 232-233.
Pathak, R., et al., "Treatment of Relapsing Clostridium difficile Infection using Fecal Microbiota Transplantation", Clinical and Experimental Gastroenterology, vol. 7, Dec. 27, 2013, pp. 1-7, DovePress.
Pennisi, E., "Cancer Therapies use a Little Help from Microbial Friends", Science, vol. 342, Nov. 22, 2013, p. 921, AAAS.
Perez-Chanona, E., et al., "From promotion to management: The wide impact of bacteria on cancer and its treatment", Bioessays, Apr. 22, 2014 (7 pgs.).
Peterson, B., et al., "Bacterial Cell Surface Damage due to Centrifugal Compaction", Applied and Environmental Microbiology, vol. 78, No. 1, Jan. 2012, pp. 120-125.
Petrof, E.O., et al., "From Stool Transplants to Next-Generation Microbiota Therapeutics", Gastroenterology, Jan. 6, 2014, pp. 1-29.
Pierce, K., "Physician Induced CRE Infections", 2014, Hardy Diagnostics (4 pgs.).
Pisano, R., et al., "Quality by Design: Scale-Up of Freeze-Drying Cycles in the Pharmaceutical Industry", AAPS, 2013, pp. 1-12, American Association of Pharmaceutical Sciences.
Planche, T.D., et al., "Differences in Outcome According to Clostridium difficile Testing Method: A Prospective Multicentre Diagnostic Validation Study of C difficile Infection", Lancet Infect Dis. Nov. 2013; 13(11):936-45.
Postgate, J.R., et al., "On the Survival of Frozen Bacteria", J. Gen. Microbiol., vol. 26, Feb. 9, 1961, pp. 367-378.
Pray, L., et al., "The Human Microbiome, Diet, and Health: Workshop Summary", The National Academies, 2012, pp. vi-D-3 (159), National Academy of Sciences, United States of America.
Preheim, S.P., et al., "Computational Methods for High-Throughput Comparative Analyses of Natural Microbial Communities", Methods Enzymol. 2013; 531:354-70.
Prideaux, L., et al., "Inflammatory Bowel Disease in Asia: A Systematic Review", Journal of Gastroenterology and Hepatology, vol. 27, 2012, pp. 1266-1280, Journal of Gastroenterology and Hepatology Foundation and Blackwell Publishing Asia Pty Ltd.
Proom, H., et al., "The Drying and Preservation of Bacterial Cultures", Mar. 10, 1948, pp. 7-18.
Qa'Dan, M., et al., "pH-induced conformational changes in Clostridium difficile toxin B", Infect Immun., May 2000; 68(5):2470-4.

(56) References Cited

OTHER PUBLICATIONS

Qin, J., et al., "A Metagenome-wide Association Study of Gut Microbiota in Type 2 Diabetes", Nature, vol. 490, Oct. 4, 2012, pp. 55-60, Macmillan Publishers Limited.
Rao, A., et al., "In Vitro Killing of Nosocomial Pathogens by Acid and Acidified Nitrite", Antimicrob. Agents Chemother. 2006, 50(11):3901-3904.
Rechner, P., et al., "Clinical Features of Clostridil Bacteremia: A Review from a Rural Area", Clinical Infectious Diseases, vol. 33, Aug. 1, 2001, pp. 349-353, Infectious Diseases Society of America.
Aas, J., et al., "Recurrent Clostridium Difficile Colitis: Case Series Involving 18 Patients Treated with Donor Stool Administered Via a Nasogastric Tube", Clinical Infectious Diseases, vol. 36, Mar. 1, 2003, pp. 580-585, Infectious Diseases Society of America.
Aas, J., et al., "Stool Transplantation for Older Patients with Clostridium Difficile Infection", JAGS, vol. 57, No. 12, Dec. 2009, pp. 2386-2387.
Abubaker, I., et al., "A systematic review of the clinical, public health and cost-effectiveness of rapid diagnostic tests for the detection and identification of bacterial intestinal pathogens in faeces and food", Health Technology Assessment, vol. 11, No. 36, Sep. 2007, pp. 1-230.
Abujamel, T., et al., "Defining the Vulnerable Period for Re-Establishment of Clostridium difficile Colonization after Treatment of C. difficile Infection with Oral Vancomycin or Metronidazole", PLOS One, vol. 8, Issue 10, Oct. 2013, pp. 1-12.
Acha, S.J., et al., "Changes of Viability and Composition of the *Escherichia Coli* Flora in Faecal Samples During Long Time Storage", Journal of Microbiological Methods, vol. 63, 2005, pp. 229-238, Elsevier B.V.
Adams, S., et al., "Ulcerative Colitis", American Family Physician, vol. 87, No. 10, 2013, pp. 699-705, American Academy of Family Physicians.
Adler, A., et al., "Trends and Changes in Clostridium difficile Diagnostic Profiles and Their Impact on the Proportion of Positive Samples: a National Survey", Clin. Microbiol Infect. Mar. 27, 2014, 10.1111/1469-0691.12634.
Agar Plate Info, "Anaerobic Bacteriology", 2007, pp. 4.0.1-4.14.2.
Agar Plate Info, BBL Bacteroides Bile Esculin Agar (BBE), 2006.
Agar Plate Info, BBL CDC Aneaerobe 5% Sheep Blood Agar, 2006.
Ali, S., "Diverse Sources of C. difficile Infection", New England Journal of Medicine, vol. 370, No. 2, Jan. 9, 2014, pp. 182-184, Massachusetts Medical Society.
Allen, S., et al., "Lactobacilli and bifi dobacteria in the prevention of antibiotic-associated diarrhoea and Clostridium difficile diarrhoea in older inpatients (PLACIDE): a randomised, double-blind, placebo-controlled, multicentre trial", The Lancet, Aug. 8, 2013, pp. 1-9.
Allen-Vercoe, E., et al., "A Canadian Working Group Report on Fecal Microbial Therapy: Microbial Ecosystems Therapeutics", Can J Gastroenterol, vol. 26, No. 7, Jul. 2012, pp. 457-462, Pulsus Group Inc.
Alonso, C., et al., Clostridium Difficile Infection Among Hematopoietic Stem Cell Transplant Recipients: Beyond Colitis, Current Opinion Infectious Diseases, vol. 26, No. 4, Aug. 2013, pp. 326-331, Lippincott Williams & Wilkins.
Alsharif, R., et al., "Bacterial Detection and Live/Dead Discrimination by Flow Cytometry", BD Biosciences, 2002, Becton, Dickinson and Company.
Amann, R.I., et al., "Combination of 16S rRNA-Targeted Oligonucleotide Probes with Flow Cytometry for Analyzing Mixed Microbial Populations", Applied and Environmental Microbiology, vol. 56, No. 6, Jun. 1990, pp. 1919-1925, American Society for Microbiology.
Ananthakrishnan, A., et al., "Genetic Risk Factors for Clostridium Difficile Infection in Ulcerative Colitis", Alimentary Pharmacology and Therapeutics, vol. 38, 2013, pp. 522-530, John Wiley & Sons LTD.

Andoh, A., et al., "Multicenter Analysis of Fecal Microbiota Profiles in Japanese Patients with Crohn's Disease", Journal of Gastroenterology, vol. 47, 2012, pp. 1298-1307, Springer.
Angelberger, S., et al., "Temporal Bacterial Community Dynamics Vary Among Ulcerative Colitis Patients after Fecal Microbiota Transplantation", American Journal of Gastroenterology, vol. 180, pp. 1620-1630, American College of Gastroenterology.
Arkkila, P.E., et al., "Fecal Bacteriotherapy for Recurrent Clostridium Difficile Infection", Gastroenterology Conference: Digestive Disease Week, May 2010, W.B. Saunders.
Aronoff, D.M., "Host-Pathogen Interactions in Clostridium difficile Infection: It Takes Two to Tango", Clin Infect Dis. (2014) 58 (10):1401-1403.
Arthur, J., et al., "The Struggle Within: Microbial Influences on Colorectal Cancer", Inflammatory Bowel Disease, vol. 17, No. 1, Jan. 2011, pp. 396-409, Crohn's and Colitis Foundation of America, Inc.
Arumugam, M., et al., "Enterotypes of the Human Gut Microbiome", Nature, 2011, pp. 1-7, Macmillan Publishers Limited.
Arvand, M., et al., "Increased incidence of Clostridium difficile PCR ribotype 027 in Hesse, Germany, 2011 to 2013", Euro Surveill, 2014:19(10) 1-6.
Aslam, S., et al., "Treatment of Clostridium Difficile-Associated Disease: Old Therapies and New Strategies", vol. 5, Sep. 2005, pp. 549-557.
Aspevall, O., et al., "Performance of Four Chromogenic Urine Culture Media after One or Two Days of Incubation Compared with Reference Media", Journal of Clinical Microbiology, vol. 40, No. 4, Apr. 2002, pp. 1500-1503.
ASTM International, "Standard Practice for Climatic Stressing of Packaging Systems for Single Parcel Delivery", Book of Standards vol. 15.10, 2010, 10.1520/F2825-10E01 (3 pgs.).
Atarashi, K. et al., "Introduction by a Rationally Selected Mixture of Clostridia Strains from the Human Microbiota", Nature, vol. 000, 2013, pp. 1-7, MacMillan Publishers Limited.
Austin, M., et al., "Fecal Microbiota Transplantation in the Treatment of Clostridium difficile Infections", The American Journal of Medicine (2014), doi: 10.1016/j.amjmed.2014.02.017 (15 pgs.).
Azad, M., et al., "Gut Microbiota of Healthy Canadian Infants: Profiles by Mode of Delivery and Infant Diet at 4 Months", Canadian Medical Association Journal (CMAJ), vol. 185, No. 5, Mar. 19, 2013, pp. 385-394, Canadian Medical Association.
Backhed, F., et al., "Host-Bacterial Mutualism in the Human Intestine", Science, vol. 307, Mar. 25, 2005, pp. 1915-1920.
Bahl, M.I., et al., "Freezing Fecal Samples Prior to DNA Extraction Affects the Firmicutes to Bacteroidetes Ratio Determined by Downstream Quantitative PCR Analysis", FEMS Microbiology Letters, vol. 329, 2012, pp. 193-197, Blackwell Publishing Ltd.
Bakken, J., et al., "Fecal Bacteriotherapy for Recurrent Clostridium difficile Infection", Anaerobe, vol. 15, Sep. 2009, pp. 285-289, Elsevier Ltd.
Bakken, J., et al., "Treating Clostridium Difficile Infection with Fecal Microbiota Transplantation", Clinical Gastroenterology and Hepatology, vol. 9, No. 12, Dec. 2011, pp. 1044-1049.
Bakken, J., et al., "Treatment Approaches Including Fecal Microbiota Transplantation for Recurrent Clostridium difficile Infection (RCDI) among Infectious Disease Physicians", Anaerobe, vol. 24, 2013, pp. 20-24, Elsevier Ltd.
Barbut, F., et al., "Does a Rapid Diagnosis of Clostridium difficile Infection Impact on Quality of Patient Management?", Clinical Microbiology and Infection, vol. 20, No. 2, Feb. 2013, pp. 136-144, European Society of Clinical Microbiology and Infectious Diseases.
Barletta, J., et al., "Proton Pump Inhibitors and the Risk for Hospital Acquired Clostridium Difficile Infection", Mayo Clinic Proc., 2013, pp. 1-6, Mayo Foundation for Medical Education and Research.
Baron, T., "Fecal Microbiota Transplant: We Know It's History, But Can We Predict It's Future?", Mayo Clinic Proc., vol. 88, No. 8, Aug. 2013, pp. 782-785, Mayo Foundation for Medical Education and Research.
Barr, D., "CGMPs in the Production of Clinical Supplies", RA Focus, Mar. 2007, pp. 46-48.
Bartlett, J., "A Call to Arms: The Imperative for Antimicrobial Stewardship", CID, 2011:53 (Suppl 1) S4-S7.

(56) References Cited

OTHER PUBLICATIONS

Bauer, M.P., et al., "Patients with Cystic Fibrosis have a High Carriage Rate of Non-Toxigenic Clostridium Difficile", Clinical Microbiology and Infection, 2013, pp. 1-4, European Society of Clinical Microbiology and Infectious Diseases.

BD, "Brucella Blood Agar with Hemin and Vitamin K1", BD, Sep. 2011, pp. 1-4.

Bell, C.H., "The Effects of Centrifugation and Filtration as Pre-Treatments in Bacterial Retention Studies", Jun. 2005, pp. 1-7.

Ben-Amor, K., et al., "Genetic Diversity of Viable, Injured and Dead Fecal Bacteria Assessed by Fluorecence-Activated cell Sorting and 16S rRNA Gene Analysis", Applied and Environmental Microbiology, vol. 71, No. 8, Aug. 2005, pp. 4679-4689, American Society for Microbiology.

Ben-Amor, K., et al., "Multiparametric Flow Cytometry and Cell Sorting for the Assessment of Viable, Injured, and Dead Bifidobacterium Cells During Bile Salt Stress", Applied and Environmental Microbiology, vol. 68, No. 11, Nov. 2002, pp. 5209-5216, American Society for Microbiology.

Benjamin, J.L., et al., "Smokers with Active Crohn's Disease Have a Clinically Relevant Dysbiosis of the Gastrointestinal Microbiota", Inflamm Bowel Dis, vol. 18, No. 6, Jun. 2012, pp. 1092-1100.

Bennett, J., et al., "Treatment of Ulcerative Colitis by Implantation of Normal Colonic Flora", The Lancet, Jan. 21, 1989, p. 164.

Bennett, P.S., et al., "What Nurses Need to Know About Fecal Microbiota Transplantation: Education, Assessment, and Care for Children and Young Adults", J. Pediatr Nurs., Feb. 7, 2014 doi: 10.1016/j.pedn.2014.01.013 (8 pgs).

Berejnov, V., et al., "Effects of Cryoprotectant Concentration and Cooling Rate on Vitrification of Aqueous Solutions", Journal of Applied Crystallography, vol. 39, 2006, pp. 1-14.

Bervoets, L., et al., "Differences in Gut Microbiota Composition Between Obese and Lean Children: a Cross-Sectional Study", Gut Pathogens, vol. 5, No. 10, 2013, pp. 1-10, BioMed Central Ltd.

Best, E., et al., "The Potential for Airborne Dispersal of Clostridium difficile from Symptomatic Patients", Clinical Infectious Diseases, vol. 50, No. 11, Jun. 1, 2010, pp. 1450-1457, Infectious Diseases Society of America.

Bhat, A., et al., "Bacillus Subtilis Natto: A Non-Toxic Source of Poly-γ-Glutamic Acid that could be used as a Cryoprotectant for Probiotic Bacteria", AMB Express, vol. 3, No. 36, 2013, pp. 1-9, Springer.

Bodger, K., et al., "Development and Validation of a Rapid, Generic Measure of Disease Control from the Patient's Perspective: The IBD-Control Questionnaire", Gut, vol. 0, Oct. 9, 2013, pp. 1-11, BMJ Publishing Group Ltd (& BSG).

Boenning, D.A., et al., "Clostridium difficile in a pediatric outpatient population", Pediatric Infectious Disease, vol. 1, No. 5, pp. 336-338.

Bonfrate, L., et al., "Microbiota in Health and Irritable Bowel Syndrome: Current Knowledge, Perspectives and Therapeutic Options", Scandinavian Journal of Gastroenterology, vol. 48, 2013, pp. 995-1009, Informa Healthcare.

Boone, J.H., et al., "Clostridium difficile prevalence rates in a large healthcare system stratified according to patient population, age, gender, and specimen consistency", Eur J Clin Microbiol Infect Dis (2012) 31:1551-1559.

Borody, T.J., et al., "Bacteriotherapy Using Fecal Flora", J Clin Gastroenterol, vol. 38, No. 6, Jul. 2004, pp. 475-483, Lippincott Williams & Wilkins.

Borody, T.J., et al., "Bowel-Flora Alteration: A Potential Cure for Inflammatory Bowel Disease and Irritable Bowel Syndrome?", The Medical Journal of Australia, vol. 150, May 15, 1989, p. 604.

Borody, T.J., et al., "Fecal Microbiota Transplantation: Indications, Methods, Evidence, and Future Directions", Curr Gastroenterol Rep, vol. 15, No. 337, Jul. 14, 2013, pp. 1-7, Springer.

Borody, T.J., et al., "Therapeutic Faecal Microbiota Transplantation: Current Status and Future Developments", Current Opinion, vol. 30, No. 1, Jan. 2013, pp. 97-105, Lippincott Williams & Wilkins.

Borody, T.J., et al., "Treatment of Ulcerative Colitis Using fecal Bacteriotherapy", J Clin Gastroenterol, vol. 37, No. 1, 2003, pp. 42-47, Lippincott Williams & Wilkins.

Bowden, T., et al., "Pseudomembranous Enterocolitis: Mechanism of Restoring Floral Homeostasis", The American Surgeon, No. 4, Apr. 1981, pp. 178-183, J. R. Lippincott Company.

Brace, C., et al., "Microbial composition analysis of Clostridium difficile infections in an ulcerative colitis patient treated with multiple fecal microbiota transplantations", J Crohns Colitis (2014), http://dx.doi.org/10.1016/j. crohns.2014.01.020 (5 pgs.).

Brahe, L.K., et al., "Is Butyrate the Link Between Diet, Intestinal Microbiota and Obesity-Related Metabolic Diseases?", Obesity reviews, 2013, pp. 1-10, International Association for the Study of Obesity.

Brandt, L. et al., "American Journal of Gastroenterology Lecture: Intestinal Microbiota and the Role of Fecal Microbiota Transplant (FMT) in Treatment of C Diff Infection", The American Journal of Gastroenterology, vol. 108, Jan. 15, 2013, pp. 177-185, American College of Gastroenterology.

Brandt, L., et al., "An Overview of Fecal Microbiota Transplantation: Techniques, Indications and Outcomes", Gastrointestinal Endoscopy, vol. 78, No. 2, 2013, pp. 240-249, American Society for Gastrointestinal Endoscopy.

Brandt, L., et al., "Long-Term Follow-Up of Colonoscopic Fecal Microbiota Transplant for Recurrent Clostridium Difficile Infection", The American Journal of Gastroenterology, vol. 107, Mar. 27, 2012, pp. 1079-1087, American College of Gastroenterology.

Brandt, L., et al., "Norovirus Gastroenteritis After Fecal Microbiota Transplantation for Treatment of Clostridium difficile Infection Despite Asymptomatic Donors and Lack of Sick Contacts", The American Journal of Gastroenterology, vol. 108, Aug. 2013, pp. 1367-1368, American College of Gastroenterology.

Brecher, S., et al., "Laboratory Diagnosis of Clostridium Difficile Infections: A Practical Guide for Clinicians: There is a Light at the End of the Colon", Clinical Infectious Diseases, Jun. 20, 2013, pp. 1-25, Oxford University Press on behalf of the Infectious Diseases Society.

Britton, R., et al., "Role of the Intestinal Microbiota in Resistance to Colonization by Clostridium difficile", Gastroenterology, 2014, pp. 1-19.

Brown, J., et al., "Translating the Human Microbiome", Nature Biotechnology, vol. 31, No. 4, Apr. 2013, pp. 304-308, Nature America, Inc.

Buffie, C., et al., "Microbiota-Mediated Colonization Resistance against Intestinal Pathogens", Nature Reviews Immunology, 2013, pp. 1-12, Macmillan Publishers Limited.

Burke, K., et al., "Fecal Transplantation for Recurrent Clostridium Difficile Infection in Older Adults: A Review", JAGS, vol. 61, 2013, pp. 1394-1398, The American Geriatrics Society.

Burnham, C.,et al., "Diagnosis of Clostridium Difficile Infection: An Ongoing Conundrum for Clinicians and Clinical Laboratories", Clinical Microbiology Reviews, vol. 26, No. 3, Jul. 2013, pp. 604-630, American Society for Microbiology.

Calabrese, R., et al., "Finding Common Ground with ISO 9001 and FDA Good Manufacturing Practices", Quality Digest Magazine, Nov. 7, 2013, pp. 1-5, QCI International.

Cammarota, G., et al. "Fecal Microbiota Transplantation for the Treatment of Clostridium difficile Infection: A Systematic Review", Journal of Clinical Gastroenterology, 2014, pp. 1-10, Lippincott Williams & Wilkins.

Cammarota, G., et al. "Fecal Transplantation for Clostridium difficile Infection. Three Cases Treated in Italy", Digestive and Liver Disease, 2014, p. 1, Elsevier Ltd.

Cammarota, G., et al., "Gut microbiota modulation: probiotics, antibiotics or fecal microbiota transplantation?" Intern Emerg Med (2014), DOI: 10.1007/s11739-014-069-4 (9 pgs.).

Cardona, S., et al., "Storage Conditions of Intestinal Microbiota Matter in Metagenomic Analysis", BMC Microbiology, vol. 12, No. 158, 2012, pp. 1-8, BioMed Central Ltd.

Carroll, I., et al., "Characterization of the Fecal Microbiota Using High-Throughput Sequencing Reveals a Stable Microbial Community During Storage", PLOS One, vol. 7, Issue 10, Oct. 2012, pp. 1-7.

(56) References Cited

OTHER PUBLICATIONS

CDC, "Antibiotic Resistance Threats in the United States, 2013", Center for Disease Control (CDC), 2013, pp. 1-114.
CDC, "Vital Signs: Preventing Clostridium difficile Infections", MMWR, Mar. 9, 2012, vol. 61, No. 9, 157-162.
Chandel, N., et al., "The Good and the Bad of Antibiotics", Focus, vol. 5, Issue 192, Jul. 3, 2013, pp. 1-3.
Chang, J., et al., "Decreased Diversity of the Fecal Microbiome in Recurrent Clostridium Difficile-Associated Diarrhea", The Journal of Infectious Diseases, Feb. 1, 2008, pp. 435-441, Infectious Diseases Society of America.
Chassard, C., et al., "Functional Dysbiosis within the Gut Microbiota of Patients with Constipated-Irritable Bowel Syndrome", Alimentary Pharmacology and Therapeutics, vol. 35, 2012, pp. 828-838, Blackwell Publishing Ltd.
Chavarri, M., et al., "Microencapsulation of a Probiotic and Prebiotic in Alginate-Chitosan Capsules Improves Survival in Simulated Gastro-Intestinal Conditions", International Journal of Food Microbiology, vol. 142, 2010, pp. 185-189, Elsevier B.V.
Chilton, C.H., et al., "Successful Treatment of Simulated Clostridium difficile Infection in a Human Gut Model by Fidaxomin First Line and after Vancomycin or Metronidazole Failure", Journal of Antimicrobial Chemotherapy, vol. 69, 2014, pp. 451-462, Oxford University Press on behalf of the British Society for Antimicrobial Chemotherapy.
Chisti, Y., "Hydrodynamic Damage to Animal Cells", Critical Reviews in Biotechnology, 21(2):67-110 (2001).
Chitnis, A., et al., "Epidemiology of Community-Associated Clostridium Difficile Infection, 2009 Through 2011", Jama Intern Med, Jun. 17, 2013, pp. E1-E9, American Medical Association.
Clabots, C., et al., "Development of a Rapid and Efficient Restriction Endonuclease Analysis Typing System for Clostridium difficile and Correlation with Other Typing Systems", Journal of Clinical Microbiology, vol. 31, No. 7, Jul. 1993, pp. 1870-1875, American Society for Microbiology.
Clarke, S., et al., "The Gut Microbiota and its Relationship to Diet and Obesity", Gut Microbes, vol. 3, Issue 3, May/Jun. 2012, pp. 186-202, Landes Bioscience.
Claas, E., et al., "Performance of the xTAGR Gastrointestinal Pathogen Panel, a Multiplex Molecular Assay for Simultaneous Detection of Bacterial, Viral, and Parasitic Causes of Infectious Gastroenteritis", J. Microbiol. Biotechnol., vol. 23, No. 7, Jul. 2013, pp. 1041-1045, The Korean Society for Microbiology and Biotechnology.
Clemente, J., et al., "The Impact of the Gut Microbiota on Human Health: An Integrative View", Cell, vol. 148, Mar. 16, 2012, pp. 1258-1270, Elsevier Inc.
Cnops, L., et al., "Freezing of stool samples improves real-time PCR detection of Entamoeba dispar and Entamoeba histolytica", Journal of Microbiological Methods, vol. 80, 2010, pp. 310-312, Elsevier Inc.
Cody, W., et al., "Skim Milk Enhances the Preservation of Thawed −80° C Bacterial Stocks", J Microbial Methods, vol. 75, No. 1, Sep. 2008, pp. 135-138.
Cohen, S.H., et al., "Clinical Practice Guidelines for Clostridium difficile Infection in Adults: 2010 Update by the Society for Healthcare Epidemiology of America (SHEA) and the Infectious Diseases Society of America (IDSA)", Infection Control and Hospital Epidemiology, vol. 31, No. 5 (May 2010), pp. 431-455.
Collins, D., "Pseudomembranous Enterocolitis—Further Observations on the Value of Donor Fecal Enemata as an Adjunct in the Treatment of Pseudomembranous Enterocolitis", Journal of Proctology, vol. 11, No. 5, Oct. 1960, pp. 389-391.
Collins, S., et al., "The Adoptive Transfer of Behavioral Phenotype Via the Intestinal Microbiota: Experimental Evidence and Clinical Implications", Current Opinion in Microbiology, vol. 16, 2013, pp. 1-6, Elsevier B.V.
Comito, D., et al., "Dysbiosis in the Pathogenesis of Pediatric Inflammatory Bowel Diseases", International Journal of Inflammation, 2012, pp. 1-7, Hindawi Publishing Corporation.
Coteur, G., et al., "Evaluation of the meaningfulness of health-related quality of life improvements as assessed by the SF-36 and the EQ-5D VAS in patients with active Crohn's disease", Aliment Pharmacol Ther 29, (2009) 2032-1041.
Reynolds, J., "Serial Dilution Protocols", Microbe Library, Mar. 29, 2012, pp. 1-4, American Society for Microbiology.
Ridaura, V., et al., "Gut Microbiota from Twins Discordant for Obesity Modulate Metabolism in Mice", Science, vol. 341, Sep. 6, 2013, pp. 1079, 1241214-1-1241214-10, American Association for the Advancement of Science.
Ridlon, J., et al., "Cirrhosis, bile acids and gut microbiota", Gut Microbes, vol. 4, No. 5, Sep./Oct. 2013, pp. 1-6, Landes Bioscience.
Ringel, Y., et al., "The Intestinal Microbiota and Immune Function in the Pathogenesis of Irritable Bowel Syndrome", Am J Physiol Gastrointest Liver Physiol, Oct. 15, 2013; 305(8):G529-41.
Rinttila, T., et al., "Development of an Extensive set of 16S rDNA-Targeted Primers for Quantification of Pathogenic and Indigenous Bacteria in Faecal Samples by Real-Time PCR", Journal of Applied Microbiology, vol. 97, 2004, pp. 1166-1177, The Society for Applied Microbiology.
Roesch, L., et al., "Influence of Fecal Sample Storage on Bacterial Community Diversity", The Open Microbiology Journal, vol. 3, 2009, pp. 40-46.
Rogler, G., et al., "The heart and the gut", Eur Heart J, Feb. 2014; 35(7):426-30.
Rohlke, F., et al., "Fecal microbiota transplantation in relapsing Colostridium difficile infection", Therap Adv Gastroenterol., Nov. 2012; 5(6):403-20.
Rolfe, R., et al., "Bacterial Interference Between Clostridium Difficile and Normal Fecal Flora", The Journal of Infectious Diseases, vol. 143, No. 3, Mar. 1981, pp. 470-475, Oxford University Press.
Rubin, D., "Curbing our Enthusiasm for Fecal Transplantation in Ulcerative Colitis", The American Journal of Gastroenterology, vol. 108, 2013, pp. 1631-1633, nature publishing group.
Rubin, D., et al., "Chronic Intestinal Inflammation: Inflammatory Bowel Disease and Colitis-Associated Colon Cancer", Frontiers in Immunology, vol. 3, Article 107, May 2012, pp. 1-10.
Rubin, T.A., et al., "Fecal microbiome transplantation for recurrent Clostridium difficile infection: Report on a case series", Anaerobe 19 (2013) 22-26.
Russell, G., et al., "Fecal Bacteriotherapy for Relapsing Clostridium difficile Infection in a Child: A Proposed Treatment Protocol", Pediatrics, vol. 126, No. 1, Jul. 2010, pp. e239-e242, American Academy of Pediatrics.
Safdar, N., "Clostridium difficile: The Emerging Epidemic", Mayo Clinic Proceedings, Nov. 2012, vol. 87, No. 11, 1037-1039.
Sandora, T.J., et al., "Epidemiology and risk factors for Clostridium difficile infection in children", Pediatr Infect Dis J, Jul. 2011; 30(7):580-4.
Saulnier, D., et al., "Gastrointestinal Microbiome Signatures of Pediatric Patients with Irritable Bowel Syndrome", Gastroenterology, vol. 141, No. 5, Nov. 2011, pp. 1782-1791, AGA Institute.
Savani, M., et al., "Pilot-Scale Production and Viability Analysis of Freeze-Dried Probiotic Bacteria Using Different Protective Agents", Nutrients, vol. 2, 2010, pp. 330-339.
Schloissnig, S., et al., Geniomic Variation Landscape of the Human Gut Microbiome, Nature, vol. 493, Jan. 3, 2013, pp. 45-50, Macmillan Publishers Limited.
Schwan, A., et al., "Relapsing Clostridium Difficile Enterocolitis Cure by Rectal Infusions of Normal Feces", Scand J Infect Dis, vol. 16, 1984, pp. 211-215.
Schwartz, K., et al., "Severe clinical outcome is uncommon in Clostridium difficile infection in children: a retrospective cohort study", BMC Pediatr, Jan. 31, 2014; 14:28 (6 pgs.).
Schwartz, M., et al., "Norovirus Gastroenteritis After Fecal Microbiota Transplantation for Treatment of Clostridium Difficile Infection Despite Asymptomatic Donors and Lack of Sick Contacts", American Journal of Gastroenterology, vol. 108, Aug. 2013, pp. 1367-1368, American College of Gastroenterology.
See, I., et al., "NAP1 Strain Type Predicts Outcome From Clostridium difficile Infection", Clin Infect Dis, May 2014; 58(10):1394-400.

(56) References Cited

OTHER PUBLICATIONS

Segata, N., et al., "Composition of the Adult Digestive Tract Bacterial Microbiome Based on Seven Mouth Surfaces, Tonsils, Throat and Stool Samples", Genome Biology, vol. 13, 2012, pp. 1-18, BioMed Central Ltd.
Senior, K., "Faecal transplantation for recurrent C difficile diarrhoea", Lancet Infect Dis., Mar. 2013; 13(3):200-1.
Sha, S. et al., "Systematic review: faecal microbiota transplantation therapy for digestive and nondigestive disorders in adults and children", Aliment Pharmacol Ther, May 2014; 39(10):1003-32.
Shamekhi, F., et al., "Cell Viability of Microencapsulated *Bifidobacterium animalis* Subsp. Lactis Under Freeze-Drying, Storage and Gastrointestinal Tract Simulation Conditions", Folia Microbiol, vol. 58, 2013, pp. 91-101, Springer.
Shaughnessy, M.K., et al., "Unnecessary Antimicrobial Use in Patients With Current or Recent Clostridium difficile Infection", Infect Control Hosp Epidemiol 2013;34(2):109-116.
Shim, J.O., "Gut Microbiota in Inflammatory Bowel Disease", Pediatric Gastroenterology, Hepatology & Nutrition (PGHN), vol. 16, No. 1, Mar. 2013, pp. 17-21, The Korean Society of Pediatric Gastroenterology, Hepatology & Nutrition.
Silverman, M., et al., Success of Self-Administered Home Fecal Transplantation for Chronic Clostridium Difficile Infection, Clinical Gastroenterology and Hepatology, vol. 8, No. 5, 2010, pp. 471-473, AGA Institute.
Simoes, C., et al, "Habitual Dietary Intake is Associated with Stool Microbiota Composition in Monozygotic Twins", The Journal of Nutrition, 2013, pp. 417-423, American Society for Nutrition.
Simon, M. S., "Cost-Effectiveness of Fidaxomicin for Clostridium difficile Treatment", Clinical Infectious Diseases, vol. 58, No. 4, 2014, p. 604, Oxford University Press on behalf of the Infectious Diseases Society of America.
Smith, M.B., et al., "Policy: How to regulate faecal transplants", Nature, Feb. 20, 2014; 506(7488):290-1.
Sobhani, I., et al., "Microbial Dysbiosis and Colon Carcinogenesis: Could Colon Cancer be Considered a Bacteria-Related Disease?", Therapeutic Advances in Gastroenterology, vol. 6, No. 3, 2013, pp. 215-229.
Sofi, A. et al., "Physician outlook toward fecal microbiota transplantation in the treatment of Clostridium difficile infection", Am J Gastroenterol, Oct. 2013; 108(10):1661-2.
Sokol, H., et al., Low Counts of Faecalibacterium Prausnitzii in Colitis Microbiota, Inflamm Bowel Dis, vol. 15, No. 8, Aug. 2009, pp. 1183-1189, Crohn's & Colitis Foundation of America, Inc.
Solari, P., et al., "Tempered enthusiasm for Fecal transplantation", Clin Infect Dis, Apr. 23, 2014 (3 pgs.).
Song, Y., et al., "Microbiota Dynamics in Patients Treated with Fecal Microbiota Transplantation for Recurrent Clostridium difficile Infection", PLOS One, vol. 8, Issue 11, Nov. 2013, pp. 1-11.
Stahlmann, J., et al., "Detection of nosocomial Clostridium difficile infections with toxigenic strains despite negative toxin A/B testing on stool samples", Clin Microbiol Infect, Jan. 23, 2014 (10 pgs.).
Stephen, A., et al., "The Microbial Contribution to Human Fecal Mass", J. Med. Microbiol., vol. 13, 1979, pp. 45-56, The Pathological Society of Great Britain and Ireland.
Stern, A. et al., "CRISPR Targeting Reveals a Reservoir of Common Phages Associated with the Human Gut Microbiome", Genome Research, 2012, pp. 1985-1994, Cold Spring Harbor Laboratory Press.
Stock, J., "Gut microbiota: an environmental risk factor for cardiovascular disease", Atherosclerosis, Aug. 2013; 229 (2):440-2.
Sunkesula, V.C., et al., "Does empirical Clostridium difficile infection (CDI) therapy result in false-negative CDI diagnostic test results?", Clin Infect Dis, Aug. 2013; 57(4):494-500.
Surawicz, C., et al., "Guidelines for Diagnosis, Treatment and Prevention of Clostridium difficile Infections", American Journal of Gastroenterology, vol. 108, Apr. 2013, pp. 478-498, American College of Gastroenterology.
Suvarna, K., et al., "Case Studies of Microbial Contamination in Biologic Product Manufacturing", Microbiology, Jan./Feb. 2011, pp. 50-57.
Swift, H., "Preservation of Stock Cultures of Bacteria by Freezing and Drying", Jan. 1, 1921, pp. 1-7.
Tang, P., et al, "Limited clinical utility of Clostridium difficile toxin testing in infants in a pediatric hospital", Diagn Microbiol Infect Dis, Jun. 2005; 52(2):91-4.
Tannock, G., "The Bowel Microbiota and Inflammatory Bowel Diseases", International Journal of Inflammation, 2010, pp. 1-9.
Taori, S.K., et al., "A prospective study of community-associated Clostridium difficile infections: The role of antibiotics and co-infections", J Infect, Apr. 26, 2014 (11 pgs.).
Taur, Y., et al., "Harnessing microbiota to kill a pathogen: Fixing the microbiota to treat Clostridium difficile infections", Nat Med., Mar. 2014; 20(3):246-7.
Taur, Y., et al., "Intestinal domination and the risk of bacteremia in patients undergoing allogeneic hematopoietic stem cell transplantation", Clin Infect Dis., Oct. 2012; 55(7):905-14.

\* cited by examiner

MICROBIOTA RESTORATION THERAPY (MRT), COMPOSITIONS AND METHODS OF MANUFACTURE

CROSS-REFERENCE TO RELATED APPLICATIONS

This application is a continuation-in-part of U.S. application Ser. No. 14/295,686, filed Jun. 4, 2014, which claims priority to U.S. Provisional Application Ser. No. 61/831,409, filed Jun. 5, 2013, the entirety of which are incorporated herein by reference.

TECHNICAL FIELD

The present disclosure pertains to compositions and methods for treating diseases and/or conditions of the digestive tract.

BACKGROUND

A wide variety of compositions and methods have been developed for treating diseases and/or conditions of the digestive track. Of the known compositions and methods, each has certain advantages and disadvantages. There is an ongoing need to provide alternative compositions and methods for treating diseases and/or conditions of the digestive track.

BRIEF SUMMARY

Microbiota restoration therapy compositions and methods for manufacturing, processing, and/or delivering microbiota restoration therapy compositions are disclosed. An example method for manufacturing a microbiota restoration therapy composition may include collecting a human fecal sample and adding a diluent to the human fecal sample to form a diluted sample. The diluent may include a cryoprotectant. The method may also include mixing the diluted sample with a mixing apparatus and filtering the diluted sample. Filtering may form a filtrate. The method may also include transferring the filtrate to a sample bag and sealing the sample bag.

An example method for manufacturing, processing, and packaging a microbiota restoration therapy composition may include collecting a fecal sample from a pre-screened donor, transferring the fecal sample to a filter bag, and adding a diluent to the filter bag. The diluent may include a cryoprotectant. The method may also include sealing the filter bag, transferring the sealed filter bag to a mixer, and transferring the filtrate from the filter bag to a sample bag. Transferring the filtrate from the filter bag to a sample bag may define the microbiota restoration therapy composition within the sample bag. The method may also include sealing the sample bag, cooling sample bag, and transferring the cooled sample bag to a controlled temperature storage device. Transferring the cooled sample bag to a controlled temperature storage device may include freezing the microbiota restoration therapy composition. The method may also include thawing the frozen microbiota restoration therapy composition, packaging the sample bag in an insulated packaging system, and shipping the packaged sample bag to a treatment facility.

An example method for medical treatment may include collecting a fecal sample from a pre-screened donor, transferring the fecal sample to a filter bag, and adding a diluent to the filter bag. The diluent may include a cryoprotectant. The method may also include sealing the filter bag, transferring the sealed filter bag to a mixer, and transferring the filtrate from the filter bag to a sample bag. Transferring the filtrate from the filter bag to a sample bag may define a microbiota restoration therapy composition within the sample bag. The method may also include sealing the sample bag, cooling sample bag, and transferring the cooled sample bag to a controlled temperature storage device. Transferring the cooled sample bag to a controlled temperature storage device may include freezing the microbiota restoration therapy composition. The method may also include thawing the frozen microbiota restoration therapy composition, packaging the sample bag in an insulated packaging system, shipping the packaged sample bag to a treatment facility, and administering the microbiota restoration therapy composition to a patient.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
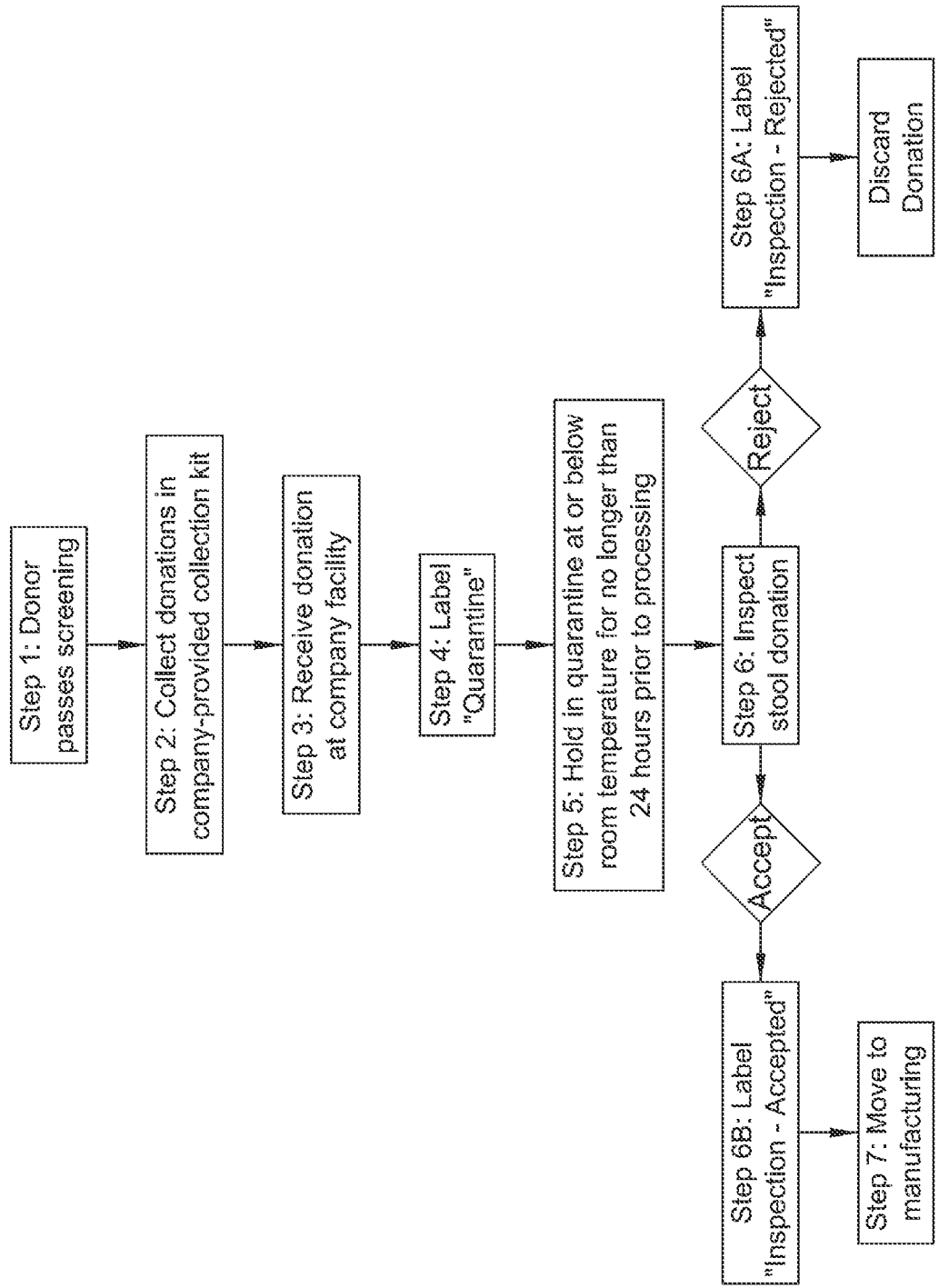
FIG. 1 is a flow chart schematically depicting a process for collecting and inspecting a donor fecal sample.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "cryopreservation", as used herein, refers to the process of cooling and storing biological cells, tissues, or organs at low temperatures to maintain their viability. As a non-limiting example, cryopreservation can be the technology of cooling and storing cells at a temperature below the freezing point (e.g., −20° C. or colder, −80° C. or colder, or the like) that permits high rates of survivability of the cells upon thawing.

The term "cryoprotectant", as used herein, refers to a substance that is used to protect biological cells or tissues from the effects of freezing.

As used herein, the term "microbiota" can refer to the human microbiome, the human microbiota, or the human gut microbiota. The human microbiome (or human microbiota) may be understood as the aggregate of microorganisms that reside on the surface and in deep layers of skin, in the saliva and oral mucosa, in the conjunctiva, and in the gastrointestinal tracts of humans. The human microbiome is comprised of bacteria, fungi, viruses, and archaea. At least some of these organisms perform tasks that are useful for the human host. Under normal circumstances, these microorganisms do not cause disease to the human host, but instead participate in maintaining health. Hence, this population of organisms is frequently referred to as "normal flora."

The population of microorganisms living in the human gastrointestinal tract is commonly referred to as "microbial flora", "gut flora", and/or "gut microbiota". The microbial flora of the human gut encompasses a wide variety of microorganisms that aid in digestion, the synthesis of vitamins, and creating enzymes not produced by the human body.

The phrase "microbiota restoration therapy", as used herein, refers to a composition which may include, but is not limited to, human fecal material containing viable gut flora from a patient or donor, a diluent, and a cryoprotectant. Additional compositions include equivalent freeze-dried and reconstituted feces or a "synthetic" fecal composition. The human fecal material is screened for the presence of pathogenic microorganisms prior to its use in the microbiota restoration therapy. The human fecal material is screened for the presence of *Clostridium* species including *C. difficile*, Norovirus, Adenovirus, enteric pathogens, antigens to *Giardia* species, *Cryptosporidia* species and other pathogens, including acid-fast bacteria, enterococci, including but not limited to vancomycin-resistant enterococci (VRE), methicillin-resistant *Staphylococcus aureus* (MRSA), as well as any ova or parasitic bodies, or spore-forming parasites, including but not limited to Isospora, Clyslospora, and Cryptospora.

More than 1000 different species of bacteria reside in a healthy gastrointestinal (GI) tract. Clostridia are anaerobic, spore-forming bacteria. Certain species of clostridia are pathogens, producing toxins that can be harmful to humans. *Clostridium difficile* ("*C diff*") is one species of *Clostridium* that, if overpopulated in the GI tract, can release toxins that can cause a number of symptoms, including bloating, constipation, diarrhea, inflammation, abdominal pain, among others that, in certain cases, can lead to death.

When stressed, *Clostridium difficile* create spores that can tolerate extreme conditions many active bacteria cannot. Generally, clostridia do not compete well in a healthy GI tract. However, antibiotics can disrupt the normal intestinal flora, leading to an overgrowth of *Clostridium difficile*. In certain examples, the *Clostridium difficile* spores can be resistant to various antibiotics. Thus, as the normal intestinal flora is cleared, the *Clostridium difficile* spores remain, leading to a large population of *Clostridium difficile*.

According to the Centers for Disease Control and Prevention, (CDC) approximately 337,000 cases of *Clostridium difficile* infection (CDI) are reported each year in the United States resulting in about 14,000 deaths. The current standard of care is antibiotic treatment; typically with metronidazole and/or vancomycin. Following initial antimicrobial treatment, approximately 25% of the patients experience a recurrence in symptoms. In this recurrent patient population, approximately 45-65% developed persistent recurrent CDI. Persistent recurrent CDI is associated with high morbidity and mortality. For example, estimates of *Clostridium difficile* overpopulation incidence vary from 1.5 to 2.7 million occurrences in the United States per year, and are growing. In one estimate, hospital discharges with *Clostridium difficile* doubled from 2001 to 2005, with an estimated 5% to 25% compound annual growth rate. Current estimates indicate that patients affected by *Clostridium difficile* overpopulation experience increased hospital stays from 3 to 36 days, with nearly 20% of affected patients being readmitted within 180 days, each more likely to be discharged to long-term care facilities than patients not affected. The financial impact of *Clostridium difficile* is estimated at $1 to $3 billion annually. Moreover, an estimated 300 patient deaths per day are attributable to *Clostridium difficile* overpopulation, a mortality rate of 1 to 7.7%, and increasing.

Traditional treatment for *Clostridium difficile* typically includes application antibiotics. Metronidazole ("Flagyl®") is the antibiotic of choice due to low price and high efficacy.

However, for recurring cases (up to 20% of total cases, for example, resistant to metronidazole), pregnant patients, or patients younger than 10 years of age, vancomycin ("Vancocin®") is typically used. However, vancomycin, although typically having fewer side effects than metronidazole, has a much higher cost and may lead to resistance of existing *Clostridium difficile* to further antibiotics.

At first occurrence, antibiotic treatment for *Clostridium difficile* can be acutely effective to treat diarrhea within 2 to 4 days at a rate approximately at or above 90%. However, *Clostridium difficile* typically recurs after the first occurrence (e.g., several days to 12 weeks after cessation of antibiotics) at an estimated 20% rate (e.g., 15%-30%). However, for each recurrence following the first recurrence, the rate increases greatly, to an estimated 40% rate following the second recurrence, and to greater than an estimated 60% rate or greater thereafter. It is estimated that approximately 5% of patients have 6 or more recurrences.

Treatment for *Clostridium difficile* typically varies after each occurrence. For example, for first mild to moderate recurrence, metronidazole can be administered orally (e.g., at a dose of 500 mg, three times daily ("TID") for 10 to 14 days). For a second recurrence, vancomycin can be administered orally in tapered or pulsed doses (e.g., at a dose of 125 mg, four times daily ("QID") for 14 days; at a dose of 125 mg, twice daily ("BID") for 7 days; at a dose of 125 mg, once daily ("QD") for 7 days; at a dose of 125 mg, once every 2 days for 8 days (four doses); at a dose of 125 mg, once every 3 days for 15 days (five doses), etc.). For a third recurrence, vancomycin can be applied at greater doses (e.g., at a dose of 125 mg, four times daily ("QID") for 14 days), combined with any of the other options for recurrent infection, such as intravenous immunoglobulin (e.g., at a dose of 400 mg per kg body weight, once every three weeks, for a total of two or three doses depending on effect), or rifamycin following the vancomycin doses (e.g., the rifamycin at a dose of 400 mg, twice daily ("BID") for 14 days), etc.

Fecal transplantation (FT), a treatment related to microbiota restoration therapy (MRT), has been practiced as a last resort for some patients having recurrent CDI. Following antimicrobial treatment, FT is used to re-establish a healthy microbial mix in the gastrointestinal microbiota of the patient. Over 480 cases have been reported with a ~90% cumulative success rate in curing recurrent CDI without any adverse events attributable to the FT material. The current institutional practice is to obtain fecal samples from family members or volunteers within the treating institution for transplantation into the patient. An evident problem with this technique of treatment is that the FT material is not standardized. Although donors are generally selected that are considered healthy at the time of donation, this is not adequate to assure both the quality and viability of the microbes to be transplanted. A disease state affecting the fecal material may be present that is unknown to the donor. In addition to the quality of the raw fecal material, the lack of a standardized procedure for processing and handling at the receiving or treating institution can lead to problems with both the quality and viability of the FT material given to the patient. Further, each institution must handle the raw fecal material, which is undesirable.

There is a need for a standardized, pre-processed MRT product that assures quality and viability of the MRT product for the patient at the time of delivery. It is further desirable to have an MRT product which can also be shipped to a suitable treatment facility after processing in a readily handled and deliverable state to eliminate handling of raw fecal material at each institution. With these improvements, MRT can become a desirable/viable primary treatment option for CDI rather than a treatment of last resort at a small number of institutions.

This document discusses, among other things, receiving a plurality of donor fecal samples from a plurality of donors and storing and indexing each respective donor fecal samples using at least one characteristic of the respective donor fecal sample. In an example, the donor fecal sample can be screened and processed for subsequent use in fecal bacteriotherapy to displace pathogenic or undesired organisms in the digestive track of a patient with healthy or desirable gut microbiota.

The disclosure provides a microbiota restoration therapy composition comprising a mixture of an effective amount of fecal microbiota and an effective amount of a cryoprotectant. An example cryoprotectant may include polyethylene glycol. Additionally, in the microbiota restoration therapy composition of the disclosure, the polyethylene glycol is present in a concentration from about 5-60 g/ml, or about 5-30 g/ml, or less than about 30 g/ml. The composition can further include saline as a diluent. The compositions of the disclosure may comprise polyethylene glycol having an average molecular weight ranging from about 600 to about 20000. For example, PEG-3150, having an average molecular weight of 3150 can be utilized. In certain embodiments, the microbiota restoration therapy compositions comprise fecal microbiota derived from one or more human stool samples.

Other cryoprotectants may be used such as dextrose, betaine, glycine, sucrose, polyvinyl alcohol, Pluronic F-127, mannitol, tween 80, ethylene glycol, 1,3-propanediol, hydroxypropyl cellulose, glycerol, PEG/glycerol mix, milk (e.g., skim milk), and propylene glycol.

In other embodiments, the viability of the microbiota of the compositions of the disclosure may be confirmed by culturing the microbiota (and/or the filtrate and/or a bacteriotherapy composition) on a Bacteriodes Bile Esculin Agar (BBE) plate (available from Becton, Dickinson and Company, catalog number 221836, BBL™ *Bacteroides* Bile Esculin Agar BBE plate), or a Center for Disease Control (CDC) plate (available from Becton, Dickinson and Company, catalog number 221733, BBL™ CDC Anaerobe 5% Sheep Blood Agar Plates), or both. In at least some embodiments, the viability of the microbiota of the compositions of the disclosure may be confirmed on a BBE and/or CDC plate by the presence of a colony forming unit (CFU) count of about 30 CFU to about 300 CFU at a serial dilution of $10^{-5}$, or by the presence of a CFU count of about 30 CFU to about 300 CFU at a serial dilution of $10^{-6}$. Further provided are microbiota restoration therapy compositions where the concentration of microbiota is on the order of about $10^7$ microbes/ml. Additionally, the methods for producing a microbiota restoration therapy composition may further comprise the steps of conducting both pre- and post-donor screening with the human stool sample collected in the interval there between.

In addition to confirming viability of the microbes, the plating tests can also confirm the diversity of the living microbes present. The mix of microbes present, or diversity of microbes, is a further measure of the quality of the human stool sample and the MRT product made from that sample. The CDC plates and the BBE plates, either alone or in combination provide a measure of quality through diversity as described herein.

The disclosure also provides methods for assuring the quality of a human stool sample to be processed into a microbiota restoration therapy composition, the methods comprising identifying a human stool donor; conducting a pre-donation screening of the donor, comprising a health history questionnaire, a daily diet questionnaire, and at least one blood test; collecting a human stool sample from the donor; processing a the stool sample from the donor to form one or more microbiota restoration therapy compositions; conducting a post-donation screening of the donor at an interval of about 15-120 days, or about 30-100 days, or about 45-90 days, comprising a health history questionnaire and at least one blood test; holding in quarantine one or more microbiota restoration therapy compositions processed from the donor stool sample collected during the interval between pre-donation screening and post-donation screening; confirming the quality of the microbiota restoration therapy compositions from both pre- and post-screening results; and releasing for the microbiota restoration therapy compositions for use in a human in need of microbiota restoration therapy. Pre/Post screening may improve the likelihood of collecting a healthy sample. The interval is selected to allow adequate time for a disease state or other factor that is present at the time of human stool collection to manifest with symptoms or be positively identified in a human stool or serum test at the post-screening. Further, the composition can be quarantined and stored until validation of donor health via both the pre- and post-screening is confirmed.

The methods of the disclosure may further include the step of conducting at least one test on the human stool sample for the presence of infectious disease. Additionally, the methods of the disclosure may further include the step of testing the human stool sample for a constituent selected from the group consisting of: *C. difficile*; Norovirus; Adenovirus; Enteric Pathogens; *Giardia* antigen; *Cryptosporidium* antigen; Acid-fast staining (Clyslospora, Isospora); ova and parasites; Vancomycin-resistant enterococci (VRE); Methicillin-resistant *Staphylococcus aureus* (MRSA) and combinations thereof. The methods of the disclosure may include testing the blood of the donor, wherein the blood test includes at least one test for a constituent selected from the group consisting of: HIV; Hepatitis A; Hepatitis B; Hepatitis C; RPR and combinations thereof.

A representative method for producing a microbiota restoration therapy composition from a human stool sample and assuring viability of the composition can include collecting a desired amount of human stool sample, adding saline, adding a cryoprotectant (e.g., polyethylene glycol), and mixing the composition. The resultant mixture can then be filtered and the filtrate containing microbes collected. A portion of the filtrate can be collected for testing and the remainder of the filtrate can be frozen as quarantined until testing verifies the quality of the frozen filtrate based on culturing of the test sample coupled with results of pre- and post-screening as described above.

The present disclosure is directed to compositions, methods of manufacture, and methods of treatment utilizing microbiota restoration therapy of the gastrointestinal tract by displacing pathogenic and/or ineffective organisms with healthy, effective bacterial flora. Example conditions and disease states that may be treated include *Clostridium difficile* infection, irritable bowel syndrome (IBS), Crohn's disease, ulcerative colitis (UC), fulminant colitis resulting from a staphylococcus or *C. diff* infection, inflammatory bowel disease (IBD), ulcers, diabetes, colon cancer, constipation, obesity, and other conditions and disease states related to an imbalance of the intestinal bacterial flora.

In some examples, compositions, methods of manufacture and methods of treatment utilizing microbiota restoration therapy (MRT) for the treatment of *Clostridium difficile* infections (CDI) are provided. CDI is a common nosocomial infection and is frequently associated with severe morbidity and mortality, especially in elderly patients.

Each individual has a personalized gut microbiota including an estimated 500 to 5000 or more species of bacteria, fungi, viruses, archaea and other microorganisms, up to 100 trillion individual organisms, that reside in the digestive tract, providing a host of useful symbiotic functions, for example, including aiding in digestion, providing nutrition for the colon, producing vitamins, stimulating the immune system, assisting in defense against exogenous bacteria, modulating energy metabolism, and the production of short chain fatty acids (SCFAs), specifically, dietary carbohydrates, including resistant starches and dietary fiber, which are substrates for fermentation that produce SCFAs, primarily acetate, propionate, and butyrate, as end products. However, an improperly balanced or functioning gut microbiota may play a role in certain diseases or afflictions, such as pseudomembranous colitis, *Clostridium difficile* colitis, antibiotic-associated diarrhea (AAD), ulcerative colitis (UC), pouchitis, irritable bowel syndrome (IBS), obesity, among others.

Accordingly, the present inventor has recognized, among other things, systems and methods for providing bacteriotherapy to treat afflictions associated with the gut microbiota, including *Clostridium difficile* colitis, by displacing pathogenic organisms in the digestive track of a patient with healthy bacterial flora, or bacterial flora intended to benefit a specific individual with an affliction associated with the gut microbiota. In an example, the systems and methods described herein can provide a convenient, hygienic mechanism, capable of meshing with existing capabilities and routines of existing clinics and hospitals, for providing bacteriotherapy to a patient. In certain examples, similar treatment can be effective for patients with other diseases, such as IBS, Crohn's disease, ulcerative colitis (UC), inflammatory bowel disease (IBD), ulcers, or other gastrointestinal, metabolic, or digestive tract related disease. In other examples, bacteriotherapy can be used to aid in weight loss, displacing ineffective flora in the gut with a more effective microbiota. In other examples, bacteriotherapy can be used to aid in cardiovascular and peripheral vascular disease.

In an example, bacteriotherapy to treat *Clostridium difficile* or one or more other diseases or afflictions of the digestive tract can be provided using a combination of antibiotics and re-population of a healthy or desired mammalian bacterial flora. In certain examples, the re-population of bacterial flora can include fecal bacteriotherapy, or fecal transplant.

The process of fecal bacteriotherapy can include introducing a fecal sample of a healthy donor, or a donor having one or more desired characteristics, into a gastrointestinal tract of a patient to repopulate a healthy or desirable gut microbiota. In certain examples, prior to introduction of the fecal sample, the patient's intestinal flora can be disrupted using antibiotics, such that the healthy or desirable gut microbiota, once introduced into the patient, can easily populate the gastrointestinal tract. For example, some of the methods contemplated herein may include methods for treating a gastrointestinal disorder that include administering a pre-treatment antibiotic to a patient with a gastrointestinal disorder and administering a microbiota restoration therapy composition (e.g., the microbiota restoration therapy compositions as disclosed herein) to the patient. The pre-treatment antibiotic may include vancomycin, fidaxomicin, rifaximimin, linezolid, daptomycin, quinupristin-dalfopristin, tigecycline, ceftaroline, ceftobiprole, televancin, teicoplanin, dalbavancin, metronidazole, oritvancin, or a combination thereof. The pre-treatment antibiotic may be administered at a suitable dose (e.g., about 0.01 mg per day to about 5000 mg per day). In some instances, the pre-treatment antibiotic is administered as a single dose. In other instances, two or more doses may be administered. If two or more doses are administered, the antibiotics used for each of the doses may be the same or different. In some instances, pre-treatment with an antibiotic may not be necessary or desired. Accordingly, methods are contemplated that do not include pre-treatment with an antibiotic (e.g., pre-treatment is purposefully omitted).

The methods for treating a gastrointestinal disorder may also include administering a post-treatment antibiotic to the patient after administering the microbiota restoration therapy composition to the patient. The post-treatment antibiotic may be the same as or different from the pre-treatment antibiotic. In some instances, post-treatment with an antibiotic may not be necessary or desired. Accordingly, methods are contemplated that do not include post-treatment with an antibiotic (e.g., post-treatment is purposefully omitted).

The methods for treating a gastrointestinal disorder may also include administering a second dose of the microbiota restoration therapy composition to the patient. Additional doses may also be administered. Multiple doses of the microbiota restoration therapy composition may be administered in conjunction with one or more doses of a pre-treatment antibiotic (e.g., as disclosed herein), in the absence of a pre-treatment antibiotic, in conjunction with one or more doses of a post-treatment antibiotic (e.g., as disclosed herein), in the absence of a post-treatment antibiotic, or the like.

In one example, a single dose of a pre-treatment antibiotic is administered to the patient and a primary dose of the microbiota restoration therapy composition is administered to the patient. This example may or may not include administration of one or more doses of a post-treatment antibiotic to the patient.

In another example, a primary dose of a pre-treatment antibiotic is administered to the patient, a secondary dose of a pre-treatment antibiotic is administered to the patient, and a primary dose of the microbiota restoration therapy composition is administered to the patient. This example may or may not include administration of one or more doses of a post-treatment antibiotic to the patient.

In another example, a single dose of a pre-treatment antibiotic is administered to the patient, a primary dose of the microbiota restoration therapy composition is administered to the patient, and a secondary dose of the microbiota restoration therapy composition is administered to the patient. This example may or may not include administration of one or more doses of a post-treatment antibiotic to the patient.

In another example, a primary dose of a pre-treatment antibiotic is administered to the patient, a secondary dose of a pre-treatment antibiotic is administered to the patient, a primary dose of the microbiota restoration therapy composition is administered to the patient, and a secondary dose of the microbiota restoration therapy composition is administered to the patient. This example may or may not include administration of one or more doses of a post-treatment antibiotic to the patient.

In another example, a primary dose of the microbiota restoration therapy composition is administered to the patient in the absence of administering a pre-treatment antibiotic to the patient. This example may or may not include administration of one or more doses of a post-treatment antibiotic to the patient.

In another example, a primary dose of the microbiota restoration therapy composition is administered to the patient and a secondary dose of the microbiota restoration therapy composition is administered to the patient. The primary and secondary doses of the microbiota restoration therapy composition are administered in the absence of administering a pre-treatment antibiotic to the patient. This example may or may not include administration of one or more doses of a post-treatment antibiotic to the patient.

Administering the antibiotics and/or the microbiota restoration therapy compositions to the patient may include suitable routes of administration including those disclosed herein (e.g., orally, by enema, by suppository, or the like).

The human fecal material is optionally filtered prior to its use in the microbiota restoration therapy.

In some embodiments of the present disclosure, the composition is a standardized fecal microbial preparation from pre-screened donors. Donors are screened for common infectious diseases in both serum and human stool. This includes laboratory testing as well as review of the donor's medical history. Once the donor has been qualified, he/she will be required to undergo complete re-screening at selected intervals. This can include a period of each one to three month period, with one example interval of approximately every three months. In some methods of a system for collecting quality or normal fecal material, in between the complete re-screenings, donors will be instructed to contact the sample collector immediately if changes to their health status occur. Further this health information can be collected at the time of every donation between complete screenings via questionnaire or other means. The donor can continue to be a qualified donor as long as he/she continues to pass their screening tests and meet the health status requirements.

Collected human stool can be processed as disclosed herein, then frozen and quarantined. The product can be released from quarantine when both pre-collection and post-collection medical screening (for example, human stool and blood tests along with health status) is completed. This assures the quality of the sample collected between screenings. The product can be thawed and shipped in a temperature-controlled container to the institution or alternatively shipped frozen and thawed at the institution.

The present composition is particularly suited for patients having recurrent CDI. Recurrent CDI is defined as a patient who has had a minimum of at least one recurrent episode after the primary episode, and will have completed at least two courses of oral antibiotics to treat their CDI. The composition is also suited for treatment of a primary episode of CDI.

In one method of treatment in the present MRT, a patient can complete a 10-14 day course of oral antibiotics, including at least 7 days of vancomycin at the end of the regimen, followed by a 24-48 hour washout period. The MRT composition can then be introduced via enema. The treatment can be considered successful if there is resolution of CDI symptoms at 60 days after administration of the first enema. In some patients, a second enema with the MRT composition can be administered if symptoms return within the 60 day period and successful treatment can be non-recurrence of symptoms within 60 days following the second enema.

Human fecal material is by nature variable between donors and even varies from day-to-day in the same donor. Further, an individual sample of human fecal material has more than 1000 different microbes present at any time making it not feasible to test and delineate the entire fecal microbiome in a sample and even less feasible to determine the effect of individual species of microbes on a given disease, such as CDI. However, with the present disclosure, it in has been found that a standardized or normal sample of fecal material can be identified and processed to a MRT composition or MRT product that assures safety and viability. With a variable raw material, the present composition is made using donor screening methods, fecal testing methods, fecal processing methods, processed material handling, storage and preservation methods, and testing methods to produce a consistent, reproducible, quality-controlled composition from human feces to be delivered as a therapeutic product for treating various conditions and disease states affected by microbial imbalance within the GI tract.

The present composition can begin with what is characterized as a normal human stool sample. In order to define a normal human stool sample the patient can be screened via questionnaire or other health history means coupled with blood and/or human stool testing to confirm or check other characteristics. Further, the human stool sample can be handled and processed in a controlled manner with the resultant product tested to confirm both that the human stool sample was normal and that the processing and handling has been completed in a way that maintains the viability of the microbes in the product composition. In addition to viability, selected testing can be performed to affirm the diversity of viable microbes present, another measure of healthy or normal stool. In this way, donor to donor variation and within donor day-to-day variation can be understood and utilized in the criteria for a normal human stool sample. Further, the validity of the processing and handling techniques as designed and implemented can be confirmed. The combination of collecting a normal human stool and using validated processing and handling techniques results in a standardized composition or product. Once a standardized composition is made, it must be stored and handled from production to administration in a way that maintains the viability of the product to assure successful treatment. A validated process which maintains viability of the standardized product from the time of production through administration to the patient is critical to successful treatment. It will be appreciated that during the processing of samples, the encapsulation of such extracts to produce medicaments of the disclosure, it may generally be desirable to track a sample to ensure that that the medicaments produced are tracked, stored and banked appropriately for later processing, handling and use. In order to facilitate such tracking it may be desirable that suitable tags be used to identify a sample, extract and medicine, and allow these to be associated with one another, and with the patient to be treated. This may be achieved by the use of RFID tags or DNA analysis of donor samples. One skilled in the art would be familiar with other tags suitable for tracking medicaments of the disclosure, for example bar codes.

In characterizing the human stool sample to determine whether it is normal or within the range considered normal, health history data, serum and/or blood analysis and human stool analysis can be utilized. Additionally, a constant set of processing parameters can be utilized to produce a product that can be cultured on selected media to determine the presence of viable select microbes and groups of microbes to confirm viability and diversity within the human stool sample. The processing parameters can also be utilized to produce a product that can be cultured on selected media to determine the absence of certain microbes and/or groups of microbes. This part of the processing protocol can be used to confirm safety of the stool sample for use in the MRT product.

The handling and processing of the human stool sample to a standardized and viable MRT product can include consistent and proven collection and handling techniques, filtering processes, controlled homogenization and addition of select liquids and amounts of these liquids. Further, the composition produced, which is the standardized composition or product, by this controlled and proven handling and processing, can be cultured on selected media to determine the presence of viable select microbes and groups of microbes to confirm the viability and microbe diversity in the product.

From the time of producing the standardized product through the time of administration to the patient, the standardized product must be maintained viable for successful treatment. This can include using a frozen storage technique and cryoprotectant to maintain viability. In particular, Applicants have discovered that polyethylene glycol (PEG) can be used as an effective cryoprotectant for MRT products. Time of storage, thawing technique, shipping technique and handling of the thawed product are also factors that affect viability and are defined herein. The techniques defined herein can be used from the time the stool donation is received through the production of the standardized product and through the administration to the patient. The techniques provided herein also allow for viability of the microbiota in the MRT product to be maintained and confirmed. Provided are protocols for confirming the presence, viability and diversity of select microbes and groups of microbes by culturing on selected media. Further, the techniques provided herein can be used to confirm the presence, viability and diversity of select microbes and groups of microbes at any point during the process, from collection to processing to production to storage to post-thaw to just prior to administration to a patient and at every point in between. In one embodiment, the cryoprotectant polyethylene glycol (PEG) can be mixed with the human stool sample and isotonic saline at the time of processing. PEG can be added at a concentration from about 0.1 g/ml. to about 70 g/ml, or from about 2 g/ml to about 68 g/ml, or from about 4 g/ml to about 65 g/ml, or from about 5 g/ml to about 60 g/ml. The PEG used can have an average molecular weight of about 600 to about 20000. In some embodiments, the PEG has an average molecular weight of about 2000 to about 4000, for example about 3350 as provided in the formulation of PEG 3350.

The growing of cultures to define normal human stool sample can include the following techniques, recognizing that the raw human stool cannot be consistently cultured. A processed sample product was made using a 50 gram (g) human stool sample and mixed under consistent conditions with a ratio of about 2 to about 4 mL of a PEG/saline mixture to 1 g of human stool in a sterile mixing/filter bag to create a bacterial suspension. In some embodiments, the bacterial suspension is filtered, according to standard techniques, prior to culturing. Plating and incubation of the bacterial suspension was done on growth media as described herein below, and was done according to industry standard anaerobic culture methods. Resulting colony forming units (CFU) were counted, and consistent results were achieved using these protocols.

Two culturing media are used to culture the bacterial suspension. The first is the Center for Disease Control (CDC) plate, commonly referred to as "CDC Anaerobe 5% Sheep Blood Agar plate. This plate is a general anaerobic microbe plate, which allows for the isolation and cultivation of fastidious and slow-growing obligately anaerobic bacteria. The second is the *Bacteroides* Bile Esculin Agar (BBE) plate, which is a specific indicator species media for *Bacteroides*. Both types of media are commonly available for purchase through laboratory suppliers, such as Becton, Dickinson and Co., and Fisher Scientific, for example.

By culturing on selected media, Applicants are able to provide a measure of the diversity of microbes present in the human stool, the product produced and the product being administered. The techniques disclosed above can be used to provide a measure of the diversity of the microbes in a human stool sample at any stage. In particular, the CDC plates are designed to grow 5 to 7 different families of microbes that can be present in the MRT materials. In one non-limiting example, a CDC plate cultured with a bacterial suspension must have at least 3 identifiable genera of microbes growing thereon in order for the bacterial suspension to be processed and/or used for MRT therapy. Further, the use of the BBE plate can provide an additional measure of microbial diversity in the MRT product. The BBE plate grows multiple species within the *Bacteroides* genus of microbes. Sufficient CFUs on the BBE plates indicate the diversity within the genus present in the MRT product. In certain embodiments, the CDC plate or the BBE plate can be used alone as a measure of diversity. In other embodiments, both the CDC plate and the BBE plate can be used together to provide an enhanced measure of diversity at the microbe genus level, as well as at the species level within a particular microbe genus.

FIG. 1 is a flow chart depicting a portion of an example MRT production process. More particularly, FIG. 1 schematically depicts a process for collecting and inspecting a donor fecal sample. As a first step in the collecting/inspecting process, potential stool donors are screened. Screening/prescreening is described in more detail herein. Once the donor passes the screening, step two may include collecting the donor's stool using a human stool collection kit as defined herein, whether at home or at a collection facility. The kit can include, but is not limited to, a clean human stool collection container with lid, a large closeable/sealable bag, a donation form and a human stool collection instruction sheet. The time and date of collection, along with donor identity and method of transport, can be recorded in order to track the time from collection to processing, and the conditions of transport. As a non-limiting example, the collection container can include an indicator of the minimum and the maximum temperature to which the sample is exposed. As another non-limiting example, one or more temperature sensitive stickers that changes color at temperatures below about 4° C. and temperatures greater than about room temperature (about 22-29° C.) can be affixed to the container.

Step three may involve transporting the sample to a processing facility. It can be appreciated that if the sample is collected at the processing facility, transporting the sample is not necessary. In some instances it may be desirable to collect the sample at the processing facility in order to more clearly establish the chain of custody of the sample. With the receipt of the first stool donation for any individual, a profile will be established for each donor. Subsequent stool samples can be subjected to a human stool test, which is utilized to match and confirm the identity of the donor with the donation. Based on prior collected samples, a human stool profile for the donor is generated and can be maintained or enhanced over repeated donations. Any new sample will be compared with this profile to confirm it is the same donor. Differentiation can be made to confirm donor identity based on the representation of *Bacterioides* species in the human stool. In a non-limiting example, the base set of stool samples used to create the profile is collected at the processing facility to assure donor identity in the profile samples. In another non-limiting example, the base set of stool samples used to create the profile can be collected in locations other than the processing facility, with donor identity assurance protocols appropriate to the situation or location.

Step four of the method may include labeling the donation "Quarantine" and holding the donation in quarantine at or below room temperature for no longer than 24 hours prior to processing. Donations may be rejected in situations where the temperature indicator has been activated or where the time between donation and receipt exceeds 24 hours. In addition, where applicable, the human stool test results must match the donor profile. If the human stool test does not match the donor profile, the donation collected for that day will be discarded and the donor will be disqualified.

In one method of the disclosure, the human stool sample is processed within about 24 hours of collection. In another method of the application, the time of collection is recorded at the time of arrival of the stool sample at the processing facility. Step six may include inspecting the stool donation. Visual inspection can be completed upon arrival of the stool sample at the processing facility. In the event the human stool sample is loose, unformed, is not of sufficient weight (e.g., less than about 50 g), or for any other reason, including but not limited to evidence indicating poor sample quality or concerns about donor health, the sample may be rejected, labeled "Inspection—Rejected" and the donation is discarded. Further, answers to questions on the human stool collection form can be reviewed by trained personnel. Certain answers in the collection form may require ample rejection. If the sample is accepted, it may be labeled "Inspection—Accepted" and may be moved to a manufacturing process.

Figure 2:
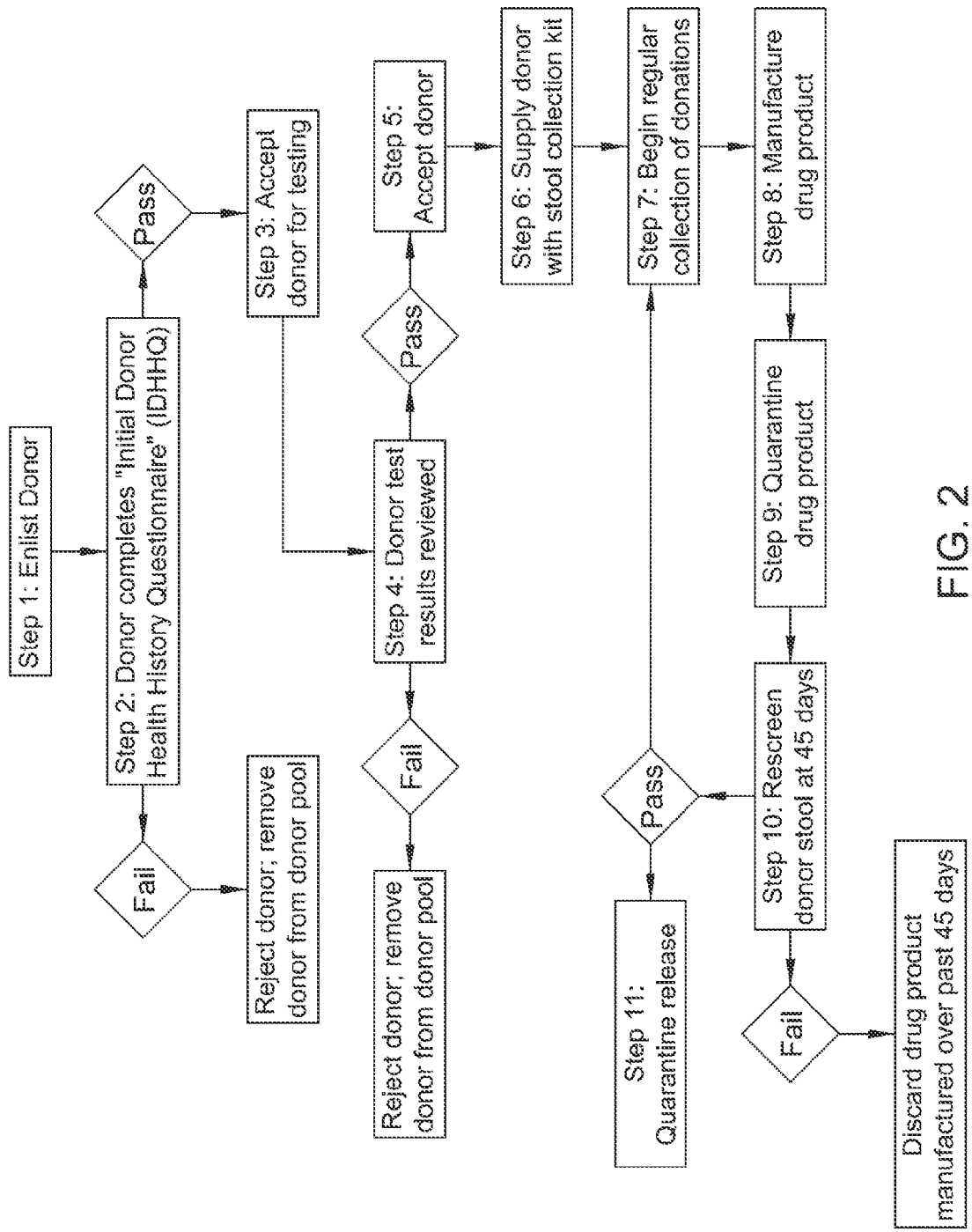
FIG. 2 is a flow chart schematically depicting a process for screening a fecal donor.

Another example method of screening donors, obtaining human stool samples, and processing the stool samples to a MRT product is illustrated in the flow chart depicted in FIG. 2. Step one may include enlisting potential donors. Step two may include having the potential donors complete an Initial Donor Health History Questionnaire (IDHHQ). The questionnaire may be similar to that used by the Red Cross for screen of potential blood donors (with potentially additional screening questions, if desired). A result of "fail" causes the potential donor to be rejected and removed from the donor pool. For example, a donor will receive a "fail" result under conditions similar to what would cause a potential donor to fail a Red Cross screen. A result of "pass" causes the donor to be accepted for further testing. Step four may involve further testing and review which, if the donor fails, removes the donor from the pool. Donors are regularly screened for common infectious diseases and other conditions as listed herein. A review of the donor's medical history by trained personnel, and repeat screening tests, will be conducted at regular intervals, such as, but not limited to, approximately every 15-90 days. Screening can include the constituents listed in Table 1, below.

TABLE 1

Donor Screening Tests

| Test Name | Material Tested | Acceptance Criteria |
|---|---|---|
| *C. difficile* B via PCR and GDH | Stool | Negative for *C. difficile* GDH result is not a pass/fail criterion - for information only |
| Norovirus via PCR | Stool | Negative |
| Rotovirus via PCR | Stool | Negative |
| Adenovirus via PCR | Stool | Negative |

TABLE 1-continued

Donor Screening Tests

| Test Name | Material Tested | Acceptance Criteria |
|---|---|---|
| Enteric Pathogens (*Shigella, Salmonella, Campylobactoer, sorbitol-negative E. coli., Aeromonas, Yersinia, Plesiomonas, Shiga* toxins) | Stool | Negative for *Shigella, Salmonella, Camphylobacter, sorbitol-negative E. coli., Aeromonas, Yersinia,* and *Plesiomonas.* No *Shiga* toxins detected |
| *Giardia* Antigen | Stool | Negative |
| *Cryptosporidium* Antigen | Stool | Negative |
| Acid-fast Staining (*Clyslospora, Isospora*) | Stool | Negative |
| Ova and Parasites | Stool | No detection/identification of: *Giardia, Entamoeba histolytica* (amoeba), *Helminth* eggs, protozoa, larval worms and segments |
| Vancomycin-resistant enterococci (VRE) | Stool | No VRE isolated |
| Methicillin-resistant *Staphylococcus aureus* (MRSA) | Stool | No MRSA isolated |
| Vibrio | Stool | Non-reactive |
| Listeria | Blood (Serum) | Negative |
| Human Immunodeficiiency Virus (HIV) | Blood (Serum) | Non-reactive |
| Hepatitis A (IgG); must be + or else be vaccinated | Blood (Serum) | Non-reactive |
| Hepatitis B: Anti-Hepatitis B surface antigen must be + or else be vaccinated | Blood (Serum) | Non-reactive |
| Hepatitis C Antibody | Blood (Serum) | Non-reactive |
| Treponema Antibody | Blood (Serum) | Negative |

These are just examples. Other tests may also be utilized.

Step five may involve accepting a passing donor into the donor pool, and step six may involve supplying the donor with a stool collection kit. Step seven may involve starting a schedule of regular collections of stool samples from the accepted donor, and step eight may involve manufacturing a drug product from the collected stool samples. Step nine may involve quarantining the drug product, and step ten may involve rescreening the donor stool sample at 45 days. If the sample fails the screening, all drug product produced from that donor over the past 45 days is discarded. If the sample passes the screening, the drug product is released from quarantine (step 11).

In another exemplary method, a human stool sample is weighed and 45 to 75 g of the sample is transferred into a sterile filter bag. A mixture of saline and a cryoprotectant (e.g., polyethylene glycol (PEG) 3350) is used as a diluent, and thus can be added to the human stool sample. As used herein, the terms "saline/PEG mixture" and "diluent" are interchangeable. The PEG concentration of the diluent can be approximately about 30-90 g/liter. The PEG concentration of the diluent can also be approximately between about 25-75 g/liter. In one example, the ratio of saline/PEG mixture to stool sample is 2:1, or 2 mL saline/PEG mixture to 1 gram human stool. As a non-limiting example, approximately 100 mL of saline/PEG mixture can be used for 50 g of human stool. While saline/PEG may be suitable for use as a diluent (and/or cryoprotectant), this is not intended to be limiting. Other cryoprotectants may also be utilized. For example, dextrose, betaine, glycine, sucrose, polyvinyl alcohol, Pluronic F-127, mannitol, tween 80, ethylene glycol, 1,3-propanediol, hydroxypropyl cellulose, glycerol, PEG/glycerol mix, propylene glycol, or combinations thereof may be used as cryoprotectants. These materials may be used alone or in combination with a solvent such as saline.

Once the diluent is added to the bag containing the human stool sample, the bag is sealed. Using a paddle mixer, the stool sample is mixed with the diluent. The product of the mixed stool sample and diluent is referred to as a bacterial preparation.

The bacterial preparation can be filtered according to standard techniques and the filtrate can be removed from the mixing bag and transferred into sterile pouches or bags. In some embodiments, the bacterial preparation is not filtered.

In other embodiments, each bag containing the bacterial preparation (filtered or not filtered) is the equivalent of one dose of MRT product and is treated as one dose of MRT. In other embodiments, the bags may be stored according to proper protocol and aliquoted into smaller amounts at a later date. In still other embodiments, the bags may be stored according to proper protocol, and combined to make one or more doses. Additionally, one or more of the bags of the bacterial preparation can be retained for Quality Control (QC).

In one non-limiting example, the bags can be labeled with the product number and frozen. Once this occurs, the bags may be considered doses of MRT product. The product number can include reference to the donor ID and date of manufacture (date of processing). The MRT product can be frozen at about −20° C. to about −80° C. or colder. The MRT product can then be quarantined until the evaluation of the results from the QC test and the additional tests, as described below.

In another non-limiting example, the bags can be labeled with the product number and frozen. The product number can include reference to the donor ID and date of manufacture (date of processing). These labeled bags can be frozen at about −20° C. to about −80° C. or colder (e.g., as cold as about −192° C. as may be accomplished by freezing under liquid nitrogen, if desired). The contents of the bags can then be quarantined until the evaluation of the results from the QC test and the additional tests, as described below.

In one exemplary test of the quality of the manufactured MRT product (including the viability of the microbes as processed), a fecal donation or stool sample collected from a single qualified donor on a single day can be processed. In some embodiments, no pooling of samples between donors or between samples of an individual donor will be done. In other embodiments, sample preparations from an individual donor are pooled or combined. In other embodiments, sample preparations from more than one donor are combined.

A sample of the processed human stool or the MRT product can be diluted, plated, incubated and counted according to standard industry procedures. Anaerobic CFU can be counted on a CDC plate and *Bacteroides* CFU can be counted on a BBE plate. Plate counts will be checked against the Quality Control standards, which can include, but are not limited to, testing results from prior donations for the particular donor and other established, appropriate standards. If the counts are within the acceptable range, the MRT product will be considered acceptable. If the counts are not within the acceptable range, all bags of the MRT product made from the same human stool sample will be removed from the freezer and destroyed. Final acceptable count ranges can be between about 30 to about 300 CFU at a serial dilution level of $10^{-6}$ on the CDC plates and about 30 to about 300 CFU at a serial dilution level of $10^{-5}$ on the BBE plates, prior to freezing of the sample preparation or MRT product.

Figure 3A:
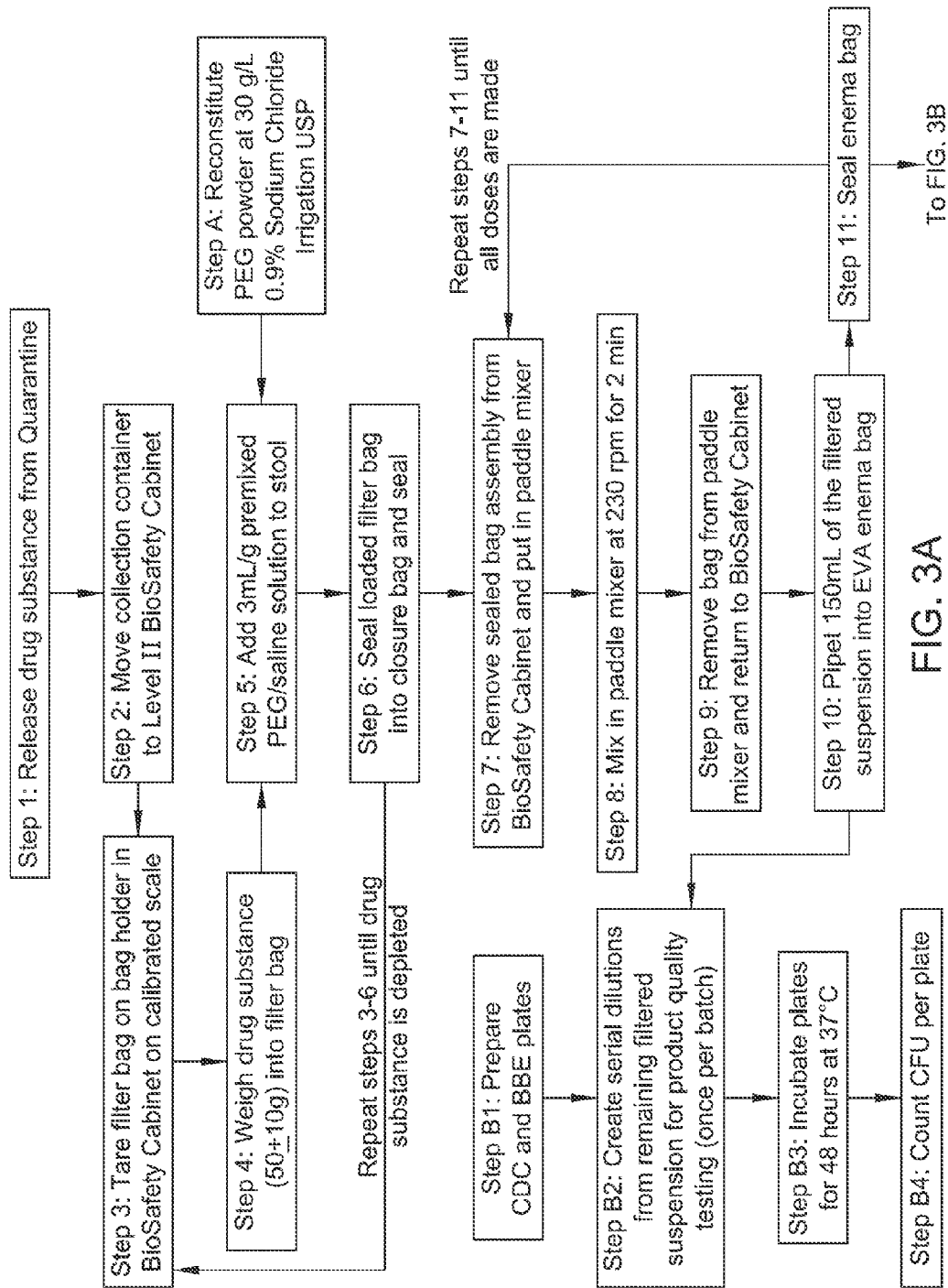
FIGS. 3A and 3B are flowcharts depicting an example method for manufacturing a microbiota restoration therapy composition.
Figure 3B:
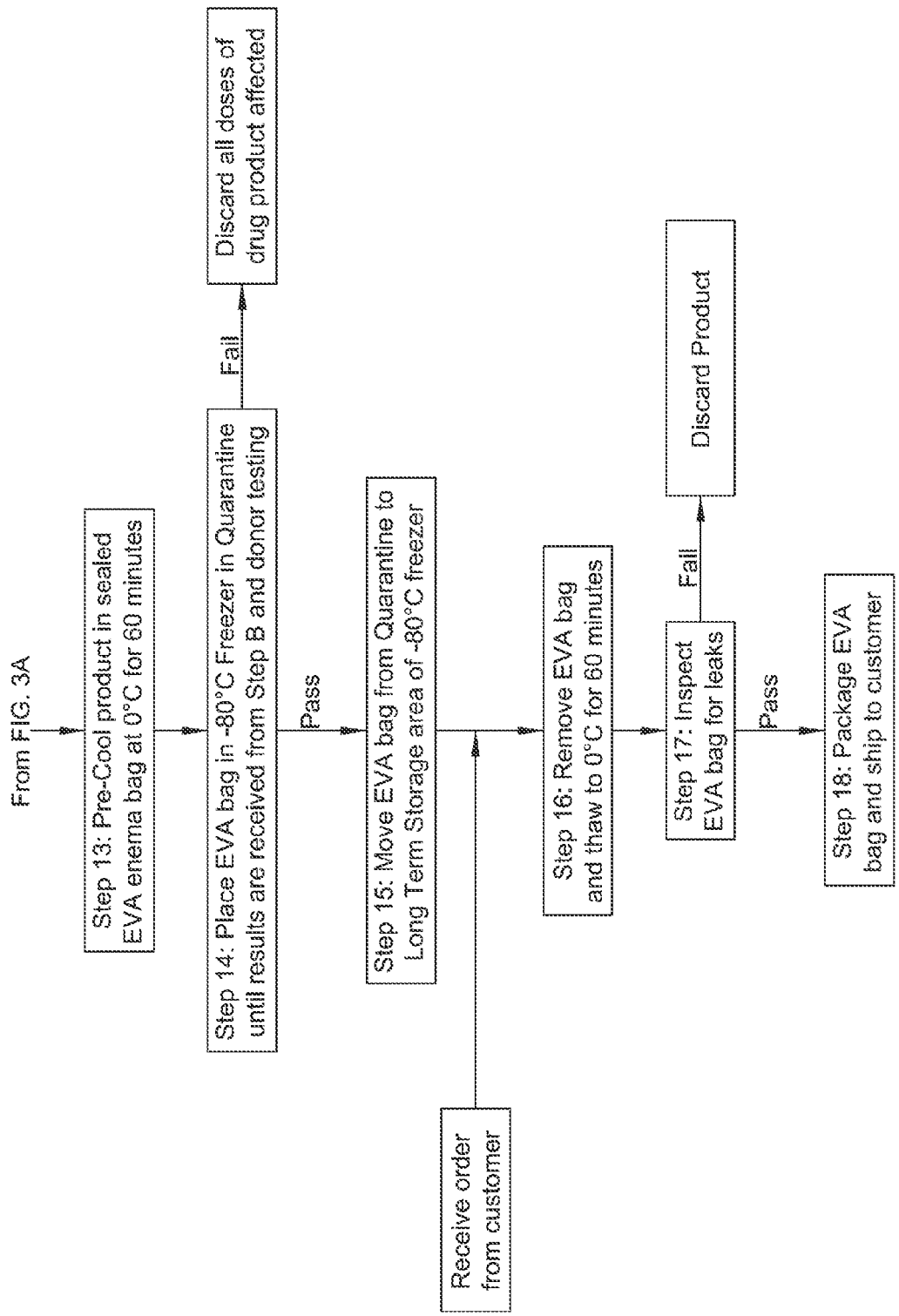

An exemplary method of processing a drug substance (MRT composition) from release from quarantine to shipment to a customer is shown in FIGS. 3A and 3B. Step one may include releasing a drug substance from quarantine, and step two may include moving the collection container to a Level II BioSafety cabinet. Step three may include taring a filter bag on a bag holder in the BioSafety cabinet on a calibrated scale, followed by weighing about 50 g±10 g of the drug substance into the filter bag in step four. Step five may include adding 3 mL/g of premixed PEG/saline solution to the drug substance in the filter bag. The premixed PEG/saline solution may be prepared in step A by reconstituting PEG powder at a concentration of 30 g/L in 0.9% sodium chloride irrigation USP. Step six may include sealing the loaded filter bag into a closure bag and sealing the closure bag. Step seven may include removing the sealed bag assembly from the BioSafety cabinet and putting the bag into a paddle mixer. In step eight the bag may be mixed in the paddle mixer at 230 rpm for 2 minutes, following by removing the bag from the paddle mixer and returning the bag to the BioSafety cabinet in step nine. In step ten, 150 mL of the filtered suspension may be pipetted into an ethylene vinyl acetate (EVA) enema bag, followed by sealing the enema bag in step eleven. A sample from the filtered suspension may be set aside for product quality testing. In step B1, CDC and BBE plates may be prepared. Step B2 may include creating serial dilutions from the remaining filtered suspension. This step is performed once per batch. In step B3 the CDC and BBE plates are inoculated with the serial dilutions and incubated for 48 hours at 37° C. In step B4 the colony forming units (CFU) per plate are counted.

The exemplary method is continued in FIG. 3B. In step thirteen, the drug product sealed in an EVA enema bag may pre-cooled at 0° C. for 60 minutes. In step fourteen the EVA bag may be placed in an −80° C. freezer in quarantine until results are received from step B and donor testing. If the drug product fails the testing, all of the affected doses of the drug product are discarded. If the drug product passes the testing, the EVA bag may be moved, in step fifteen, from quarantine to a long term storage area of the −80° C. freezer. While the drug product is stored in the −80° C. freezer, an order may be received from a customer. In step sixteen, the EVA bag may be removed from the freezer and thawed to 0° C. for 60 minutes. In step seventeen, the EVA bag may be inspected for leaks. If the bag fails the inspection, the product is discarded, and if the bag passes the inspection, the EVA bag is packaged in step 18 and shipped to the customer.

Figure 4:
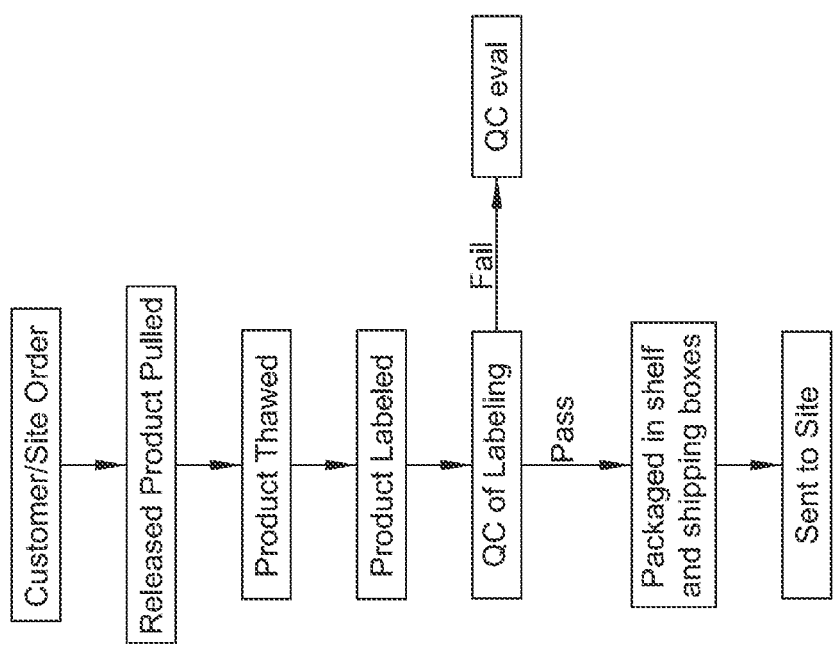
FIG. 4 is a flowchart depicting an example process for ordering and shipping a microbiota restoration therapy composition.

FIG. 4 summarizes one example of a delivery method in a flow chart. A customer or site order of an MRT product triggers a released product to be pulled from long term storage at −80° C. The site may be a doctor's office, clinic, hospital, or other location where the MRT product is to be used. The product is thawed and labeled. Quality control (QC) of the labeling process is performed, with a failure of the labeling process causing the product to be re-labeled and again passed through quality control. Passing QC moves the product to the packaging stage where the product is packaged into shipping boxes and then shipped to the site.

Figure 5:
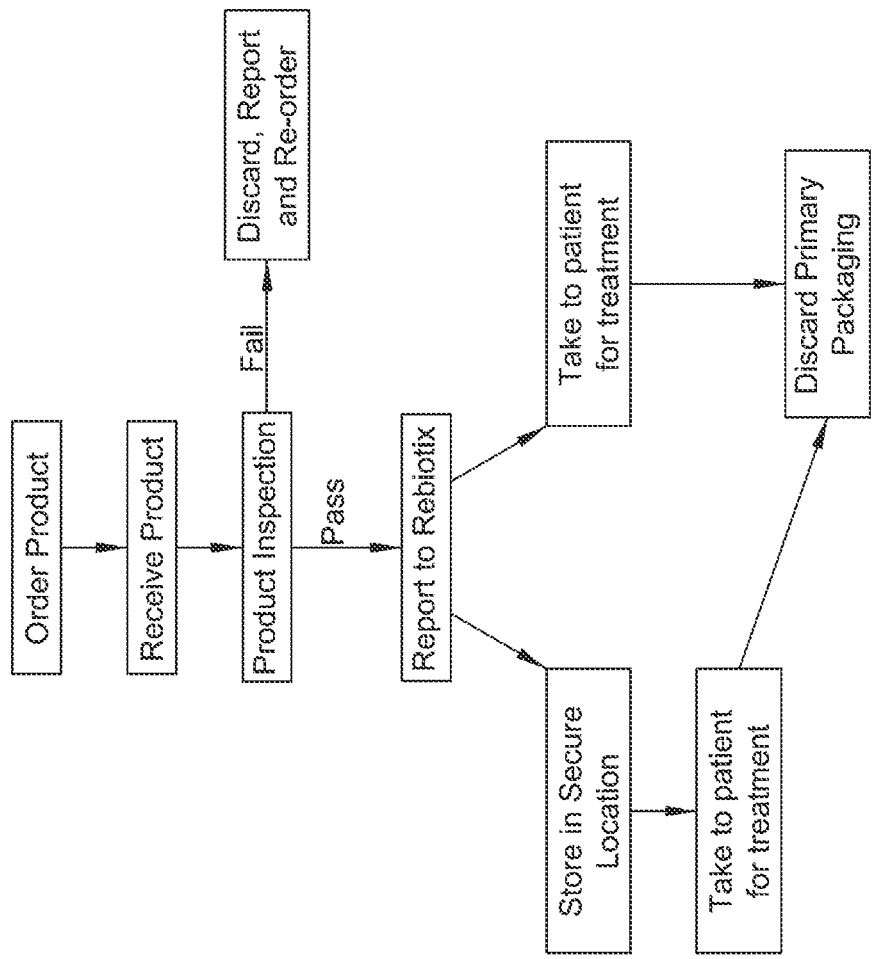
FIG. 5 is a flowchart depicting another example process for ordering and shipping a microbiota restoration therapy composition.

FIG. 5 summarizes another example of a delivery method in a flow chart. The product is ordered, received, and inspected. Failure of the product to pass inspection causes the product to be discarded, a report to be sent to the processing center, and a re-order of product to be placed. If the product passes the inspection, a report is sent to the processing center, and the product is either taken to the patient for treatment or stored in a secured location prior to being taken to the patient for treatment. In either case, the primary packaging is discarded after the product is given to the patient.

Figure 6:
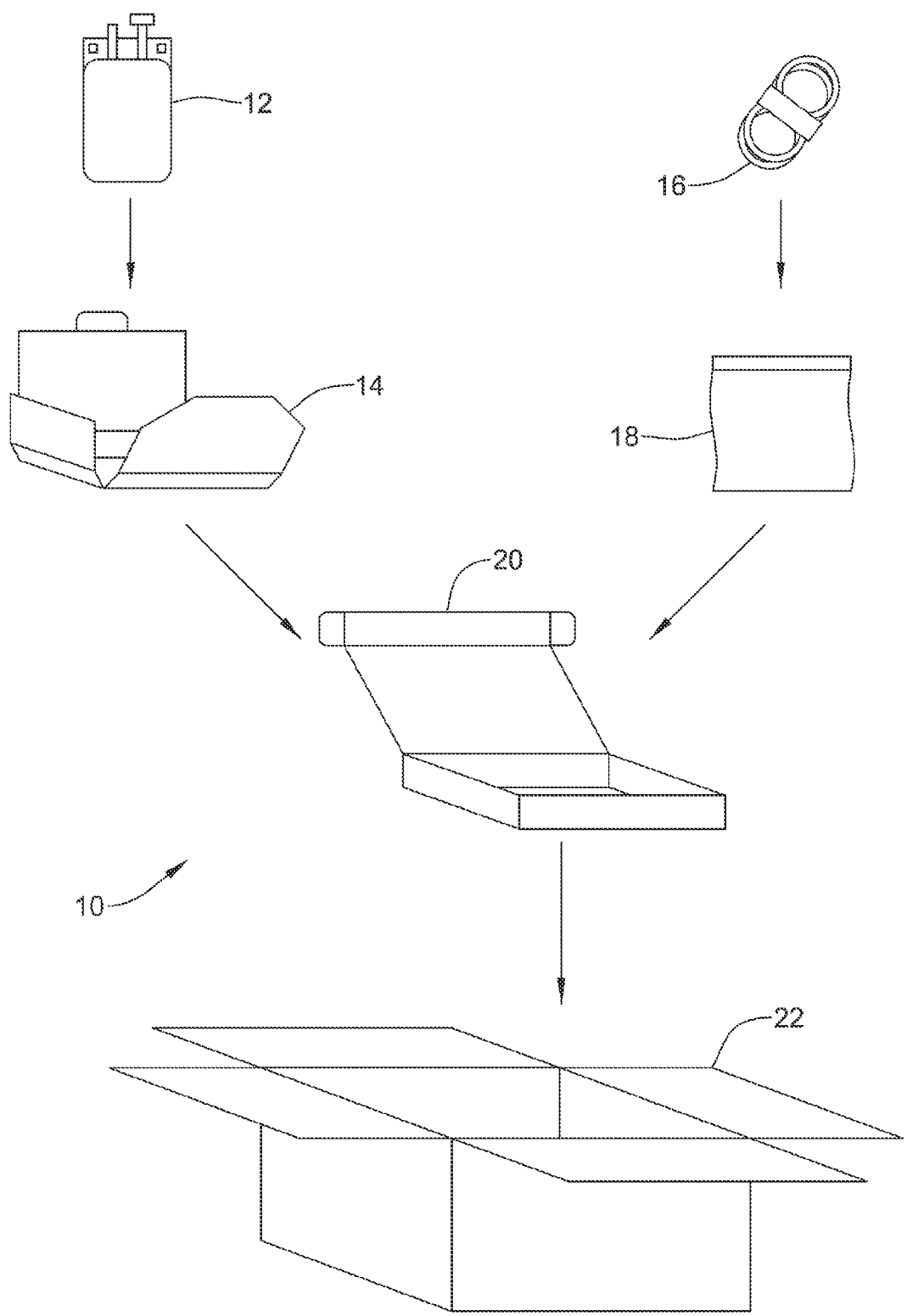
FIG. 6 is a schematic view of an example packaging system.

An example packaging system 10 is shown in FIG. 6. Packaging system 10 may include a sample bag 12. Sample bag 12 may be used to contain an MRT composition as described herein, a protective inner box 14, a tube assembly 16, a package 18 (e.g., TYVEK®) for tube assembly 16, a shelf box 20 (which will house sample bag 12, protective inner box 14, tube assembly 16 within package 18, and instructions). Shelf box 20 may be placed in an insulated shipping box 22 (e.g., which may include Styrofoam) along with ice packs and shipping box 22 may be transported to a treatment facility. Shipping box 22 may be closed and taped shut in an H-pattern to limit the exchange of air between packaging system 10 and the outside atmosphere.

Packaging system 10 was then subjected to a varying range of temperatures over an extended time period. The testing conditions included removal of sample bag 12 from a thaw bath (e.g., at 0±0.5° C.), placing packaging system 10 in a "cold" environment (e.g., −20±3° C. for 4 h±30 min), holding packing system 10 at room temperature for a first time period (22±3° C. for 8 h±30 min), placing packaging system 10 in a "hot" environment (50±3° C. for 4 h±30 min), holding packing system 10 at room temperature for a second time period (22±3° C. for 8 h±30 min), placing packaging system 10 in a "warm" environment (35±3° C. for 4 h±30 min), and holding packing system 10 at room temperature for a third time period (22±3° C. for 8 h±30 min). Under these conditions, the temperature of sample bag 12 remained below 20° C. for the entire period (approximately 36 hours). According to these test results, packaging system 10 provides suitable protection to sample bag 12 from climatic extremes anticipated for the delivery of the MRT compositions disclosed herein.

Figure 7:
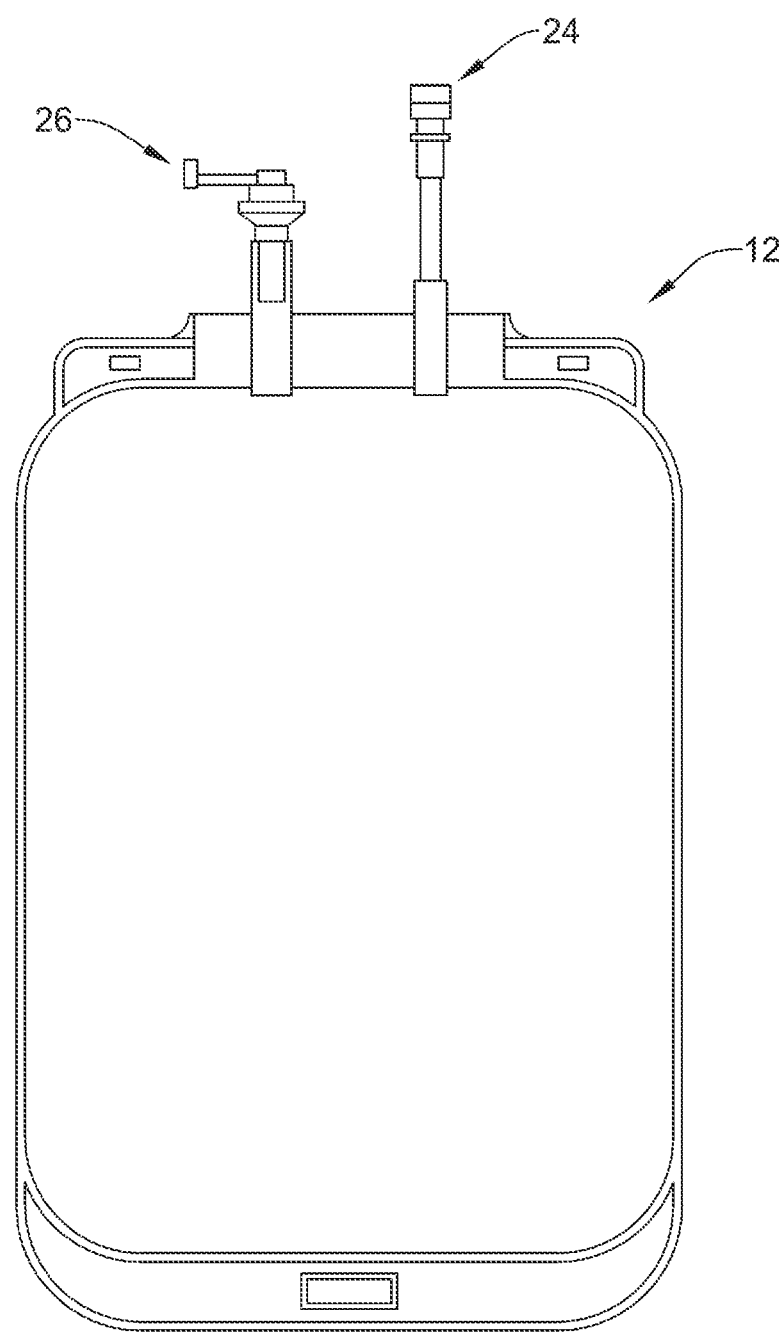
FIG. 7 illustrates an example sample bag.

FIG. 7 illustrates sample bag 12. Bag 12 may be formed from ethyl vinyl acetate. Other materials are contemplated. For example, bag 12 may include a polyethylene terephthalate polyester film, a material substantially impervious to gases, other polymers, or the like. Bag 12 may resemble an intravenous bag, and optionally bag 12 may include an attachment that will allow bag 12 to be hung on a stand, (e.g., to be positioned/hung above an endoscope).

Bag 12 may have a capacity in the range of about 25-250 ml (e.g., 50 ml). Bag 12 may have a fill port 24 for transporting the MRT composition into bag 12. Fill port 24 may include a luer or other type of adapter to facilitate transportation of the MRT composition. After filling bag 12 with the MRT composition, fill port 24 may be sealed, effectively sealing the MRT composition within bag 12. Bag 12 may also include a spike port 26. Spike port 26 may be utilized to extract the MRT composition from bag 12 at the time of use.

Figure 8:
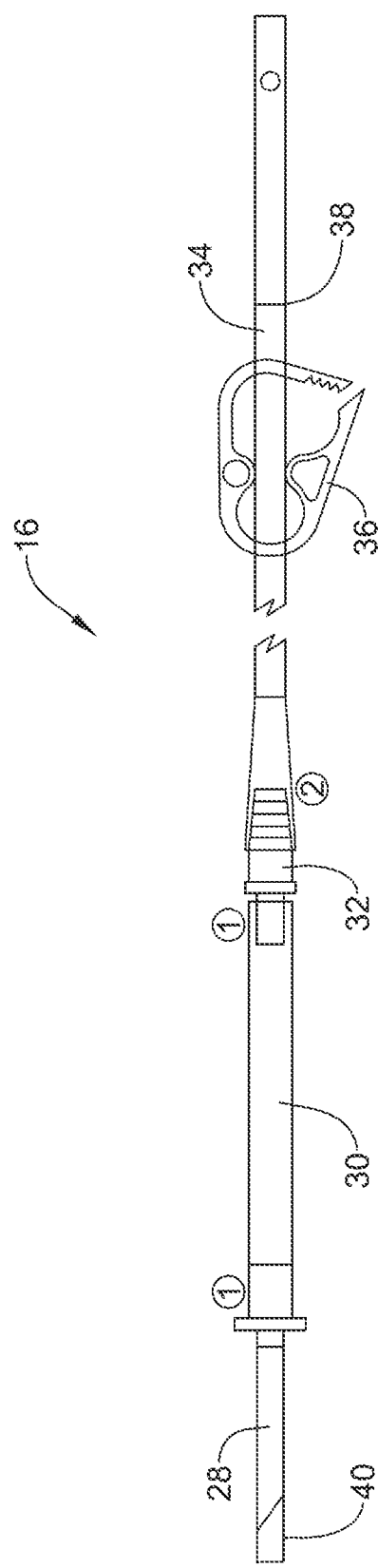
FIG. 8 illustrates an example tube assembly.

FIG. 8 illustrates tube assembly 16. Tube assembly 16 may include a spike member 28 that is designed to piece spike port 26 on bag 12. Tube assembly 16 may also include a tube body 30 with a step adapter 32. Step adapter 32 may allow tube 16 to be coupled with a delivery tube 34.

Tube assembly 16 may include a number of additional features. For example, a clamp 36 may be coupled to delivery tube 34. In addition, a visual marker 38 may also be disposed along delivery tube 34. A spike cover 40 may be disposed along spike member 28.

The MRT compositions disclosed herein are designed to remain stable over extended periods of time at various temperature conditions. For example, when stored at temperatures of approximately 20-25° C., the MRT compositions may remain stable (e.g., with a viable population of microbes) for about 24 hours or more, for about 48 hours or more, for about 96 hours or more, or for about 192 hours or more. When stored at temperatures of approximately 4° C., the MRT compositions may remain stable (e.g., with a viable population of microbes) for about 24 hours or more, for about 48 hours or more, for about 96 hours or more, for about 192 hours or more, or for about 240 hours or more. In other words, the "thawed shelf life" of the MRT compositions may be on the order of about 24 hours or more, about 48 hours or more, about 96 hours or more, about 192 hours or more, or about 240 hours or more.

When stored at temperatures of approximately −20° C., the MRT compositions may remain stable (e.g., with a viable population of microbes) for about 60-90 days or more, for about 4-6 months or more, or for about 6-9 months or more. When stored at temperatures of approximately −80° C., the MRT compositions may remain stable (e.g., with a viable population of microbes) for about 60-90 days or more, for about 4-6 months or more, for about 6-9 months or more, or for about 12 months or more. In other words, the "frozen shelf life" of the MRT compositions may be on the order of about 60-90 days or more, about 4-6 months or more, about 6-9 months or more, or about 12 months or more.

The MRT compositions of the present disclosure may include bacteria that are members of at least 1 phylum, at least 2 phyla, at least 3 phyla, at least 4 phyla, at least 5 phyla, at least 6 phyla, at least 7 phyla, at least 8 phyla, at least 9 phyla, or at least 10 phyla. In at least some embodiments, the MRT compositions of the present disclosure may include bacteria that are members of at least 1 class, at least 2 classes, at least 3 classes, at least 4 classes, at least 5 classes, at least 6 classes, or at least 7 classes. In at least some embodiments, the MRT compositions of the present disclosure may include bacteria that are members of at least 1 order, at least 2 orders, at least 3 orders, at least 4 orders, at least 5 orders, at least 6 orders, or at least 7 orders. In at least some embodiments, the MRT compositions of the present disclosure may include bacteria that are members of at least 1 family, at least 2 families, at least 3 families, at least 4 families, at least 5 families, at least 6 families, at least 7 families. In at least some embodiments, the MRT compositions of the present disclosure may include bacteria that are members of at least 5, at least 10, at least 20, or at least 30 different genera of bacteria. In at least some embodiments, the MRT compositions of the present disclosure may include at least 10, at least 50, at least 100, at least 200, at least 300, or at least 400 different species of bacteria.

For example, the MRT compositions may include viable bacteria from 1 or more orders or 2 or more orders including, but not limited to, Bacteroidales and Clostridiales. In some embodiments, about 20-95%, or about 30-85%, or about 40-60% of the viable bacterial in the MRT compositions may be from the order Bacteroidales. In some of these and in other embodiments, about 10-85%, or about 20-60%, or about 30-40% of the viable bacterial in the MRT compositions may be from the order Clostridiales.

In addition or alternatively, the MRT compositions may include bacteria from 5 or more families, or about 6-12 families, or about 7-10 families. This may include bacteria from the familes Bacteroidaceae, Burkholderiales, Clostridiaceae, Clostridiales, Eubacteriaceae, Firmicutes, Lachnospiraceae, Porphyromonadaceae, Prevotellaceae, Rikenellaceae, Ruminococcaceae, and Streptococcaceae. In some embodiments, about 20-84%, or about 30-50%, or about 36-48% of the viable bacterial in the MRT compositions may be from the family Bacteroidaceae. In some of these and in other embodiments, about 0.5-2% or about 1% of the viable bacterial in the MRT compositions may be from the family Burkholderiales. In some of these and in other embodiments, about 1-10%, or about 1-8%, or about 2-7% of the viable bacterial in the MRT compositions may be from the family Clostridiaceae. In some of these and in other embodiments, about 1-22%, or about 3-22%, or about 1-10%, or about 1-8%, or about 4-7% of the viable bacterial in the MRT compositions may be from the family Clostridiales. In some of these and in other embodiments, about 1-10%, or about 1-9%, or about 4-8% of the viable bacterial in the MRT compositions may be from the family Eubacteriaceae. In some of these and in other embodiments, about 0.5-2% or about 1% of the viable bacterial in the MRT compositions may be from the family Firmicutes. In some of these and in other embodiments, about 0.5-23%, or about 1-10%, or about 4-9% of the viable bacterial in the MRT compositions may be from the family Lachnospiraceae. In some of these and in other embodiments, about 0.5-8%, or about 1-5%, or about 1-3% of the viable bacterial in the MRT compositions may be from the family Porphyromonadaceae. In some of these and in other embodiments, about 0.5-2% or about 1% of the viable bacterial in the MRT compositions may be from the family Prevotellaceae. In some of these and in other embodiments, about 1-30%, or about 1-52%, or about 4-23% of the viable bacterial in the MRT compositions may be from the family Rikenellaceae. In some of these and in other embodiments, about 5-30%, or about 8-25%, or about 10-18% of the viable bacterial in the MRT compositions may be from the family Ruminococcaceae. In some of these and in other embodiments, about 0.5-2% or about 1% of the viable bacterial in the MRT compositions may be from the family Streptococcaceae.

The MRT compositions of the present disclosure may have a Shannon Diversity Index of about 0.4-2.5, or about 1.0-2.0, or about 1.08-1.89, or about 1.25-1.75. These numbers are calculated at the "family" level. Doing calculations at other levels (e.g., phyla, species, etc.) would result in different numbers (e.g., 1-8 or so). Therefore, the Shannon Diversity Index may be on the order of about 1-8 when calculated at the phyla, species, or other levels.

An MRT composition of the present disclosure may be administered by a method suitable for depositing in the gastrointestinal tract, preferably the colon, of a subject (e.g., human, mammal, animal, etc.). Examples of routes of administration include rectal administration by colonoscopy, suppository, enema, upper endoscopy, upper push enteroscopy. Additionally, intubation through the nose or the mouth by nasogastric tube, nasoenteric tube, or nasal jejunal tube may be utilized. Oral administration by a solid such as a pill, tablet, a suspension, a gel, a geltab, a semisolid, a tablet, a sachet, a lozenge or a capsule or microcapsule, or as an enteral formulation, or re-formulated for final delivery as a liquid, a suspension, a gel, a geltab, a semisolid, a tablet, a sachet, a lozenge or a capsule, or as an enteral formulation may be utilized as well. Compositions may be treated or untreated fecal flora, entire (or substantially entire) microbiota, or partially, substantially or completely isolated or purified fecal flora, is lyophilized, freeze-dried or frozen, or processed into a powder.

For therapeutic use in the method of the present disclosure, a composition may be conveniently administered in a form containing one or more pharmaceutically acceptable carriers. Suitable carriers are well known in the art and vary with the desired form and mode of administration of the composition. For example, they may include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier may be biologically acceptable and inert (e.g., it permits the composition to maintain viability of the biological material until delivered to the appropriate site).

Oral compositions may include an inert diluent or an edible carrier. For the purpose of oral therapeutic administration, the active compound can be incorporated with excipients and used in the form of tablets, troches, or capsules, e.g., gelatin capsules. Oral compositions can also be prepared by combining a composition of the present disclosure with a food. In one embodiment a food used for administration is chilled, for instance, ice cream. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

The active compounds can also be prepared in the form of suppositories (e.g., with conventional suppository bases such as cocoa butter and other glycerides) or retention enemas for rectal delivery. The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

A composition may be encapsulated. For instance, when the composition is to be administered orally, the dosage form is formulated so the composition is not exposed to conditions prevalent in the gastrointestinal tract before the colon, e.g., high acidity and digestive enzymes present in the stomach and/or intestine. The encapsulation of compositions for therapeutic use is routine in the art. Encapsulation may include hard-shelled capsules, which may be used for dry, powdered ingredients soft-shelled capsules. Capsules may be made from aqueous solutions of gelling agents such as animal protein (e.g., gelatin), plant polysaccharides or derivatives like carrageenans and modified forms of starch and cellulose. Other ingredients may be added to a gelling agent solution such as plasticizers (e.g., glycerin and or sorbitol), coloring agents, preservatives, disintegrants, lubricants and surface treatment.

Formulations suitable for rectal administration include gels, creams, lotions, aqueous or oily suspensions, dispersible powders or granules, emulsions, dissolvable solid materials, douches, and the like. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present disclosure may be formulated for colonic or rectal administration.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a in predetermined amount of the active compound; as powders or granules; as solutions or suspensions in aqueous or non-aqueous liquids; or as oil-in-water or water-in-oil emulsions.

Formulations suitable for transmucosal methods, such as by sublingual or buccal administration include lozenges patches, tablets, and the like comprising the active compound and, typically a flavored base, such as sugar and acacia or tragacanth and pastilles comprising the active compound in an inert base, such as gelatin and glycerine or sucrose acacia.

Formulations of the disclosure may be prepared by any suitable method, typically by uniformly and intimately admixing the pre-determined gut flora with liquids or finely divided solid carriers or both, in the required proportions and then, if necessary, shaping the resulting mixture into the desired shape. In addition, the pre-determined gut flora will be treated to prolong shelf-life, preferably the shelf-life of the pre-determined gut flora will be extended via freeze drying.

Furthermore, a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient of the present disclosure. In addition to the ingredients specifically mentioned above, the formulations of the present disclosure may include other agents known to those skilled in the art, having regard for the type of formulation in issue. For example, formulations suitable for oral administration may include flavoring agents and formulations suitable for intranasal administration may include perfumes.

The therapeutic compositions of the disclosure can be administered by any conventional method available for use in conjunction with pharmaceutical drugs, either as individual therapeutic agents or in a combination of therapeutic agents. The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

Ointments, pastes, foams, occlusions, creams and gels also can contain excipients, such as starch, tragacanth, cellulose derivatives, silicones, bentonites, silica acid, and talc, or mixtures thereof. Powders and sprays also can contain excipients such as lactose, talc, silica acid, aluminum hydroxide, and calcium silicates, or mixtures of these substances.

Formulations suitable for rectal administration may be presented as suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate. Suitable pharmaceutical carriers are described in Remington's Pharmaceutical Sciences, Mack Publishing Company, a standard reference text in this field.

The dose administered to a subject, especially an animal, particularly a human, in the context of the present disclosure should be sufficient to affect a therapeutic response in the animal over a reasonable time frame. One skilled in the art will recognize that dosage will depend upon a variety of factors including the condition of the animal, the body weight of the animal, as well as the condition being treated. A suitable dose is that which will result in a concentration of the therapeutic composition in a subject that is known to affect the desired response.

The size of the dose also will be determined by the route, timing and frequency of administration as well as the existence, nature, and extent of any adverse side effects that might accompany the administration of the therapeutic composition and the desired physiological effect.

It will be appreciated that the compounds of the combination may be administered: (1) simultaneously by combination of the compounds in a co-formulation or (2) by alternation, i.e. delivering the compounds serially, sequentially, in parallel or simultaneously in separate pharmaceutical formulations. In alternation therapy, the delay in administering the second, and optionally a third active ingredient, should not be such as to lose the benefit of a synergistic therapeutic effect of the combination of the active ingredients. According to certain embodiments by either method of administration (1) or (2), ideally the combination should be administered to achieve the most efficacious results. In certain embodiments by either method of administration (1) or (2), ideally the combination should be administered to achieve peak plasma concentrations of each of the active ingredients.

It will be appreciated by those skilled in the art that the amount of active ingredients in the combinations of the disclosure required for use in treatment will vary according to a variety of factors, including the nature of the condition being treated and the age and condition of the patient, and will ultimately be at the discretion of the attending physician or health care practitioner. The factors to be considered include the route of administration and nature of the formulation, the animal's body weight, age and general condition and the nature and severity of the disease to be treated.

The sample drug composition may be packaged into a shelf box and then packaged into an insulated corrugated box for shipment to the customer at the time of order. The sample drug composition is shipped after thawing to 0° C. from the −80° C. long term storage freezer. To ensure that the liquid suspension is adequately protected from fluctuations in temperature during shipment, the packaging system was subjected to varying temperatures over a 24-hour period. The design for this testing process was adapted from the ASTM International F2825-10, Standard Practice for Climatic Stressing of Packaging Systems for Single Parcel Delivery. The goal of the testing was to ensure that the product did not experience temperatures below an acceptable threshold (32° F. or 0° C.) or exceed an acceptable threshold (84° F. or 29° C.)

The product may be administered to patients having a variety of different medical conditions and may desirably impact these conditions. Some of the medical conditions that may be desirably impacted by include cardiovascular and/or peripheral vascular disease, allergies, obesity, hypoglycemia, constipation, celiac sprue (e.g., celiac disease), gastrointestinal cancer (e.g. gastrointestinal cancer is at least one of stomach cancer, esophageal cancer, colon cancer gallbladder cancer, liver cancer, pancreatic cancer, colorectal cancer, anal cancer, and gastrointestinal stromal tumors), myoclonus dystonia, sacrolileitis, spondyloarthropatliy, spondylarthritis, proximal myotonic myopathy; an autoimmune disease nephritis syndrome, autism, travelers' diarrhea, small intestinal bacterial overgrowth, chronic pancreatitis, a pancreatic insufficiency, chronic fatigue syndrome, benign myalgic encephalomyelitis, chronic fatigue immune dysfunction syndrome, Parkinson's Disease (PD), amyotrophic lateral sclerosis (ALS), multiple sclerosis (MS), degenerative neurological diseases, Grand mal seizures or petitmal seizures, Steinert's disease, chronic infectious mononucleosis, epidemic myalgic encephalomyelitis, idiopathic thrombocytopenic purpura (ITP), an acute or chronic allergic reaction obesity, anorexia, irritable bowel syndrome (IBS or spastic colon) Crohn's disease, irritable bowel disease (IBD), colitis, ulcerative colitis or Crohn's colitis, chronic infectious mononucleosis, epidemic myalgic encephalomyelitis, acute or chronic urticarial, lupus, rheumatoid arthritis (RA) or juvenile idiopathic arthritis (JIA), pre-diabetic syndrome, fibromyalgia (FM), Type I or Type II diabetes, acute or chronic insomnia, and attention deficit/hyperactivity disorder (ADHD).

In the case of humans, the present disclosure encompasses methods of treatment of chronic disorders associated with the presence of abnormal enteric microflora. Such disorders include but are not limited to those conditions in the following categories: gastro-intestinal disorders including irritable bowel syndrome or spastic colon, functional bowel disease (FBD), including constipation predominant FBD, pain predominant FBD, upper abdominal FBD, nonulcer dyspepsia (NUD), gastro-oesophageal reflux, inflammatory bowel disease including Crohn's disease, ulcerative colitis, indeterminate colitis, collagenous colitis, microscopic colitis, chronic *Clostridium difficile* infection, pseudomembranous colitis, mucous colitis, antibiotic associated colitis, idiopathic or simple constipation, diverticular disease, AIDS enteropathy, small bowel bacterial overgrowth, coeliac disease, polyposis coil, colonic polyps, chronic idiopathic pseudo obstructive syndrome; chronic gut infections with specific pathogens including bacteria, viruses, fungi and protozoa; viral gastrointestinal disorders, including viral gastroenteritis, Norwalk viral gastroenteritis, rotavirus gastroenteritis, AIDS related gastroenteritis; liver disorders such as primary biliary cirrhosis, primary sclerosing cholangitis, fatty liver or cryptogenic cirrhosis; rheumatic disorders such as rheumatoid arthritis, non-rheumatoid arthritidies, non rheumatoid factor positive arthritis, ankylosing spondylitis, Lyme disease, and Reiter's syndrome; immune mediated disorders such as glomeruionephritis, haemolytic uraemic syndrome, juvenile diabetes mellitus, mixed cryoglobulinaemia, polyarteritis, familial Mediterranean fever, amyloidosis, scleroderma, systemic lupus erythematosus, and Behcets syndrome; autoimmune disorders including systemic lupus, idiopathic thrombocytopenic purpura, Sjogren's syndrome, haemolytic uremic syndrome or scleroderma: neurological syndromes such as chronic fatigue syndrome, migraine, multiple sclerosis, amyotrophic lateral sclerosis, myasthenia gravis, Gillain-Barre syndrome, Parkinson's disease, Alzheimer's disease, Chronic Inflammatory Demyelinating Polyneuropathy, and other degenerative disorders; sychiatric disorders including chronic depression, schizophrenia, psychotic disorders, manic depressive illness; regressive disorders including, Asbergers syndrome, Rett syndrome, attention deficit hyperactivity disorder (ADHD), and attention deficit disorder (ADD); the regressive disorder, autism; sudden infant death syndrome (SIDS), anorexia nervosa; dermatological conditions such as chronic urticaria, acne, dermatitis herpetiformis and vasculitis disorders; and cardiovascular and/or vascular disorders and diseases.

EXAMPLES

The disclosure may be further clarified by reference to the following Examples, which serve to exemplify some embodiments, and not to limit the invention in any way.

Example 1

Confirmation of Sample Characterization Methods

Tests were completed to confirm the methods for characterizing a normal human stool sample. A Measurement Systems Analysis (MSA) was conducted to identify the components of variation in the test measurement described above. To do this, 5 healthy human donors of different ages, genders, and body mass were recruited. Stool samples were collected from each donor, and processed according to predetermined standard methods. The resultant bacterial suspensions were plated and grown on the two different plates described above (the CDC and the BBE plates).

The variables tested included: 5 different donors, 3 liquid to human stool ratios, 2 plate types, 4 dilution levels per plate, 6 plates per dilution level, double counts (used to calculate error attributed to human plate counters), a total of 550 plates counted twice, and 20 runs (sets of plates).

The test measurements were analyzed with nested Gage R&R (repeatability and reproducibility) using Minitab 15 statistical software and the error bands were evaluated. The test process was determined to be repeatable and reproducible within specified error bands. While it was recognized that not all microbes can be cultured and counted, this method demonstrates that a representative subset of microbes in the bacterial suspension can be used as indicators of normal healthy human stool samples.

Example 2

Enema Bag and Port Durability

Three ethylene vinyl acetate (EVA) bags similar to sample bag 12 were tested to evaluate the durability of the ports when frozen at −80° C. Temperatures and time were used per manufacturing procedure to simulate future product production and handling. The bags were tested for leakage pre-freeze, pre-thaw and post-thaw. The bags were filled with 100 mL of saline solution and the ports were sealed. To determine if the seals along the edges of the bags were leaking, the bags were inverted to determine if ports were completely sealed. The bags were placed in a 0° C. cooling bath for one hour, then placed in a −80° C. freezer for one month in varying orientations. Bag sample A was placed flat, bag sample B was placed on a long side, and bag sample C was placed on a short side. After one month, the bags were removed from the −80° C. freezer and inspected for ruptures, cracks, and leaks. Additionally, a drop test was conducted by dropping the frozen EVA bags on corners, faces, and ports from a height of 36 inches. Drop testing included dropping the samples on corners, ports, and flat surfaces of the product to simulate potential handling errors when removing future product from storage. The bags were then re-inspected after each drop with the above criteria. Each drop test was repeated three times per sample except for the initial inspection of the bag perimeter seal. All the sample bags passed all the tests (no leaking was detected).

The bags were then subjected to a thaw process. Each sample was submerged in a glycerol/water bath for 1 hour at 0° C. Samples were then removed, dried, and drop testing was repeated. Again, all the sample bags passed all the tests (no leaking was detected).

Example 3

Clinical Study

An MRT composition as disclosed herein was administered to 31 subjects in a Phase 2 clinical study. No serious adverse events were reported, and no adverse events were associated with the product or its administration. Of the subjects, 27 subjects experienced successful resolution of their rCDAD (recurrent *clostridium difficile* associated diarrhea) symptoms after receiving either one or two doses of the MRT composition, defined by no recurrence of rCDAD symptoms for 56 days following administration. Of these 27 subjects, 16 experienced complete resolution of rCDAD after receiving one dose of the MRT composition, with the other 11 subjects recurring after the first administration, but then successfully reaching the 56-day efficacy endpoint following a second administration of the MRT composition. Of these subjects, 4 subjects were considered treatment failures: 3 subjects experienced recurrence of rCDAD after receiving their second dose of the MRT composition, and 1 subject recurred after the first dose and did not receive a second administration.

Doses of the MRT composition were randomly selected from the available manufactured clinical batches. The doses that were administered reflect product made from four donors. None of the product attributes (dose mass, viable microbes, shelf-life, thawed shelf-life, etc.) appear to correlate with the clinical outcome, or can be used to predict if a dose will result in a successful outcome. The clinical result information is provided at the end of this ID.

Information on the MRT composition doses administered in the Phase 2 clinical study:

45 doses of the MRT composition were thawed, shipped, and dosed to human patients. The age of the dose (AD) (which is the date of manufacture of the doses to date of administration to the clinical patient) are represented. The statistics associated with the several attributes of the MRT composition are provided below:

AD Average time=43.2 hours
AD Standard Deviation=14.9 hours
AD Minimum time=22.1 hours
AD Maximum time=73.8 hours There appears to be no correlation or detriment to the clinical outcome (resolution of recurrent *clostridium difficile* associated diarrhea) and these product attributes.

Example 4

Selection of a Cryoprotectant

The use of a cryoprotectant, in particular polyethylene glycol (PEG), has been found to maintain the viability (as determined by CFUs on CDC and BBE plates) of the MRT composition after freezing and re-thawing. This includes the time period from thawing, shipping in a controlled temperature package and allowing for time from opening until treating a patient. As with the quality testing above, the final acceptable count ranges for MRT products prior to being frozen can be between about 30 to about 300 CFU at dilution level $10^{-6}$ on the CDC plates, and from about 30 to about 300 CFU at dilution level $10^{-5}$ on the BBE plates. One method of assuring that viability is maintained is the requirement of the end user or customer, including, but not limited to, a physician or clinician, to use the product within 48 hours of receiving the product. Additionally, the end user will be required to store the product between about 2 and about 29° C. until use.

The addition of a cryoprotectant was analyzed from two perspectives. First, several cryoprotectants were screened to evaluate the initial effect of the addition of the cryoprotectant to the MRT product. This testing was used to determine mortality or viability of the MRT product when mixed with a particular cryoprotectant. The second perspective analyzed was the actual freeze protection capability of a particular cryoprotectant on the MRT product when the MRT product was frozen and then re-thawed for delivery to the patient. The result of this culturing indicated how viable the product remained after freeze/thaw.

Tests were completed to explore the effects of adding a variety of different potential MRT cryoprotectants to a homogenized and filtered human stool mixture (or MRT product). The tests were intended only to quantify the response of the bacteria to the initial addition of the cryoprotectant, and did not include testing whether the cryoprotectant was successful in protecting the bacteria through a subsequent freeze-thaw cycle. In these tests, single human stool donations were split among various tests, with a "control" sample of only normal, isotonic saline (i.e., no cryoprotectant added) used for a baseline. Both CDC plates and BBE plates were used. For all tests, a weighted average of CFU counts that combined the results of two different dilution levels was used. The cryoprotectants used included: 10% skim milk, 5% glycerol, 10% glycerol, 10% DMSO and polyethylene glycol (PEG) at molecular weights ranging from 600 to 20000.

For the CDC plates: 10% skim milk, 10% glycerol, and PEG all performed reasonably well, with CFU counts staying within approximately 25% of the saline control. Of note, higher concentrations of glycerol resulted in considerable microbe mortality in a dose-dependent relationship.

For the BBE plates: Only the PEG formulations did not show significant microbe mortality. Of note, the 10% glycerol formulations yielded nearly 90% mortality (10% survival), and the higher concentrations of glycerol yielded 100% mortality (as seen using the current dilution levels).

Given the results from the BBE plates of 10% glycerol, an additional investigation was performed to see if the 90% mortality (on the BBE plate) from adding the glycerol could be eliminated. It was hypothesized that decreasing the glycerol concentration to 5%, or chilling the microbial mixture prior to addition of the glycerol (to slow metabolic activity) could reduce the anticipated high mortality. The 5% glycerol solution had less mortality than the 10%, and cooling also decreased the mortality in a dose-dependent relationship. However, these effects were not strong enough to overcome the baseline results, and mortality of at least 60% was seen on all tests in glycerol versus the control.

Maintaining the viability of microbes in a MRT product is critical from time of human stool collection to time of giving the MRT product dose to a patient. Therefore, it is important that the cryoprotectant added not have a significant toxic effect on the microbes when initially added. Of the cryoprotectants tested, only the PEG formulations performed well. Skim milk did not perform particularly well with respect to the BBE results. Additional drawbacks for the use of milk include the potential for increasing the chance of allergic reaction and the variable characterization profile of milk. Likewise, DMSO did not perform well on the BBE plates. In addition, while DMSO is used topically in medicinal applications, there are currently no known uses in the human gastrointestinal system. 10% glycerol performed well on the CDC plates, but exhibited 80-90% mortality (10-20% survival) on the BBE plates.

Example 5

Additional Cryoprotectants

Human gut microbiota were extracted from human stool into an aqueous saline containing a number of different potential cryoprotectants at a specific concentration. These solutions were tested for pH and cultured on CDC and BBE agar plates to measure the viable microbial load, then were frozen at –80 C for between 1 to 7 days, and then thawed. A sample from the thawed solution was then tested for pH and cultured on CDC and BBE agar plates to measure the viable microbial load. Cryoprotectants with a screen result of "++" showed significantly greater viability results compared to PEG3350 (and glycerol), those with "+" had results considered at least as good as glycerol, those with "0" had mixed results and may or may not be suitable cryopreservatives, and those with "–" performed worse than glycerol and should not be considered effective cryopreservatives for human gut microbiota solutions. The results, based on pH measurements and enumeration of viable microbes using CDC and BBE agar plates suggested the following: dextrose, betaine, glycine, sucrose, polyvinyl alcohol, and Pluronic F-127 in DMSO had a result scored as "++". Mannitol, tween 80, ethylene glycol, 1,3-propanediol, hydroxypropyl cellulose, glycerol, PEG/glycerol mix, and propylene glycol had a result scored as "+". Propylene glycol (3% w/v) and fish oil had a result scored as "0". Magnesium hydroxide, urea, and xanthan gum had a score of "–+". The scoring of "–+" is used to denote that the pH was found to be not acceptable but that plating results were found to be acceptable.

Example 6

Example Production Process

Tests were completed to simulate an exemplary entire production process wherein a processed sample of human stool (diluted, homogenized, and filtered) is cooled, frozen for long-term storage, thawed, shipped to a customer site, and warmed to body temperature prior to retention enema. The production process simulated a nominal process for collection of human stool; dilution of human stool directly into a cryoprotection solution (or diluent or saline/PEG mixture) at a 2:1 to a 4:1 ratio; nominal homogenization and filtration process; chilling of packaged product in a circulating fluid bath; long-term frozen storage; warming of packaged product in a circulating fluid bath; packaging of product for shipment with "cold packs" and in insulating materials; overnight shipping to customer; bedside warming of product for immediate infusion into patient. As part of the study, three parameters were varied to explore their effects on overall microbial viability or survival (as measured by serial dilution onto CDC and BBE plates for incubation and counting of CFUs). These parameters included the use of a cryoprotectant, temperature of a chilling bath, and temperature of a thawing bath.

For cryoprotectant testing, the study included samples with no cryoprotectant (normal saline); 10% glycerol and PEG 3350 at 59 g/liter. For testing the use of a cooling bath, the study included samples that went directly into a freezer (−80° C.), and therefore, were not subjected to a cooling bath, samples that went directly into a 0° C. cooling bath, and samples that went directly into a −11° C. cooling bath. The warming was tested at 0° C., +10° C., and +20° C. Each test permutation was normalized to a control sample that used the same cryoprotectant, but plated immediately and NOT subjected to any of the freeze-thaw processes.

The cryoprotectants, if used, were mixed with normal saline and added during the homogenization process (see definition of diluent and saline/PEG mixture). Thus, any microbial mortality due to addition of the cryoprotectant (for example, such as has been seen with glycerol, especially in the BBE plates) will only be observed by comparing the CFUs of the control samples.

It was found that the freezing and thawing parameters had little effect on overall microbial survival. This is generally clear for the CDC plates, where the data is generally well behaved and the results, for all the freeze-thaw parameters, vary only well within a single log-level of dilution. For the BBE plates, the raw data was much less well behaved, with several instances of apparent outliers and cases where the 10× rule comparing adjacent dilution levels (i.e., log levels) was violated. However, there was still not an apparent difference due to the freeze-thaw parameters.

Effects due to the different cryoprotectants used were clearly observed. For this analysis, a simple arithmetic mean of the results from the different freeze-thaw parameters was used to compare cryoprotectant performance. For the CDC plates, "no cryoprotection" had an 18% survival (82% mortality) through freeze-thaw, while the addition of glycerol and PEG reduced this mortality something on the order of 30% (67% and 75% survival, respectively). With respect to the samples treated with glycerol, the above results neglect the mortality from the initial addition of the glycerol. When the initial addition of the cryoprotectant is added to the effects of the freeze/thaw, the magnitude of this effect was around 80% mortality. This was compared to about 32% mortality for sample using PEG as cryoprotectant.

On BBE plates, the effect of adding glycerol was very high mortality at 80% to 90%. In counterpoint, the PEG plates showed either low or no initial toxicity from the cryoprotectant and a strong preservative effect through the freeze-thaw cycle. Overall cumulative survival using PEG is 75% versus control (25% mortality). It was concluded that 10% glycerol performs poorly on BBE plates, based on the combination of initial mortality and freeze-thaw losses being on the order of 1-log loss (10% survival). The PEG-3350 performs well on both CDC and BBE plates. The PEG has low initial toxicity to the microbes (little or no losses from addition of the cryoprotectant to the human stool) and it offers significant protection versus "no cryoprotectant". It is anticipated that each dose of MRT will have a minimum of $10^7$ microbes/mL of suspension, with a minimum of 100 mL of suspension delivered per dose.

Example 7

Fecal Transplant Kit

In an example, a kit of parts can be created to aid in fecal transplant. In an example, a donation kit can be shipped to a clinician. The donation kit can include equipment for blood and fecal samples from the patient or, in certain examples, a healthy donor. Because much of the patient's gut microbiota is anaerobic, many organisms can die with exposure to air. In an example, the donation kit can include materials to ship the blood and fecal samples without harming the samples (e.g., quick freeze, dry ice, etc.).

Once shipped to a facility (e.g., one location, regional locations, many locations, etc.), the samples can be tested, and *Clostridium difficile* or the presence or absence of one or more other diseases or conditions can be confirmed. In other examples, a healthy fecal sample can be tested and prepared for use as a treatment.

In an example, once the patient's samples are tested to verify the disease or condition, or the donor's samples are tested to verify health or other compatibility (e.g., the existence of one or more desired condition, etc.), a treatment can be prepared (e.g., using the healthy donor fecal sample, at least a portion of one or more healthy stored fecal samples, such as material from a fecal bank, etc.) and shipped back to the clinician for delivery to and treatment of the patient. In certain examples, the treatment is preserved (e.g., frozen, etc.) during shipping. The kit can include the processed fecal sample or treatment in a sterile container, such as a nasogastric (NG) tube, a vial (e.g., for use with a retention enema), a gastro-resistant capsule (e.g., acid-bio resistant to reach the intestinal tract, having a sterile outside), etc. In an example, once received, the clinician can store the contents in a manner to preserve the microbiota until ready to be inserted into the patient.

Example 8

Extended Shelf Life Formulations

The long-term storage of the survivability of the healthy human microbial content of donor stool was studied. Stool samples were processed with and without a cryoprotectant and cooled/thawed at varying controlled temperatures. Samples were then removed after 360 days (12 months) of storage at −80° C. and −20° C., thawed at controlled temperatures and plated on two types of agar plates (Center for Disease Control 5% Blood Agar (CDC) and *Bacteroides* Bile Esculin Agar (BBE) respectively). The overall Colony Forming Unit per milliliter (CFU/mL) was recorded and analyzed. From the study, samples preserved without cryoprotectant were analyzed first, followed by samples preserved with varying concentrations of different cryoprotectants.

CDC plate counts grown from "No Cryoprotectant" samples demonstrated that freezer temperature and storage time had significant impact on the recoverable CFU numbers. These data are consistent with data recorded at previous time points. In this model, the $R^2$ values indicate that approximately 59% of the variation (Adj. $R^2$) in the data is explained by the model, a drop from approximately 80% demonstrated by the model after 180 days (6 months) of storage.

When stored at −20° C., most of the samples produced CFU/mL counts which fell below the lower limit considered acceptable for product specification ($10^8$ CFU/mL). In contrast, samples stored at −80° C. demonstrated counts that remained above the desired lower limit for product specification. From this, it was concluded that long-term storage of samples prepared without the use of a cryoprotectant and stored at −80° C. was found to result in greater viability when compared to samples stored at −20° C.

For the data collected from samples stored with cryoprotectant, the storage time and freezer temp were the most significant factors for the CDC counts response in CFU/mL. Most of the variation seen in the data is explained by storage time, freezer temp, and the interaction between these, as can be seen by the $R^2$ values obtained at 0.59.

Samples combined with cryoprotectants and stored at −20° C. continued to demonstrate a more significant decrease in recoverable CFU/mL. Sample runs begin to fall below the $10^8$ product specification limit between 60 and 90 days (2 and 3 months) for samples stored at −20° C. The rate of decrease in amount of recoverable CFU/mL slows beyond 60 days (2 months) of storage. However, at −80° C. storage temperature, the recoverable CFU/mL counts remain relatively stable through 270 days (9 months) of storage. Additionally, most counts remained above the minimum product specification limit of $10^8$ CFU/mL.

Storing samples at a lower freezer temperature and for less time has a positive effect on the counts—as time progresses further from the point of manufacture, a reliable recovery of CFU/mL indicating the viable microbial population of the product becomes more difficult to guarantee. However, data suggests that the effect of storage time can be dampened with the addition of PEG 3550 as a cryoprotectant, as well as storing the material at a low temperature (in this case, −80° C.).

Example 9

Extended Shelf Life Formulations

Human stool was processed as disclosed herein; an initial sample of the processed suspension was used to create serial dilutions for inoculation of agar plates. Once the sample was removed from the suspension, the remaining suspension (approx. 150 mL) was transferred to two (2) separate sterile EVA storage bags. Each bag was frozen at −80° C. for one week.

After one week, the bags were removed from the freezer and thawed per the MRT composition batch protocol. The bags were sampled to measure the immediate post-freeze recoverable CFU/mL count and diversity; each sample was serially diluted and plated on CDC and BBE plates. The bags were then stored at two different temperatures, 4° C. and 25° C., and sampled every 24 hours for 192 hours total.

Samples at each time point were also tested by a contract laboratory for biodiversity by using 16s rRNA methodology. For each sample, RNA is extracted from the bacterial cells and replicated ("amplified") using a tag primer made from of a series of base pairs needed to initiate RNA replication. After the RNA is amplified, the sequences are denoised—a process which determines the statistical probability of a correctly or incorrectly paired nucleotide set—and used to identify each organism using BLASTn software from the National Center for Biotechnology Information (NCBI) sequence library. Identity of the organisms found in each sample is determined by the length of the sequence containing the most consecutive statistically probably base pairs in a sample. The final numbers (direct counts and percentages of identified organisms from phyla to species if applicable) are then reported to Rebiotix for use in determining the change in biodiversity over time in each sample.

The product undergoes an initial drop in recoverable CFU/mL on both CDC and BBE plates once removed from the freezer and thawed (t=0 hour time point), consistent with observations from prior studies conducted by Rebiotix (P-006, P-007, P-009, P-012).

The thawed product held at 25° C. maintained a higher overall recoverable CFU/mL count than material stored at 4° C. over 192 hours.

Recoverable CFU/mL counted on all CDC plates, regardless of overall count, were considered "stable" at both temperatures throughout the experiment based on the Rebiotix measurement system (P-001). The CFU/mL results at both storage temperatures stayed within one log from the initial count at thaw to 192 hours.

Recoverable CFU/mL counted on BBE plates demonstrated an increase in recoverable CFU/mL when stored at 25° C. compared to the original pre-freeze sample over the course of 192 hours of storage. At 4° C., however, the recoverable CFU/mL maintained an unchanging (less than one log change) count throughout the 192 hour hold time.

Thawed product at both temperatures met Rebiotix product release specification throughout the 192 hour hold time, regardless of a gain or loss in CFU/mL count:

CDC post-freeze microbial load specification: $10^7$ to $10^{14}$ CFU/mL

BBE post-freeze microbial load specification: $10^5$ to $10^{14}$ CFU/mL

Results currently collected from this study indicate that recoverable phenotypic diversity on the CDC plates most closely matches the original sample diversity prior to freezing when product is stored at 25° C. post-thaw. In addition, both samples met the Rebiotix product release specification for diversity over time of ≥3 unique colony phenotypes.

Genetic biodiversity characterization (16s rRNA) of the samples is conducted by a contract laboratory examining the total bacterial types (to species if possible) as well as the percent concentrations of these types of bacteria present in the samples over time.

Preliminary understanding of product behavior during a holding period of up to 192 hours at two different temperatures continues to meet Rebiotix product release standards of CFU/mL per when used to inoculate CDC and BBE plates. More work is needed to confirm these findings. 16s rRNA data of each time point is currently under analysis.

Example 10

16s rRNA Data

The present disclosure provides compositions that include fecal microbes. As used herein, the term "fecal microbes" refers to microorganisms that are present in the gut, intestine, or colon, preferably colon, of a normal healthy adult human. Such a composition may be prepared by processing fecal material as disclosed herein. As used herein, the term "fecal material" refers to human stool. Unprocessed fecal material contains non-living material and biological material. The "non-living material" may include, but is not limited to, dead bacteria, shed host cells, proteins, carbohydrates, fats, minerals, mucus, bile, undigested fiber and other foods, and other compounds resulting from food and metabolic waste products and partial or complete digestion of food materials. "Biological material" refers to the living material in fecal material, and includes microbes including prokaryotic cells such as bacteria and archea (e.g., living prokaryotic cells and spores that can sporulate to become living prokaryotic cells), eukaryotic cells such as protozoa and fungi, and viruses. "Biological material" may also refer to the living material (e.g., the microbes, eukaryotic cells, and viruses) that are present in the colon of a normal healthy human. Examples of prokaryotic cells that may be present in a composition of the present disclosure include cells that are members of the class Actinobacteria, such as the subclass Actinobacteridae or Coriobacteridae, such as the order Bifidobacteriales or Coriobacteriales, and/or such as the family Bifidobacteriaceae or Coriobacteriaceae; members of the phylum Bacteroidetes, such as class Bacteroidia, such as class Bacteroidales, and/or such as family Bacteroidaceae or Rikenellaceae; members of the phylum Firmicutes, such as class Bacilli, Clostridia, or Erysipelotrichi, such as order Bacillales or Lactobacillales or Clostridales or Erysipelotrichales, and/or such as family Paenibacillaceae or Aerococcaceae or Lactobacillaceae or Streptococcaceae or Catabacteriaceae or Peptococcaceae or Peptostreptococcaceae or Ruminococcaceae or Clostridiaceae or Eubacteriaceae or Lachnospiraceae or Erysipelotrichaceae; members of the phylum Proteobacteria, such as class Alphaproteobacteria or Betaproteobacteria or Gammaproteobacteria, such as order Rhizobiales or Burkholderiales or AJteromonadales or Enterobacteriales, and/or such as family Rhodobiaceae or Burkholderiaceae or Shewanellaceae or Enterobacteriaceae; members of the phylum Tenericutes, such as the class Mollicutes, such as the order Entomoplasmatales, and/or such as the family Spiroplasmataceae; and/or members of the class Verrucomicrobiae, such as the order Verrucomicrobiales, and/or such as the family Verrucomicrobiaceae. These are just examples.

The MRT compositions of the present disclosure may include bacteria that are members of at least 1 phylum, at least 2 phyla, at least 3 phyla, at least 4 phyla, at least 5 phyla, at least 6 phyla, at least 7 phyla, at least 8 phyla, at least 9 phyla, or at least 10 phyla. In at least some embodiments, the MRT compositions of the present disclosure may include bacteria that are members of at least 1 class, at least 2 classes, at least 3 classes, at least 4 classes, at least 5 classes, at least 6 classes, or at least 7 classes. In at least some embodiments, the MRT compositions of the present disclosure may include bacteria that are members of at least 1 order, at least 2 orders, at least 3 orders, at least 4 orders, at least 5 orders, at least 6 orders, or at least 7 orders. In at least some embodiments, the MRT compositions of the present disclosure may include bacteria that are members of at least 1 family, at least 2 families, at least 3 families, at least 4 families, at least 5 families, at least 6 families, at least 7 families. In at least some embodiments, the MRT compositions of the present disclosure may include bacteria that are members of at least 5, at least 10, at least 20, or at least 30 different genera of bacteria. In at least some embodiments, the MRT compositions of the present disclosure may include at least 10, at least 50, at least 100, at least 200, at least 300, or at least 400 different species of bacteria.

Samples of manufactured MRT compositions (manufactured as disclosed herein) were provided to Research and Testing Laboratory, Lubbock, Tex. for 16sRNA amplification and sequencing using the Illumina MiSeq platform. The purpose of this analysis was to obtain data useful for: validating the tentative potency release assays; and evaluating the intra- and inter-donor bacterial diversity and consistency.

The 16s rRNA analysis of all product batches demonstrated that the process disclosed herein resulted in desirable bacterial diversity profiles consistent. The data also indicated that the manufacturing process preserved a level of bacterial diversity consistent with normal feces and considered viable for the treatment of recurrent C. difficile, including the maintenance of the predominant phyla, Bacteroidetes and Firmicutes.

In addition, product made from the stool of individual donors over time maintained a very similar diversity profile. Table 2 presents a condensed version of the data, highlighting the means and standard deviations for percent bacteria by Order for all batches manufactured and tested. These "Order" categories represent the most commonly identified bacterial communities in the product batches.

TABLE 2

All batches (60) compared by Order

| Kingdom | Phylum | Class | Order | Average % | Std Dev |
|---|---|---|---|---|---|
| Bacteria | Bacteroidetes | Bacteroidia | Bacteroidales | 59 | 15 |
| Bacteria | Firmicutes | Bacilli | Lactobacillales | 0 | 1 |
| Bacteria | Firmicutes | Clostridia | Clostridiales | 35 | 11 |
| Bacteria | Firmicutes | Unknown | Unknown | 1 | 1 |
| Bacteria | Proteobacteria | Betaproteobacteria | Burkholderiales | 0 | 0 |
| Bacteria | Proteobacteria | Gammaproteobacteria | Enterobacteriales | 0 | 0 |
| No Hit | No Hit | No Hit | No Hit | 5 | 6 |

Example 11

16s rRNA Data—Individual Donors

To further illustrate the consistency of product manufacturing, multiple batches of product made from the same donor over time were analyzed. The following tables indicate that, over the clinical trial manufacturing period, multiple batches of product from a single donor exhibited similar diversity profiles. The microbiota for each donor was analyzed by bacterial Family to ensure that the trends in diversity would continue at a finer genetic level. The Shannon Diversity Index (also indicated by H') is an industry-accepted method of reporting the abundance and evenness of organisms present in the microbiome, and was used throughout this example. It has been shown to most completely encompass the variation in sampling depth and is therefore relevant for describing a complex microbial community. The bacterial diversity of Donor 1 is summarized in Table 3.

TABLE 3

Donor 1 - Means and Variation of Batches by Bacterial Family

| Family | Average % | Standard Deviation |
| --- | --- | --- |
| Bacteroidaceae | 36 | 7 |
| Bacteroidales (Unknown) | 0 | 0 |
| Clostridiaceae | 6 | 2 |
| Clostridiales (family) | 0 | 0 |
| Clostridiales (Unknown) | 7 | 3 |
| Enterobacteriaceae | 0 | 0 |
| Eubacteriaceae | 6 | 1 |
| Lachnospiraceae | 4 | 1 |
| Porphyromonadaceae | 2 | 1 |
| Prevotellaceae | 1 | 0 |
| Rikenellaceae | 5 | 2 |
| Ruminococcaceae | 18 | 3 |
| Staphylococcaceae | 0 | 6 |
| Streptococcaceae | 0 | 0 |
| XNo Hit | 15 | 6 |

The Shannon Diversity index for multiple samples from Donor 1 is summarized in Table 4.

TABLE 4

Donor 1 - Shannon Diversity Index

| Batch ID | Shannon Diversity Index (H') |
| --- | --- |
| 13000-071713 | 1.91 |
| 13000-072913 | 1.96 |
| 13000-080513 | 1.96 |
| 13000-080613 | 1.81 |
| 13000-092313 | 1.87 |
| 13000-092613 | 2.00 |
| 13000-110613 | 1.80 |
| 13000-021314 | 1.78 |
| AVERAGE | 1.89 |
| ST DEV | 0.08 |

The bacterial diversity of Donor 2 is summarized in Table 5.

TABLE 5

Donor 2 - Means and Variation of Batches by Bacterial Family

| Family | Average % | Standard Deviation |
| --- | --- | --- |
| Bacteroidaceae | 43 | 13 |
| Clostridiaceae | 2 | 2 |
| Clostridiales (family) | 4 | 3 |
| Eubacteriaceae | 6 | 3 |
| Firmicutes (Unknown) | 0 | 0 |
| Lachnospiraceae | 1 | 0 |
| Porphyromonadaceae | 3 | 1 |
| Rikenellaceae | 23 | 20 |
| Ruminococcaceae | 14 | 7 |
| Streptococcaceae | 1 | 1 |
| XNo Hit | 2 | 1 |

The Shannon Diversity index for multiple samples from Donor 2 is summarized in Table 6.

TABLE 6

Donor 2 - Shannon Diversity Index

| Batch ID | Shannon Diversity Index (H') |
| --- | --- |
| 13001-080613 | 1.45 |
| 13001-080913 | 1.70 |
| 13001-081213 | 1.46 |
| 13001-112513 | 1.44 |
| 13001-121013 | 1.64 |
| AVERAGE | 1.54 |
| ST DEV | 0.12 |

The bacterial diversity of Donor 3 is summarized in Table 7.

TABLE 7

Donor 3 - Means and Variation of Batches by Bacterial Family

| Family | Average % | Standard Deviation |
| --- | --- | --- |
| Bacteroidaceae | 70 | 11 |
| Burkholderiales (Unknown) | 0 | 0 |
| Clostridiaceae | 7 | 3 |
| Clostridiales (Unknown) | 5 | 2 |
| Eubacteriaceae | 4 | 2 |
| Firmicutes (Unknown) | 0 | 0 |
| Lachnospiraceae | 1 | 1 |
| Porphyromonadaceae | 1 | 1 |
| Rikenellaceae | 0 | 0 |
| Ruminococcaceae | 10 | 5 |
| Streptococcaceae | 0 | 0 |
| No Hit | 1 | 0 |

The Shannon Diversity index for multiple samples from Donor 3 is summarized in Table 8.

TABLE 8

Donor 3 - Shannon Diversity Index

| Batch ID | Shannon Diversity Index (H') |
| --- | --- |
| 13003-071613 | 1.19 |
| 13003-081313 | 0.98 |
| 13003-082013 | 1.04 |
| 13003-082713 | 1.06 |
| 13003-082913 | 1.01 |
| 13003-090513 | 1.17 |
| 13003-090913 | 1.10 |
| 13003-091113 | 0.78 |
| 13003-091213 | 0.76 |
| 13003-091313 | 1.02 |
| 13003-092513 | 1.21 |
| 13003-100213 | 0.97 |
| 13003-101013 | 1.23 |
| 13003-101513 | 0.42 |
| 13003-110513 | 1.70 |
| 13003-111913 | 1.22 |
| 13003-120213 | 1.28 |
| 13003-021414 | 1.28 |
| 13003-021714 | 1.18 |
| 13003-021914 | 1.45 |
| AVERAGE | 1.08 |
| ST DEV | 0.27 |

The bacterial diversity of Donor 4 is summarized in Table 10.

TABLE 10

Donor 4 - Means and Variation of Batches by Bacterial Family

| Family | Average % | Standard Deviation |
| --- | --- | --- |
| Bacteroidaceae | 44 | 12 |
| Burkholderiales (Unknown) | 1 | 1 |

TABLE 10-continued

Donor 4 - Means and Variation of Batches by Bacterial Family

| Family | Average % | Standard Deviation |
| --- | --- | --- |
| Clostridiaceae | 4 | 1 |
| Clostridiales (Unknown) | 6 | 2 |
| Eubacteriaceae | 8 | 5 |
| Firmicutes (Unknown) | 1 | 1 |
| Lachnospiraceae | 9 | 4 |
| Porphyromonadaceae | 1 | 0 |
| Rikenellaceae | 5 | 2 |
| Ruminococcaceae | 17 | 8 |
| Streptococcaceae | 0 | 1 |
| XNo Hit | 2 | 3 |

The Shannon Diversity index for multiple samples from Donor 4 is summarized in Table 11.

TABLE 11

Donor 4 - Shannon Diversity Index

| Batch ID | Shannon Diversity Index (H') |
| --- | --- |
| 13004-071513 | 1.65 |
| 13004-071613 | 1.93 |
| 13004-071813 | 1.75 |
| 13004-072213 | 1.89 |
| 13004-072313 | 1.97 |
| 13004-072913 | 1.46 |
| 13004-073113 | 1.34 |
| 13004-080513 | 1.64 |
| 13004-080713 | 1.79 |
| 13004-080813 | 1.72 |
| 13004-090313 | 1.64 |
| 13004-090413 | 1.98 |
| 13004-100913 | 1.46 |
| 13004-102913 | 1.87 |
| 13004-103113 | 1.80 |
| 13004-110413 | 1.56 |
| 13004-111913 | 1.77 |
| 13004-112113 | 1.78 |
| 13004-120213 | 1.84 |
| 13004-021414 | 2.02 |
| 13004-021814 | 1.56 |
| AVERAGE | 1.73 |
| ST DEV | 0.18 |

The bacterial diversity of Donor 5 is summarized in Table 12.

TABLE 12

Donor 5 - Means and Variation of Batches by Bacterial Family

| Family | Average % | Standard Deviation |
| --- | --- | --- |
| Bacteroidaceae | 48 | 6 |
| Bacteroidales (Unknown) | 0 | 0 |
| Burkholderiales (Unknown) | 0 | 0 |
| Clostridiaceae | 5 | 2 |
| Clostridiales (Unknown) | 4 | 1 |
| Eubacteriaceae | 5 | 2 |
| Lachnospiraceae | 4 | 0 |
| Porphyromonadaceae | 1 | 1 |
| Rikenellaceae | 4 | 1 |
| Ruminococcaceae | 18 | 5 |
| Sutterellaceae | 0 | 0 |
| No Hit | 9 | 5 |

The Shannon Diversity index for multiple samples from Donor 5 is summarized in Table 13.

TABLE 13

Donor 5 - Shannon Diversity Index

| Batch ID | Shannon Diversity Index (H') |
| --- | --- |
| 13005-080713 | 1.75 |
| 13005-081513 | 1.65 |
| 13005-100113 | 1.83 |
| 13003-110513 | 1.71 |
| 13005-110613 | 1.52 |
| 13005-120913 | 1.65 |
| AVERAGE | 1.68 |
| ST DEV | 0.11 |

The bacterial diversity of Donor 6 is summarized in Table 14.

TABLE 14

Donor 6 - Means and Variation of Batches by Bacterial Family

| Family | Average % | Standard Deviation |
| --- | --- | --- |
| Bacteroidaceae | 48 | NA |
| Bacteroidales (Unknown) | 0 | NA |
| Burkholderiales (Unknown) | 0 | NA |
| Clostridiaceae | 5 | NA |
| Clostridiales (Unknown) | 4 | NA |
| Eubacteriaceae | 5 | NA |
| Lachnospiraceae | 4 | NA |
| Porphyromonadaceae | 1 | NA |
| Rikenellaceae | 4 | NA |
| Ruminococcaceae | 18 | NA |
| Sutterellaceae | 0 | NA |
| No Hit | 9 | NA |

The Shannon Diversity index for multiple samples from Donor 6 is summarized in Table 15.

TABLE 15

Donor 6 - Shannon Diversity Index

| Batch ID | Shannon Diversity Index (H') |
| --- | --- |
| 13008-021314 | 1.59 |
| AVERAGE | NA |
| ST DEV | NA |

Due to the fact that only one batch was manufactured from Donor 6, no Average (H') or Standard Deviation of the (H') could be calculated at this time.

16s rRNA molecular characterization of the MRT composition as disclosed herein indicates that considerable bacterial diversity is preserved through the manufacturing process. While there are fluctuations in relative amounts of various bacteria between donors, the variation as measured by the standard deviation of the average percentages of specific bacterial Orders is quite small. Diversity profiles of product made from individual donors collected over time, demonstrated a high degree of similarity at the Family level (see Tables for Donors 1-5). In contrast, 16s data for microbes commonly associated with disease in patients were noticeably absent in the MRT compositions made from healthy donors. Product batches evaluated in this analysis were used in the Phase 2 clinical study, which demonstrated an 87% cure rate with acceptable mild to moderate adverse events. This data is important as it also substantiates that the level of bacterial diversity in MRT composition as disclosed herein provided therapeutic benefit.

Experiment 12

Success/Failure by Donor Gender

The success of treatments using the MRT compositions disclosed herein were tabulated taking into account the gender of the donor. It was observed that treatment success after a single dose of the MRT composition was greater when the fecal donor (whose fecal sample was utilized in manufacturing the MRT composition) was male. Since the Dose 2 response is more similar among the donors and these doses were delivered to antibiotic naïve patients (no antibiotic pretreatment and with active disease), it may be that the flora from the female donors are more susceptible to antibiotics.

TABLE 16

Success/Failure by Donor Gender

| Donor | Patient Dose 1 Success | Failure | Patient Dose 2 Success | Failure |
|---|---|---|---|---|
| F | 2/11 (18%) | 9/11 (82%) | 3/4 (75%) | 1/4 (25%) |
| M | 7/10 (70%) | 3/10 (30%) | 3/5 (60%) | 2/5 (40%) |
| F | 4/9 (44%) | 5/9 (56%) | 4/4 (100%) | |
| M | 3/3 (100%) | | 1/1 (100%) | |

U.S. Patent Application No. 61/337,283 is herein incorporated by reference.

U.S. Patent Application No. 61/351,184 is herein incorporated by reference.

U.S. patent application Ser. No. 13/576,573, published as U.S. Patent Application Pub. No. US 2013/0045274, is herein incorporated by reference.

U.S. patent application Ser. No. 14/093,913, published as U.S. Patent Application Pub. No. US 2014/0086877, is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of treating a gastrointestinal disorder, the method comprising:
    administering a first pre-treatment antibiotic to a patient with a gastrointestinal disorder;
    administering a second pre-treatment antibiotic to the patient with a gastrointestinal disorder;
    wherein the first pre-treatment antibiotic and the second pre-treatment antibiotic are different;
    administering a first dose of a microbiota restoration therapy composition to the patient;
    wherein the first dose of the microbiota restoration therapy composition is manufactured by:
        collecting a fresh stool sample from a human donor,
        adding saline and polyethylene glycol to the fresh stool sample, the polyethylene glycol being added at a concentration of 30-90 g/L, and
        filtering;
    wherein the first dose of the microbiota restoration therapy composition is pre-screened for bacterial diversity;
    wherein the pre-screened microbiota restoration therapy composition includes bacteria from at least seven different families and has a Shannon Diversity Index of 0.4-2.5 when calculated at the family level;
    wherein the microbiota restoration therapy composition comprises a mixture of an effective amount of fecal microbiota and an effective amount of polyethylene glycol; and
    administering a second dose of a microbiota restoration therapy composition to the patient.

2. The method of claim 1, wherein the first or second pre-treatment antibiotic includes vancomycin, fidaxomicin, rifaximimin, linezolid, daptomycin, quinupristin-dalfopristin, tigecycline, ceftaroline, ceftobiprole, televancin, teicoplanin, dalbavancin, metronidazole, ortivancin, or a combination thereof.

3. The method of claim 1, wherein the first or second pre-treatment antibiotic is administered at a dose of 0.01 mg per day to 5000 mg per day.

4. The method of claim 1, wherein the first or second pre-treatment antibiotic is administered orally, by enema, or by suppository.

5. The method of claim 1, wherein administering a first or second pre-treatment antibiotic to a patient with a gastrointestinal disorder includes administering a single dose of the first or second pre-treatment antibiotic to the patient.

6. The method of claim 1, wherein administering a first or second pre-treatment antibiotic to a patient with a gastrointestinal disorder includes administering two or more doses of the first or second pre-treatment antibiotic to the patient.

7. The method of claim 1, further comprising administering a post-treatment antibiotic to the patient after administering the microbiota restoration therapy composition to the patient.

8. The method of claim 7, wherein the post-treatment antibiotic is the same as one of the first or second pre-treatment antibiotic.

9. The method of claim 7, wherein the post-treatment antibiotic is different from one of the first or second pre-treatment antibiotic.

10. The method of claim 1, further comprising administering a second dose of the microbiota restoration therapy composition to the patient.

11. The method of claim 1, wherein administering a first pre-treatment antibiotic to a patient with a gastrointestinal disorder includes administering two or more doses of the first pre-treatment antibiotic to the patient and wherein administering a microbiota restoration therapy composition to the patient includes administering two or more doses of the microbiota restoration therapy composition to the patient.

12. The method of claim 1, wherein manufacturing the microbiota restoration therapy composition comprises:
    wherein filtering forms a filtrate;
    transferring the filtrate to a sample bag;
    sealing the sample bag;
    pre-cooling the sample bag; and
    freezing the sample bag.

13. The method of claim 12, wherein administering a microbiota restoration therapy composition to the patient includes thawing the sample bag and administering the microbiota restoration therapy composition with an enema tube.

14. The method of claim 1, wherein the gastrointestinal disorder is a *C. difficile* infection.

15. A method of treating a gastrointestinal disorder, the method comprising:
- pre-treating a patient with a gastrointestinal disorder with a primary dose of a first antibiotic, the first antibiotic including vancomycin, fidaxomicin, rifaximimin, linezolid, daptomycin, quinupristin-dalfopristin, tigecycline, ceftaroline, ceftobiprole, televancin, teicoplanin, dalbavancin, metronidazole, ortivancin, or a combination thereof;
- pre-treating the patient with a secondary dose of a second antibiotic, the second antibiotic including vancomycin, fidaxomicin, rifaximimin, linezolid, daptomycin, quinupristin-dalfopristin, tigecycline, ceftaroline, ceftobiprole, televancin, teicoplanin, dalbavancin, metronidazole, ortivancin, or a combination thereof;
- administering a dose of a microbiota restoration therapy composition to the patient;
- wherein the microbiota restoration therapy composition is manufactured by:
  - collecting a fresh stool sample from a human donor,
  - adding saline and polyethylene glycol to the fresh stool sample, the polyethylene glycol being added at a concentration of 30-90 g/L, and
  - filtering;
- wherein the microbiota restoration therapy composition is pre-screened for bacterial diversity;
- wherein the pre-screened microbiota restoration therapy composition includes bacteria from at least seven different families and the pre-screened microbiota restoration therapy composition includes bacteria from at least seven different families and has a Shannon Diversity Index of 0.4-2.5 when calculated at the family level; and
- wherein the microbiota restoration therapy composition comprises a mixture of an effective amount of fecal microbiota and an effective amount of polyethylene glycol.

16. The method of claim 15, further comprising administering a post-treatment antibiotic to the patient after administering the microbiota restoration therapy composition to the patient.

17. The method of claim 15, further comprising administering a second dose of the microbiota restoration therapy composition to the patient.

18. The method of claim 15, wherein administering a microbiota restoration therapy composition to the patient includes administering the microbiota restoration therapy composition with an enema tube.

19. The method of claim 15, wherein the gastrointestinal disorder is a *C. difficile* infection.

20. A method of treating a gastrointestinal disorder, the method comprising:
- administering a primary dose of a microbiota restoration therapy composition to the patient;
- administering a secondary dose of the microbiota restoration therapy composition to the patient;
- wherein the microbiota restoration therapy composition is manufactured by:
  - collecting a fresh stool sample from a human donor,
  - adding saline and polyethylene glycol to the fresh stool sample, the polyethylene glycol being added at a concentration of 30-90 g/L, and
  - filtering;
- wherein the microbiota restoration therapy composition is pre-screened for bacterial diversity and the pre-screened microbiota restoration therapy composition includes bacteria from at least seven different families and has a Shannon Diversity Index of 0.4-2.5 when calculated at the family level; and
- wherein the microbiota restoration therapy composition comprises a mixture of an effective amount of fecal microbiota and an effective amount of polyethylene glycol.

* * * * *

UNITED STATES PATENT AND TRADEMARK OFFICE
CERTIFICATE OF CORRECTION

PATENT NO. : 9,511,099 B2
APPLICATION NO. : 14/504927
DATED : December 6, 2016
INVENTOR(S) : Lee A. Jones et al.

Page 1 of 1

It is certified that error appears in the above-identified patent and that said Letters Patent is hereby corrected as shown below:

In the Specification

Column 22
Line 12: after "each containing a", delete "in"

Signed and Sealed this
Twenty-eighth Day of February, 2017

Michelle K. Lee
*Director of the United States Patent and Trademark Office*